United States Patent
Haecker et al.

(10) Patent No.: US 11,175,293 B1
(45) Date of Patent: Nov. 16, 2021

(54) RAPID ASSAY FOR DETECTION OF SARS-COV-2 ANTIBODIES

(71) Applicant: UNIVERSITY OF UTAH RESEARCH FOUNDATION, Salt Lake City, UT (US)

(72) Inventors: Hans Haecker, Salt Lake City, UT (US); Vanessa Redecke, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 17/140,321

(22) Filed: Jan. 4, 2021

(51) Int. Cl.
| | | |
|---|---|---|
| C07K 14/165 | (2006.01) | |
| G01N 33/68 | (2006.01) | |
| C07K 16/10 | (2006.01) | |
| C07K 14/47 | (2006.01) | |
| G01N 33/49 | (2006.01) | |
| C07K 16/30 | (2006.01) | |

(52) U.S. Cl.
CPC .......... *G01N 33/68* (2013.01); *C07K 14/165* (2013.01); *C07K 14/47* (2013.01); *C07K 16/10* (2013.01); *C07K 16/3061* (2013.01); *G01N 33/49* (2013.01); *C07K 2319/02* (2013.01); *C07K 2319/30* (2013.01); *C07K 2319/73* (2013.01)

(58) Field of Classification Search
None
See application file for complete search history.

(56) References Cited

U.S. PATENT DOCUMENTS

| | | | |
|---|---|---|---|
| 9,879,090 | B2 | 1/2018 | Bertrand et al. |
| 2007/0042350 | A1 | 2/2007 | Li et al. |
| 2007/0053878 | A1 | 3/2007 | Haagmans et al. |
| 2007/0248616 | A1 | 10/2007 | Brownlie et al. |
| 2009/0029924 | A1 | 1/2009 | Strongin et al. |
| 2012/0258126 | A1 | 10/2012 | Scholler et al. |
| 2014/0120113 | A1 | 5/2014 | Kwaks et al. |
| 2015/0110826 | A1 | 4/2015 | Bayne et al. |
| 2017/0269101 | A1 | 9/2017 | Yerramilli et al. |
| 2017/0356921 | A1 | 12/2017 | Van Roosmalen et al. |
| 2018/0292408 | A1 | 10/2018 | Qi |
| 2020/0040042 | A1* | 2/2020 | Chappell ............ C12N 15/1034 |

FOREIGN PATENT DOCUMENTS

| | | |
|---|---|---|
| AU | 4876399 A | 11/1999 |
| CN | 108463229 A | 8/2018 |
| CN | 108778308 A | 11/2018 |
| CN | 109503711 A | 3/2019 |
| KR | 20180118175 A | 10/2018 |
| WO | 2007053165 A2 | 5/2007 |
| WO | 2017068352 A1 | 4/2017 |
| WO | 2017070364 A1 | 8/2018 |
| WO | 2019217967 A1 | 11/2019 |
| WO | 2020099922 A1 | 5/2020 |
| WO | 2020163721 A1 | 8/2020 |

OTHER PUBLICATIONS

Dutta et al., "Search for potential target site of nucleocapsid gene for the design of an epitope-based SARS DNA vaccine," Immunol. Let., vol. 118, 2008, pp. 65-71.
Dutta et al., "The Nucleocapsid Protein of SARS-CoV-2: a Target for Vaccine Development," J Virol., vol. 94, No. 13, 2020, pp. e00647-20.
Grant et al., "Analysis of the SARS-CoV-2 spike protein glycan shield reveals implications for immune recognition," Sci. Rep., vol. 10, 2020, 12 pages.
Grzelak et al., "A comparison of four serological assays for detecting anti-SARS-CoV-2 antibodies in human serum samples from different populations," Sci. Transl. Med., vol. 12, 2020, eabc3103, 15 pages.
Gudbjartsson et al., "Humoral Immune Response to SARS-CoV-2 in Iceland," N. Engl. J. Med., vol. 383, No. 18, 2020, pp. 1724-1734.
Gupta et al., "Expression, purification, and characterization of an anti-RBCFab-p24 fusion protein for hemagglutination-based rapid detection of antibodies to HIV in whole blood," Protein Expr. Purif., vol. 26, 2002, pp. 162-170.
Gupta et al., "Whole-blood agglutination assay for on-site detection of human immunodeficiency virus infection," J. Clin. Microbiol., vol. 41, No. 7, 2003, pp. 2814-2821.
Habib et al., "V(H)H (nanobody) directed against human glycophorin A: a tool for autologous red cell agglutination assays," Anal. Biochem., vol. 438, 2013, pp. 82-89.
Hachim et al., "ORF8 and ORF3b antibodies are accurate serological markers of early and late SARS-CoV-2 infection," Nat. Immunol., vol. 21, 2020, pp. 1293-1301.
Huo et al., "Neutralizing nanobodies bind SARS-CoV-2 spike RBD and block interaction with ACE2", Nature Structural & Molecular Biology, vol. 27, 2020, pp. 846-854.
Kemp et al., "Autologous red cell agglutination assay for HIV-1 antibodies: simplified test with whole blood," Science, vol. 241, 1988, pp. 1352-1354.
Kontou et al., "Antibody Tests in Detecting SARS-CoV-2 Infection: A Meta-Analysis," Diagnostics, vol. 10, No. 319, 2020, 15 pages.
Lee et al., "Detection of antibodies against SARS-Coronavirus using recombinant truncated nucleocapsid proteins by ELISA," J. Microbiol. Biotechnol., vol. 18, No. 10, 2008, pp. 1717-1721.
Lee et al., "Production of specific antibodies against SARS-coronavirus nucleocapsid protein without cross reactivity with human coronaviruses 229E and OC43," J. Vet. Sci., vol. 11, No. 2, 2010, pp. 165-167.
Okba et al., "Serologic Detection of Middle East Respiratory Syndrome Coronavirus Functional Antibodies", Emerging Infectious Dis, vol. 26, No. 5, 2020, pp. 1024-1027.
Ravichandran et al., "Antibody signature induced by SARS-CoV-2 spike protein immunogens in rabbits," Sci. Transl. Med., vol. 12, 2002, eabc3539, 7 pages.

(Continued)

*Primary Examiner* — Michael D Burkhart
(74) *Attorney, Agent, or Firm* — Michael Best & Friedrich LLP

(57) ABSTRACT

Described herein are diagnostic and control fusion protein reagents and methods for use thereof in simple rapid and inexpensive hemagglutinin assays for the detection of subject antibodies directed to the SARS-CoV-2 virus.

20 Claims, 8 Drawing Sheets

Figure 1:
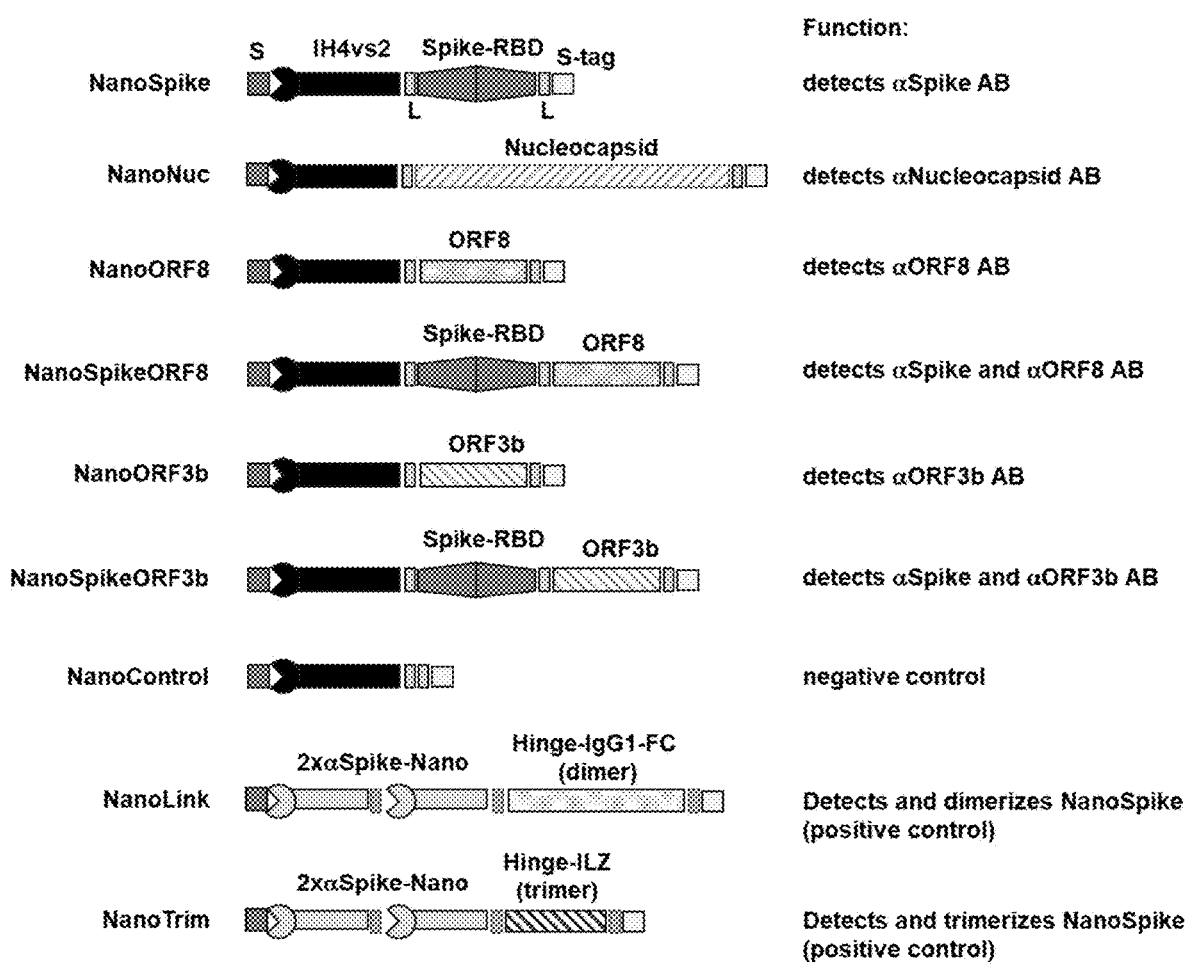
Figure 2:
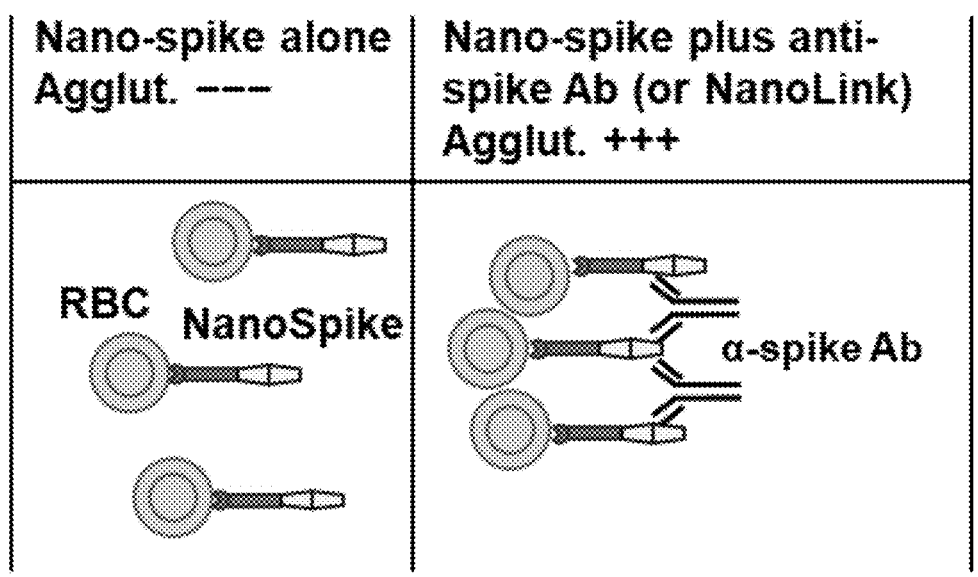
Figure 3:
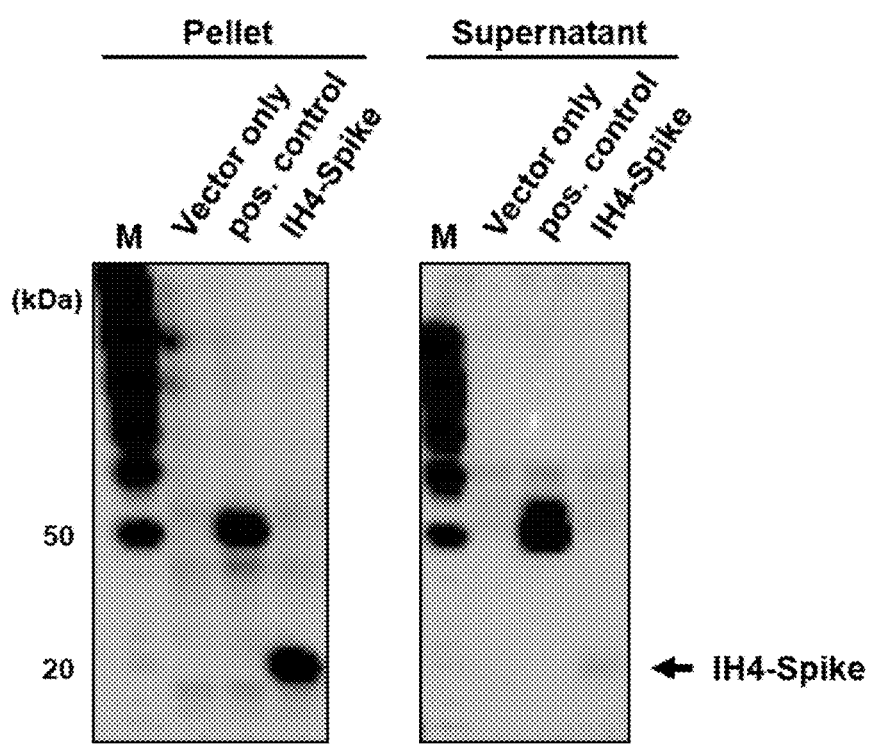

Specification includes a Sequence Listing.

(56) References Cited

OTHER PUBLICATIONS

Redecke et al., "Hematopoietic progenitor cell lines with myeloid and lymphoid potential," Nat. Methods, vol. 10, No. 8, 2013, pp. 795-803.

Sah et al., "Complete Genome Sequence of a 2019 Novel Coronavirus (SARS-CoV-2) Strain Isolated in Nepal", American Society for Microbiology, vol. 9, Issue 11, 2020, 3 pages.

Salvatori et al., "SARS-CoV-2 Spike Protein: an optimal immunological target for vaccines," J. Transl. Med., vol. 18, No. 222, 2020, 3 pages.

Tai et al., "Characterization of the receptor-binding domain (RBD) of 2019 novel coronavirus: implication for development of RBD protein as a viral attachment inhibitor and vaccine," Cell. Mol. Immunol., vol. 17, No. 6, 2020, pp. 613-620.

Tillib et al., "Formatted single-domain antibodies can protect mice against infection with influenza virus (H5N2)", Antiviral Research, vol. 97, 2013, pp. 245-254.

Townsend et al., "A haemagglutination test for rapid detection of antibodies to SARS-CoV-2", Nature Communications, Mar. 2021, pp. 1-6.

\* cited by examiner

RAPID ASSAY FOR DETECTION OF SARS-COV-2 ANTIBODIES

REFERENCE TO SEQUENCE LISTING

This application is filed with a Computer Readable Form of a Sequence Listing in accordance with 37 C.F.R. § 1.821(c). The text file submitted by EFS, "026389-9305-US01_sequence_listing_3 Aug. 2021_ST25.K" was created on Aug. 3, 2021, contains 67 sequences, has a file size of 199 Kbytes, and is hereby incorporated by reference in its entirety.

TECHNICAL FIELD

Described herein are diagnostic and control fusion protein reagents and methods for use thereof in simple rapid and inexpensive hemagglutinin assays for the detection of subject antibodies directed to the SARS-CoV-2 virus.

BACKGROUND

The COVID19 pandemic caused by SARS-CoV-2 approaches its first anniversary with close to one million deaths worldwide. At this point, countermeasures are largely restricted to symptomatic therapeutic interventions and prophylactic social distancing. Without a clear timeline for the availability of better therapeutic options and just starting vaccination efforts, it is clear that proper pandemic management hinges on the availability of diagnostic tests, including those revealing the presence of the virus itself to identify infectious carriers as well as those detecting antibody responses to assess the kinetics of the pandemic and the susceptibility of individual patients and the population at large. The latter aspect will also be relevant for evaluation and guidance of large-scale vaccination efforts.

Proper management of the pandemic caused by SARS-CoV-2 (COVID19) depends on laboratory tests that reliably detect (i) active virus, to identify virus carriers and (ii) SARS-CoV-2-specific antibodies, to identify individuals who were previously exposed to SARS-CoV-2, are at risk for infection or have successfully been vaccinated.

As investigated in detail in a comparative meta-analysis study, a significant (and growing) number of antibody tests are currently availabel, including various ELISAs (enzyme-linked immunosorbent assay) and related technologies, such as ECLIA (electrochemiluminescence immunoassay), FMIA (fluorescent microsphere Immunoassay), CMIA (chemiluminescent microparticle immunoassay) and ELFA (enzyme-linked fluorescent assay) [1]. Most of these tests exhibit appropriate specificity and sensitivity and are suitable for high throughput format in diagnostic laboratories [1]. Disadvantages include their restriction to special equipment and professional laboratories, relatively high costs and long turn-around times from sample acquisition to results. An alternative technology is the lateral flow immuno-assay (LVIA), which in principle can be conducted with minimal laboratory equipment. However, as also analyzed directly in referenced study, LFIAs typically exhibit appropriate specificity but restricted sensitivity, usually below 80%, and are relatively expensive (~$18 per test) [1].

While small, short-term studies indicated that antibody responses in asymptomatic patients may wean after weeks, at least two large scale studies have now demonstrated that antibody levels in symptomatic patients against the Spike protein and the Nucleocapsid (N) protein (NP) remain sustained at relatively high levels for at least 4-6 months [2]. These studies suggest that assessment of SARS-CoV-2-specific antibodies represents a proper tool for epidemiological studies and, likely, at least intermediate-term protection of convalescent patients. While studies so far are based on tests using the Spike or Nucleocapsid proteins as antigens, a recent study using luciferase-immunoprecipitation highlighted additional immunogenic proteins of SARS-CoV-2, in particular a small protein encoded by the open reading frame (ORF) 8 (ORF8), a known pathogenicity factor [3].

What is needed are simple, rapid, and inexpensive field tests for the detection of SARS-CoV-2-specific antibodies.

SUMMARY

One embodiment described herein is a nucleotide sequence encoding a polypeptide, wherein the polypeptide comprises a human red blood cell binding antibody domain (RBD) and a SARS CoV-2 virus protein domain (CVD). In one aspect, the RBD comprises a glycophorin A-binding nanobody comprising 90-99% identity to SEQ ID NO: 22. In another aspect, the CVD comprises one or more of a spike protein, a nucleocapsid protein, ORF8 protein, ORF3b protein, or envelope protein comprising 90-99% identity to all or a portion of SEQ ID NO: 24, 26, 28, or 30. In another aspect, the polypeptide has the structure: SS-GAP-RBD-GL2-CVD-GL3-AFT or SS-GL1-RBD-GL2-CVD-GL3-CVD-GL4-AFT; wherein: SS is a secretion signal domain; RBD is a glycophorin A-binding nanobody domain; GAP, GL1, GL2, GL3, and GL4 are linker domains; CVD is a SARS CoV-2 virus polypeptide domain comprising a spike protein, nucleocapsid protein, ORF8 protein, ORF3b protein, or envelope protein domains; and AFT is an affinity purification tag sequence. In another aspect, the SS comprises 90-99% identity to SEQ ID NO: 20. In another aspect, the GAP, GL1, GL2, GL3, or GL4 comprises 90-99% identity to one or more of SEQ ID NO: 38, 40, 42, 44, or 46. In another aspect, the AFT comprises 90-99% identity to one or more of SEQ ID NO: 58, 60, 62, or 64. In another aspect, the nucleotide sequence has 90% to 99% identity to SEQ ID NO: 1, 3, 5, 7, 9, or 11. In another aspect, the nucleotide sequence is one of SEQ ID NO: 1, 3, 5, 7, 9, or 11.

Another embodiment described herein is a polynucleotide vector comprising a nucleotide sequence described herein.

Another embodiment described herein is a cell comprising a polynucleotide vector comprising a nucleotide sequence described herein.

Another embodiment described herein is a polypeptide encoded by a nucleotide sequence described herein.

Another embodiment described herein is a polypeptide encoded by a nucleotide sequence described herein, wherein the polypeptide has 90% to 99% identity to SEQ ID NO: 2, 4, 6, 8, 10, or 12.

Another embodiment described herein is a polypeptide encoded by a nucleotide sequence described herein, wherein the polypeptide is SEQ ID NO: 2, 4, 6, 8, 10, or 12.

Another embodiment described herein is a diagnostic reagent or research tool comprising a polypeptide encoded by the nucleotide sequence described herein.

Another embodiment described herein is a method or means for manufacturing a nucleotide sequence as described herein or a polypeptide encoded by the nucleotide sequence, the process comprising: transforming or transfecting a cell with a nucleic acid comprising the nucleotide sequence; growing the cells; optionally, harvesting the cells and isolating quantities of the nucleotide sequence; inducing expression of a polypeptide encoded by the nucleotide sequence; harvesting the cells; and isolating and purifying the polypeptide.

Another embodiment described herein is a nucleotide sequence or a polypeptide encoded by the nucleotide sequence, each produced by a method or means described herein.

Another embodiment described herein is a nucleotide sequence encoding a diagnostic control polypeptide, wherein the polypeptide comprises: (a) a glycophorin A-binding nanobody domain comprising 90-99% identity to SEQ ID NO: 22; (b) one or more anti-SARS Co-V-2 nanobody domains comprising 90-99% identity to SEQ ID NO: 32 and one or more multimerization domains comprising 90-99% identity to SEQ ID NO: 34 o4 36. In one aspect, the polypeptides have the structure: SS-GAP-RBD-G L5-AFT; SS-GAP-anti-CVD-GL6-anti-CVD-GL7-IgGFC-GL8-AFT; or SS-GAP-anti-CVD-GL6-anti-CVD-SGT-HIZD-GL8-AFT; wherein: SS is a secretion signal domain; RBD is a glycophorin A-binding nanobody domain; GAP, GL5, GL6, GL7, GL8, and SGT are linker domains; Anti-CVD is an anti-SARS CoV-2 surface glycoprotein receptor binding domain nanobody domain; IgGFC is a human immunoglobulin FC dimerization domain; HIZD is a Hinge-isoleucine zipper trimerization domain; and AFT is an affinity purification tag sequence. In another aspect, the SS comprises 90-99% identity to SEQ ID NO: 20. In another aspect, the GAP, SGT, GL5, GL6, GL7, or GL8 comprises 90-99% identity to one or more of SEQ ID NO: 38, 48, 50, 52, 54, or 56. In another aspect, the AFT comprises 90-99% identity to one or more of SEQ ID NO: 58, 60, 62, or 64. In another aspect, the nucleotide sequence has 90% to 99% identity to SEQ ID NO: 13, 15, or 17. In another aspect, the nucleotide sequence is one of SEQ ID NO: 13, 15, or 17.

Another embodiment described herein is a polynucleotide vector comprising a nucleotide sequence encoding a diagnostic control polypeptide as described herein.

Another embodiment described herein is a cell comprising a polynucleotide vector comprising a nucleotide sequence encoding a diagnostic control polypeptide as described herein.

Another embodiment described herein is a diagnostic control polypeptide as described herein.

Another embodiment described herein is a diagnostic control polypeptide having 90% to 99% identity to SEQ ID NO: 14, 16, or 18.

Another embodiment described herein is a diagnostic control polypeptide having the polypeptide sequence of SEQ ID NO: 14, 16, or 18.

Another embodiment described herein is a diagnostic reagent or research tool comprising a polypeptide encoded by a nucleotide sequence described herein.

Another embodiment described herein is a diagnostic or control polypeptide comprising the amino acid sequence of SEQ ID NO: 2, 4, 6, 8, 10, 12, 14, 16, or 18.

Another embodiment described herein is a method for evaluating whether a subject is infected or has been infected with SARS-CoV-2, the method comprising: (a) providing a sample of a biological fluid from a subject in need of diagnosis; (b) combining the biological fluid with a diagnostic polypeptide comprising 90 to 99% identity to the amino acid sequence of SEQ ID NO: 2, 4, 6, 8, 10, 12 to form a subject sample; (c) optionally, combining a negative control reagent or a positive control polypeptide comprising 90 to 95% identity to the amino acid sequence of SEQ ID NO: 14 (negative control) or SEQ ID NO: 16 or 18 (positive controls), with the biological fluid and a diagnostic polypeptide comprising 90 to 99% identity to the amino acid sequence of SEQ ID NO: 2, 10, or 12 to form one or more control samples; (d) permitting the subject sample and control samples to incubate for a period of time; (e) evaluating the results by visualization, imaging, optical density, impedance, or microscopy; and (f) optionally, comparing the subject sample and control samples to validate the subject sample results; wherein the presence of hemagglutination in the subject sample is a positive diagnostic indication of SARS-CoV-2 infection, and the absence of hemagglutination in the subject sample is a negative diagnostic indication of SARS-CoV-2 infection. In one aspect, the biological fluid is whole blood, plasma, or serum. In another aspect, when the biological fluid is plasma or serum, washed human red blood cells of blood group O are combined with the subject sample and the diagnostic or control polypeptides in steps (b) or (c). In another aspect, wherein the diagnostic or control polypeptides have a concentration of about 10 μg/mL to about 100 μg/mL. In another aspect, the subject sample and/or control samples in steps (b) and/or (c) are dispensed on a test card, glass slide, microtiter plate, or other substrate prior to step (d). In another aspect, when the subject sample has a positive diagnostic indication of SARS-CoV-2 infection, the method further comprises: (g) administering one or more therapeutics or treatments to the subject.

Another embodiment described herein is a kit comprising: (a) one or more diagnostic or control polypeptides comprising the amino acid sequence of SEQ ID NO: 2, 4, 6, 8, 10, 12, 14, 16, or 18; (b) a test substrate; and (c) optionally, a label or instructions for use. In one aspect, the kit further comprises one or more of alcohol saturated towelettes; finger prick lances, capillaries, or gloves.

Another embodiment described herein is the use of a polypeptide comprising 90 to 99% identity to the amino acid sequence of SEQ ID NO: 2, 4, 6, 8, 10, 12, 14, 16, or 18 for the diagnosis of SARS-CoV-2 in a subject in need of diagnosis thereof.

DESCRIPTION OF THE DRAWINGS

FIG. 1 shows schematic representations of the diagnostic and control fusion protein constructs. Key: S, secretion signal (IFNβ); IH4vs2, GPA-specific nanobody IH4vs2, which is efficiently secreted from mammalian cells (as opposed to the original IH4 nanobody); L, flexible linker; Spike, Spike-RBD of SARS-CoV-2; S-tag, Tandem-Strep-tag mediating binding to StrepTactin® matrix (IBA) for affinity purification; Nucleocapsid, Nucleocapsid protein of SARS-CoV-2, ORF8, ORF8 of SARS-CoV-2, ORF3b, ORF3b of SARS-CoV-2; 2xαSpike-Nano, tandem-fusion construct of two Spike-RBD-binding H11-D4 nanobodies, separated by flexible linker; Hinge-IgG1-FC, dimerizing Hinge-FC moiety of IgG1; Hinge-ILZ, trimerizing hinge-isoleucin-zipper domain. Polypeptide sequences are shown in Table 1.

FIG. 2 shows the principle of Nano-spike-mediated hemagglutination in the presence of virus-specific (e.g., Spike-specific) antibodies (or the positive control nanobody, such as NanoLink).

FIG. 3 shows a fusion protein of the IH4 nanobody and the Spike RBD is not efficiently secreted. A fusion construct of the IH4 nanobody (SEQ ID NO: 65-66) and the Spike-RBD (IH4-Spike) was transfected into HEK293T cells along with a negative (vector) control and a positive control construct, and protein expression was analyzed in the cell pellet and the supernatant. Note the almost complete lack or IH4-Spike in the supernatant. Vector only-transfected cells (vector only) and cells transfected with a secreted control protein (positive control) show expected results.

Figure 4:
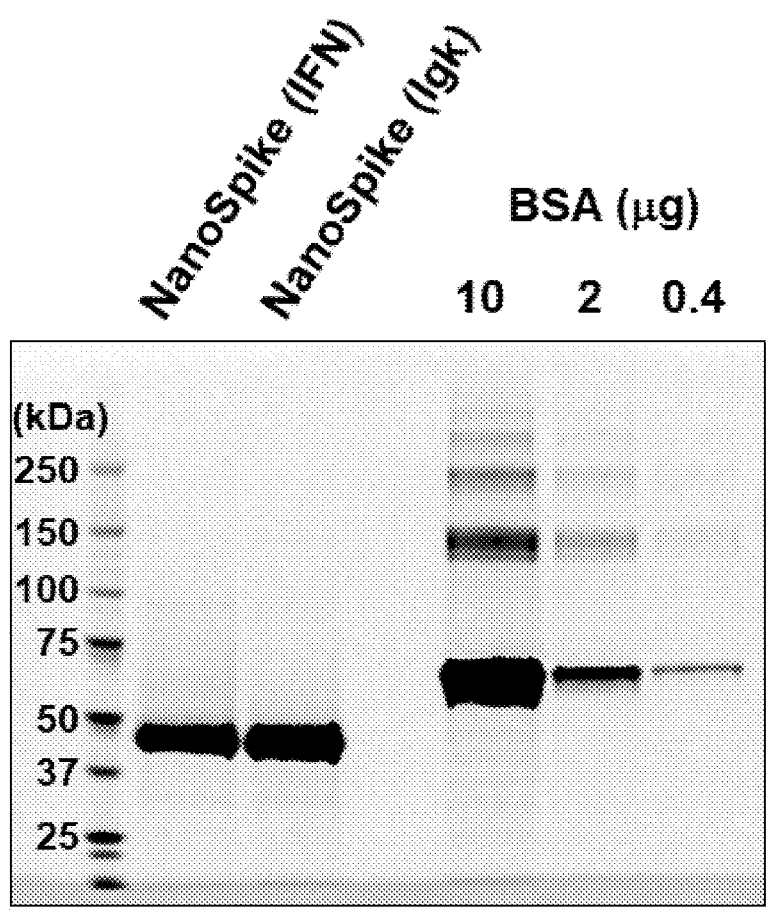

FIG. 4 shows two mutations in the IH4 nanobody permit efficient secretion of Spike-RBD fusion proteins. Fusion constructs with modified forms of IH4 (IH4vs2) (SEQ ID NO:21-22), i.e., IH4vs2-Spike (i.e., "NanoSpike"; SEQ ID NO:1-2) and a similar construct containing an Igk-leader sequence (instead of the lfnb leader sequence of NanoSpike) were purified from the supernatant of transfected Expi293F™ (Thermo Fisher Scientific) cells, followed by SDS PAGE and protein (Sypro Ruby) stain. Protein yield from 25 mL of Expi293F™ cell cultures were 2.3 mg (NanoSpike) and 2.9 mg (NanoSpike-Igk). BSA at 10 µg, 2 µg, and 0.4 µg is shown for comparison.

Figure 5:
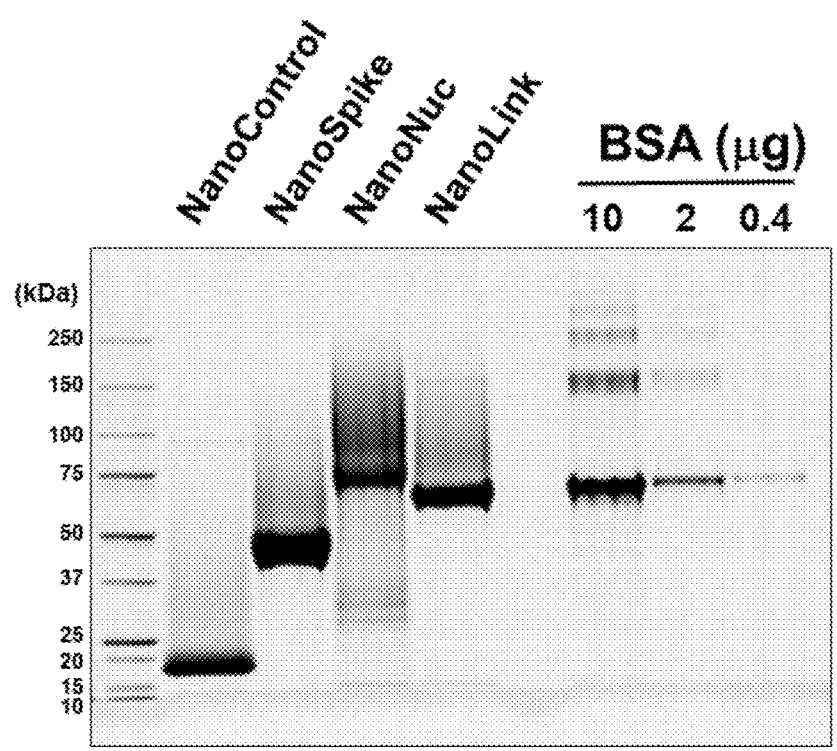

FIG. 5 shows an example of recombinant protein production. Indicated proteins were expressed in Expi293F™ (Thermo Fisher Scientific) cells and purified by affinity purification followed by SDS PAGE and protein (Sypro Ruby) stain. Protein yield from 25 mL of Expi293F™ cell cultures were 2 mg (NanoControl; SEQ ID NO: 14), 3.75 mg (NanoSpike; SEQ ID NO: 2), 0.55 mg (NanoNuc; SEQ ID NO: 4) and 1.25 mg (NanoLink; SEQ ID NO: 16). BSA at 10 µg, 2 µg, and 0.4 µg is shown for comparison.

Figure 6:
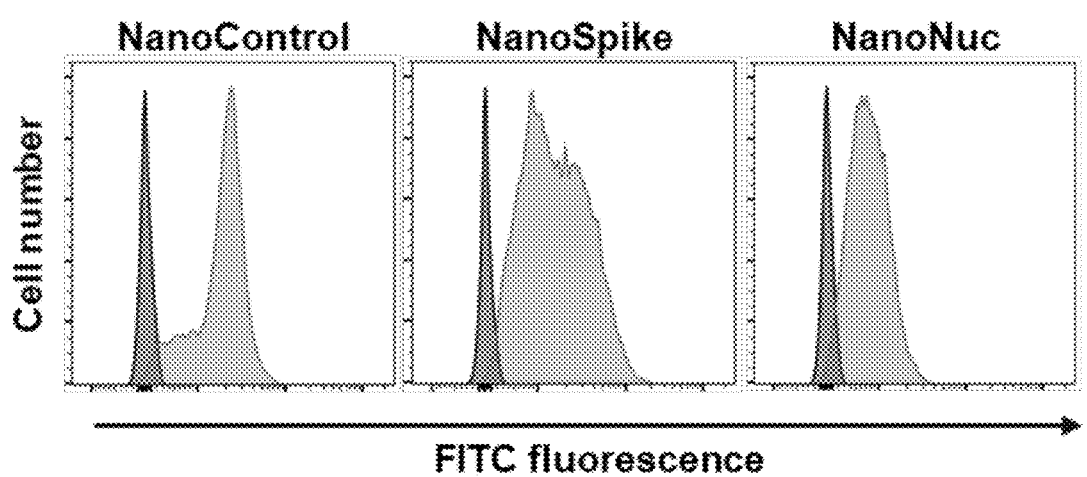

FIG. 6 shows that recombinant proteins containing the Glycophorin A-binding nanobody IH4vs2 bind human red blood cells. Flow cytometry analysis of human RBC that were treated with 30 µg/mL recombinant proteins (as indicated), followed by incubation without (dark) or with FITC-labeled antibody against the Strep-tag (light).

Figure 7:
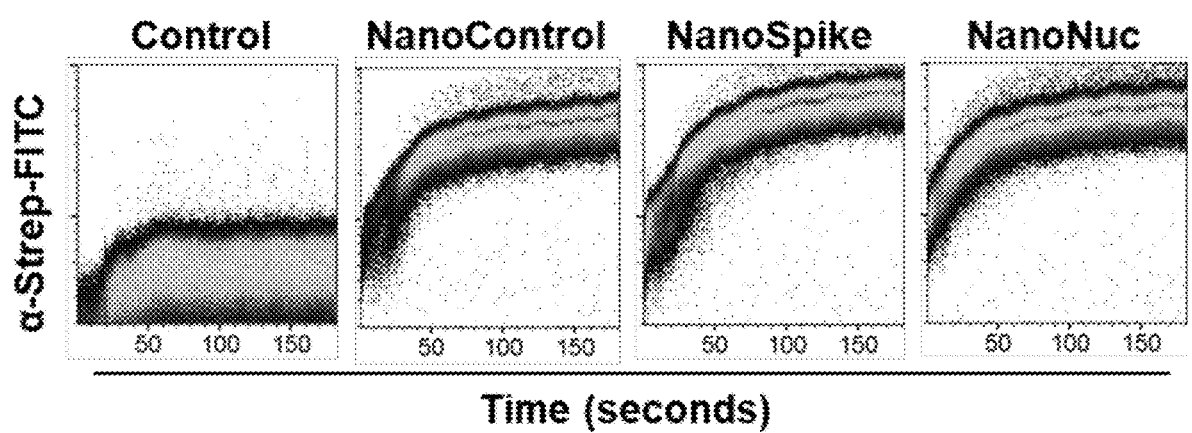

FIG. 7 shows that nanobody-fusion proteins bind RBCs rapidly and quantitatively. Kinetics of RBC-binding of nanobody-fusion proteins analyzed by flow cytometry. Anti-Strep-FITC antibody alone (control) or together with indicated recombinant proteins was added to human RBC (time point 0) and binding was analyzed by flow cytometry during time.

Figure 8:
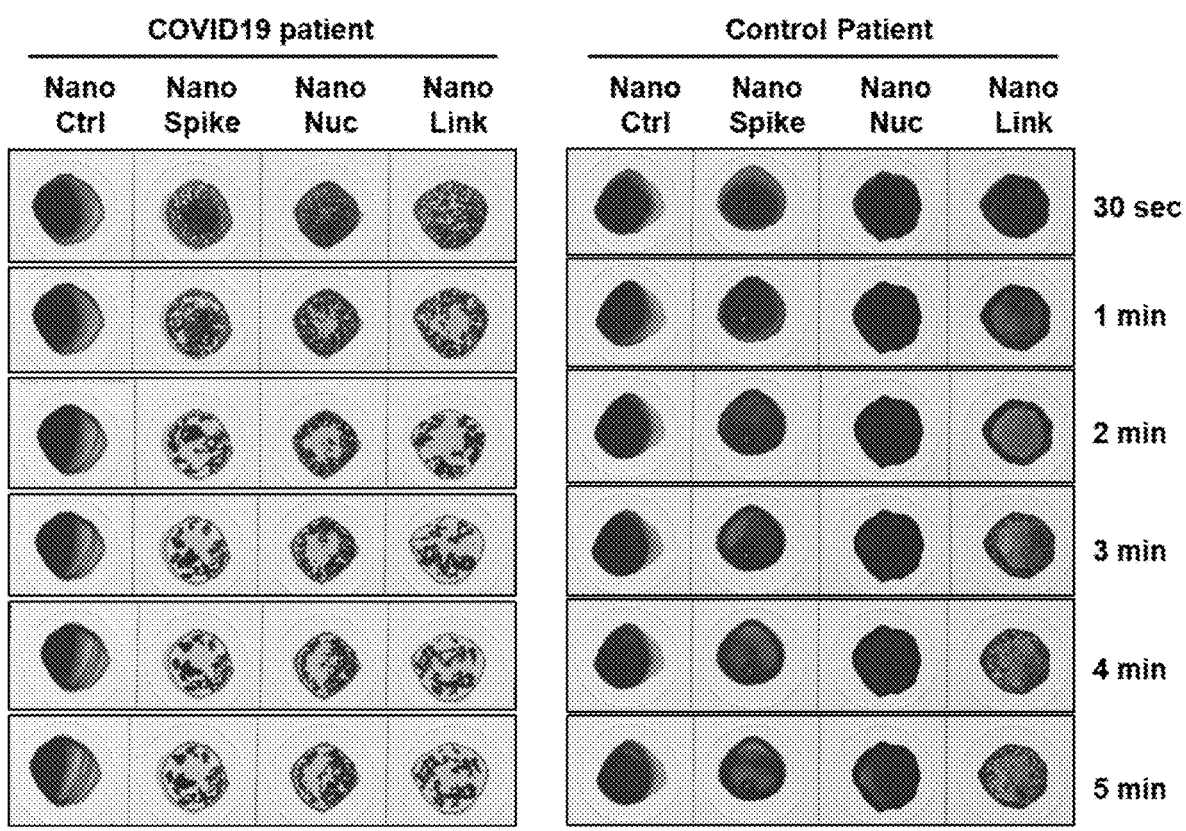

FIG. 8 shows that serum from a COVID19 convalescent patient triggers Nanospike- and NanoNuc-mediated hemagglutination. Indicated recombinant proteins (30 µg/mL) were added to washed RBC along with serum from a COVID19 convalescent patient (left) or a healthy control patient (right). The mixture was spread with a pipette tip and analyzed after a short incubation.

DETAILED DESCRIPTION

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are well known and commonly used in the art. In case of conflict, the present document, including definitions, will control. Preferred methods and materials are described below, although methods and materials similar or equivalent to those described herein can be used in practice or testing of the present invention.

As used herein, the terms "amino acid," "nucleotide," "polynucleotide," "vector," "polypeptide," and "protein" have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or Y) are used herein.

As used herein, the terms such as "include," "including," "contain," "containing," "having," and the like mean "comprising." The present disclosure also contemplates other embodiments "comprising," "consisting of," and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

As used herein, the term "subject" refers to an animal. Typically, the subject is a mammal. A subject also refers to primates (e.g., humans, male or female; infant, adolescent, or adult), non-human primates, rats, mice, rabbits, pigs, cows, sheep, goats, horses, dogs, cats, fish, birds, and the like. In one embodiment, the subject is a human. In another embodiment, the subject is a human suspected of being infected with SARS-CoV-2 or that is infected with SARS-CoV-2.

As used herein, a subject is "in need of treatment" if such subject would benefit biologically, medically, or in quality of life from such treatment. A subject in need of treatment does not necessarily present symptoms, particular in the case of preventative or prophylaxis treatments. In one aspect, the subject may need diagnosis of a condition prior to treatment. Embodiments described herein can be used to make or confirm such a diagnosis.

As used herein a subject is "in need of diagnosis" if such subject would benefit biologically, medically, or in quality of life from such diagnosis. In one embodiment a subject needs diagnosis of SARS-CoV-2. In one aspect the subject may be presenting symptoms of SARS-CoV-2, may have been exposed to another individual presenting symptoms of SARS-CoV-2, may be a "carrier" of SARS-CoV-2 (without clinical presentation or symptoms), or may have previously been infected with SARS-CoV-2 and is in need of confirmation of such infection.

As used herein, the terms "inhibit," "inhibition," or "inhibiting" refer to the reduction or suppression of a given biological process, condition, symptom, disorder, or disease, or a significant decrease in the baseline activity of a biological activity or process.

As used herein, "treatment" or "treating" refers to prophylaxis of, preventing, suppressing, repressing, reversing, alleviating, ameliorating, or inhibiting the progress of biological process including a disorder or disease, or completely eliminating a disease. A treatment may be either performed in an acute or chronic way. The term "treatment" also refers to reducing the severity of a disease or symptoms associated with such disease prior to affliction with the disease. "Repressing" or "ameliorating" a disease, disorder, or the symptoms thereof involves administering a cell, composition, or compound described herein to a subject after clinical appearance of such disease, disorder, or its symptoms. "Prophylaxis of" or "preventing" a disease, disorder, or the symptoms thereof involves administering a cell, composition, or compound described herein to a subject prior to onset of the disease, disorder, or the symptoms thereof. "Suppressing" a disease or disorder involves administering a cell, composition, or compound described herein to a subject after induction of the disease or disorder thereof but before its clinical appearance or symptoms thereof have manifest. In one embodiment, after diagnosis of a subject being infected with SARS-CoV-2, a variety of treatments may be administered to target the virus, ameliorate symptoms, or provide palliative care.

Coronaviruses (CoVs), are enveloped positive-sense RNA viruses, which are surrounded by crown-shaped, club-like spikes projection on the outer surface. Coronaviruses' spike proteins are glycoproteins that are embedded over the viral envelope. This spike protein attaches to specific cellular receptors and initiates structural changes of spike protein, and causes penetration of cell membranes, which results in the release of the viral nucleocapsid into the cell. These spike proteins determine host trophism. Coronaviruses have a large RNA genome, ranging in size from 26 to 32 kilobases and capable of obtaining distinct ways of replication. Like other RNA viruses, coronaviruses under-go replication of the genome and transcription of mRNAs upon infection. Coronavirus infection in a subject can result in significant and long-term damage of the lungs, leading to possibly sever respiratory issues.

As used herein "SARS-CoV-2" is a beta-coronavirus (Beta-CoV or β-CoV). In particular, SARS-CoV-2 is a Beta-CoV of lineage B. SARS-CoV-2 may also be known as "2019-nCoV" or 2019 novel coronavirus. The disease associated with SARS-CoV-2 is known as COVID-19. Beta-coronaviruses are one of four genera of coronaviruses and are enveloped, positive-sense, single-stranded RNA viruses of zoonotic origin. Beta-coronaviruses mainly infect bats, but they also infect other species like humans, camels, and rabbits. SARS-CoV-2 may be transferable between animals, such as between humans. As used herein "viral transmission" is the process by which viruses spread between host subjects. Transmission occurs from person to person by direct or indirect contact or exposure. Examples of direct contact include, but are not limited to, the exchange of body fluids between a subject infected with the virus and someone else. Indirect contact includes, but is not limited to, exposure to bodily fluid droplets produced by a subject infected by the virus during coughing and/or sneezing. Beta-CoVs may induce fever and respiratory symptoms in humans. The SARS-CoV-2 receptor binding domain (RBD) of the spike protein binds to the human angiotensin-converting enzyme 2 (ACE2) receptor as a means for entering cells.

Diagnosis of SARS-CoV-2 may comprise a positive test for SARS-CoV-2 virus, viral RNA, subject antibodies against SARS-CoV-2 antigens, and/or onset of SARS-CoV-2 symptoms, or combinations thereof. The reagents and method described herein permit the diagnosis of infection of SARS-CoV-2 by reacting with antibodies produced by the subject in response to the SARS-CoV-2 infection. Symptoms of SARS-CoV-2 infection (COVID-19) include, but are not limited to, one or more of the following symptoms: nasal congestion, sore throat, fever, body aches, exhaustion, dry cough, difficulty breathing, or a combination thereof. Subjects at higher risk of developing complications may be immunocompromised (e.g., undergoing cancer treatment, bone marrow or organ transplantation, immune deficiencies, poorly controlled HIV or AIDS, prolonged use of corticosteroids or immune weakening medications), have an underlying medical condition (e.g., diabetes, renal failure, liver disease), are pregnant, are at least 65 years of age, have a chronic lung disease, have a heart disease, or combinations thereof.

Given the urgent need for evaluation of SARS-CoV-2-specific antibodies in a population for individual patients and the currently availabel tests with noted limitations, there is a significant need for rapid, simple, and affordable antibody tests with appropriate specificity and sensitivity. Such tests will allow decentralized testing of patients for SARS-CoV-2-specific antibodies, thus facilitating epidemiological management and vaccination efforts required to manage this pandemic effectively. Described herein is an assay based on (a) recombinant protein(s) that trigger(s) visible hemagglutination instantly in the presence of SARS-CoV-2 antibodies. The data provided herein establish proof of principle for this method.

The methods described herein are based on one or more recombinant fusion proteins containing at least three domains, i.e., a small camelid-derived antibody (nanobody) that binds to Glycophorin A (GYPA) on the surface of red blood cells (RBC) with high affinity, a SARS-CoV-2-specific immunogenic protein, such as the surface glycoprotein receptor "Spike" protein that serves as antigen for Coronavirus-directed antibodies, and an epitope-tag that is used for protein purification. The polypeptides also have an INF-13 secretion sequence at the N-terminus to permit secretion from the expression cells. One embodiment described herein is the "NanoSpike," (SEQ ID NO: 2) which refers to the respective nanobody and SARS-CoV-2 surface glycoprotein receptor "Spike" domains of the fusion protein (FIG. 1; Table 1). As described herein NanoSpike can efficiently be expressed in various mammalian cell lines and binds to the glycophorin protein on the surface of human red blood cells. Importantly, when added to whole blood containing SARS-CoV-2-specific antibodies of subjects infected with or convalescing from SARS-CoV-2, NanoSpike triggers instant hemagglutination that is easily detected by visual observation or other means such as optical density, impedance, microscopy, imaging, or applications developed for this purpose. Other embodiments useful in the assay include "NanoNuc" (SEQ ID NO: 4), "NanoORF8" (SEQ ID NO: 6), "NanoSpikeORF8" (SEQ ID NO: 8), "NanoORF3b"

(SEQ ID NO: 10), and "NanoSpikeORF3b" (SEQ ID NO: 12), which refer to the nanobody and SARS-CoV-2 nucleocapsid, ORF 8, surface glycoprotein receptor binding domain and ORF 8, ORF 3b, and ORF 3b and surface glycoprotein receptor binding domains, respectively. Each of these fusion proteins permits the detection of subject antibodies against these various SARS-CoV-2 antigens. Polypeptide sequences of these constructs are shown in Table 1. The complete SARS-CoV-2 genome is disclosed in SEQ ID NO: 65 (GenBank: MT072688.1). Other SARS-CoV-2 viral polypeptides are potentially useful for alternative embodiments of the diagnostic or control polypeptides described herein.

Also described herein are fusion proteins that can serve as negative or positive controls for the method or assay described herein. In one embodiment, the fusion protein "NanoControl" (SEQ ID NO: 14) can be used as a negative control. NanoControl comprises the Glycophorin A nanobody domain, but no COVID domain. This polypeptide will not react with SARS-CoV-2-specific antibodies of subjects infected with or convalescing from SARS-CoV-2 when added to a sample of the subject's blood. This construct serves as a negative control.

Alternatively, the "NanoLink" (SEQ ID NO: 16) and "NanoTrim" (SEQ ID NO: 18) fusion proteins can be used as positive controls for the method or assay described herein. NanoLink and NanoTrim fusion proteins both contain two repeated SARS-CoV-2-specific nanobody (H11-D4) domains that recognize the receptor binding domain of SARS-CoV-2 spike protein [4]. NanoLink also contains a hinge region of an IgG FC domain (from the Etanercept sequence) which permits dimerization. Similarly, the NanoTrim fusion protein contains a hinge-isoleucine zipper domain which permits trimerization [5]. These control polypeptides also have an INF-β secretion sequence at the N-terminus to permit secretion from the expression cells.

The nanobody region of the NanoLink (SEQ ID NO: 16) and NanoTrim (SEQ ID NO: 18) constructs binds to the SARS-CoV-2 surface glycoprotein receptor biding domain (RBD) of the NanoSpike construct (or the NanoSpikeORF8 or NanoSpikeORF3b constructs, each of which contains the SARS-CoV-2 spike proteins RBD domain) and can cause hemagglutination (in the absence of a subject's anti-SARS-CoV-2 antibodies) and permits a side-by-side comparison of the assay results with assays conducted with NanoNuc (SEQ ID NO: 4), NanoORF8 (SEQ ID NO: 6), NanoSpikeORF8 (SEQ ID NO: 8), NanoORF3b (SEQ ID NO: 10), NanoSpikeORF3b and NanoControl (as a negative control). Collectively, these constructs permit a cross-validated assay that can be used to assess the presence of anti-SARS-CoV-2 antibodies in a subject's blood.

Polypeptide sequences of the NanoSpike, NanoNuc NanoORF8, NanoSpikeORF8, NanoORF3b, NanoSpikeORF3b, NanoControl, NanoLink, and NanoTrim constructs are shown in

TABLE 1

Nucleic acid sequences are provided in the sequence listing
(odd SEQ ID NOs of the even number polypeptide SEQ ID NOs).
Table 1. Polypeptide Constructs NanoSpike (SEQ ID NO: 1-2)
MTNKCLLQIALLLCFSTTALSMGAPQVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVSGGTS
GGGGSGGGGSGGGGSAAARFPNITNLCPFGEVFNATRFASVYAWNRKRISNCVADYSVLYNSASFSTFKCYGVSPT
KLNDLCFTNVYADSFVIRGDEVRQIAPGQTGKIADYNYKLPDDFTGCVIAWNSNNLDSKVGGNYNYLYRLFRKSNL
KPFERDISTEIYQAGSTPCNGVEGFNCYFPLQSYGFQPTNGVGYQPYRVVVLSFELLHAPATVCGPKKSTNLEFGG
GSGGGSGGGSAWSHPQFEKGGGSGGGSGGGSAWSHPQFEK
INF-β Secretion Sequence: Residues 1-22
Linkers: Residues 23-25; 149-170; 377-390
RBC Binding Domain: 26-148
COVID Spike Domain: 171-376
Dual Strep Tag: 391-419

NanoNuc (SEQ ID NO: 3-4)
MTNKCLLQIALLLCFSTTALSMGAPQVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVSGGTS
GGGGSGGGGSGGGGSAAAMSDNGPQNQRNAPRITFGGPSDSTGSNQNGERSGARSKQRRPQGLPNNTASWFTALTQ
HGKEDLKFPRGQGVPINTNSSPDDQIGYYRRATRRIRGGDGKMKDLSPRWYFYYLGTGPEAGLPYGANKDGIIWVA
TEGALNTPKDHIGTRNPANNAAIVLQLPQGTTLPKGFYAEGSRGGSQASSRSSSRSRNSSRNSTPGSSRGTSPARM
AGNGGDAALALLLLDRLNQLESKMSGKGQQQQGQTVTKKSAAEASKKPRQKRTATKAYNVTQAFGRRGPEQTQGNF
GDQELIRQGTDYKHWPQIAQFAPSASAFFGMSRIGMEVTPSGTWLTYTGAIKLDDKDPNFKDQVILLNKHIDAYKT
FPPTEPKKDKKKKADETQALPQRQKKQQTVTLLPAADLDDFSKQLQQSMSSADSTQAEFGGGSGGGSGGGSAWSHP
QFEKGGGSGGGSGGGSAWSHPQFEK
INF-β Secretion Sequence: Residues 1-22
Linkers: Residues 23-25; 149-170; 590-603
RBC Binding Domain: 26-148
COVID Nucleocapsid Domain: 171-589
Dual Strep Tag: 604-632

NanoORF8 (SEQ ID NO: 5-6)
MTNKCLLQIALLLCFSTTALSMGAPQVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVSGGTS
GGGGSGGGGSGGGGSAAAQECSLQSCTQHQPYVVDDPCPIHFYSKWYIRVGARKSAPLIELCVDEAGSKSPIQYID
IGNYTVSCLPFTINCQEPKLGSLVVRCSFYEDFLEYHDVRVVLDFIPRGGGSGGGSGGGSAWSHPQFEKGGGSGGG
SGGSAWSHPQFEK
INF-β Secretion Sequence: Residues 1-22
Linkers: Residues 23-25; 149-170; 274-288
RBC Binding Domain: 26-148
COVID ORF 8 Domain: 171-273
Dual Strep Tag: 289-317

TABLE 1-continued

Nucleic acid sequences are provided in the sequence listing
(odd SEQ ID NOs of the even number polypeptide SEQ ID NOs).
Table 1. Polypeptide Constructs NanoSpikeORF8 (SEQ ID NO: 7-8)
*MTNKCLLQIALLLCFSTTALSM*GAPQVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVSGGTS
GGGGSGGGGSGGGGSAAARFPNITNLCPFGEVFNATRFASVYAWNRKRISNCVADYSVLYNSASFSTFKCYGVSPT
KLNDLCFTNVYADSFVIRGDEVRQIAPGQTGKIADYNYKLPDDFTGCVIAWNSNNLDSKVGGNYNYLRLFRKSNL
KPFERDISTEIYQAGSTPCNGVEGFNCYFPLQSYGFQPTNGVGYQPYRVVVLSFELLHAPATVCGPKKSTNLEFSG
GGGSGGGGSGGGGSAAA░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░IPRGGGSGGGSGGGSAWSHPQFEKGGGSGGGS
GGSAWSHPQFEK
INF-β Secretion Sequence: Residues 1-22
Linkers: Residues 23-25; 149-170; 377-397; 501-515
RBC Binding Domain: 26-148
COVID Spike Domain: 171-376
COVID ORF 8 Domain: 398-500
Dual Strep Tag: 516-544

NanoORF3b (SEQ ID NO: 9-10)
*MTNKCLLQIALLLCFSTTALSM*GAP**QVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVS**GGTS
GGGGSGGGGSGGGGSAAAMAYCWRCTSCCFSERFQNHNPQKEMATSTLQGCSLCLQLAVVVNSLLTPFARCCWPEF
GGGSGGGSGGGSAWSHPQFEKGGGSGGGSGGSAWSHPQFEK
INF-β Secretion Sequence: Residues 1-22
Linkers: Residues 23-25; 149-170; 227-240
RBC Binding Domain: 26-148
COVID ORF 3b Domain: 171-226
Dual Strep Tag: 241-269

NanoSpikeORF3b (SEQ ID NO: 11-12)
*MTNKCLLQIALLLCFSTTALSM*GAP**QVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVS**GGTS
GGGGSGGGGSGGGGSAAARFPNITNLCPFGEVFNATRFASVYAWNRKRISNCVADYSVLYNSASFSTFKCYGVSPT
KLNDLCFTNVYADSFVIRGDEVRQIAPGQTGKIADYNYKLPDDFTGCVIAWNSNNLDSKVGGNYNYLYRLFRKSNL
KPFERDISTEIYQAGSTPCNGVEGFNCYFPLQSYGFQPTNGVGYQPYRVVVLSFELLHAPATVCGPKKSTNLEFSG
GGGSGGGGSGGGGSAAAMAYCWRCTSCCFSERFQNHNPQKEMATSTLQGCSLCLQLAVVVNSLLTPFARCCWPEFG
GGSGGGSGGGSAWSHPQFEKGGGSGGGSGGSAWSHPQFEK
INF-β Secretion Sequence: Residues 1-22
Linkers: Residues 23-25; 149-170; 377-397; 454-467
RBC Binding Domain: 26-148
COVID Spike Domain: 171-376
COVID ORF 3b Domain: 398-453
Dual Strep Tag: 467-496

NanoControl (SEQ ID NO: 13-14)
*MTNKCLLQIALLLCFSTTALSM*GAP**QVQLQESGGGSVQAGGSLRLSCVASGYTDSTYCVGWFRQAPGKEREGVARI
NTTSGRPWYADSVKGRFTISQDNSKNTVYLQMNSLKPEDTAIYYCTLTTANSRGFCSGGYNYKGQGTQVTVS**GEFG
GGSGGGSGGGSAWSHPQFEKGGGSGGGSGGSAWSHPQFEK
INF-β Secretion Sequence: Residues 1-22
Linkers: Residues 23-25; 149-163
RBC Binding Domain: 26-148
Dual Strep Tag: 164-192

NanoLink (SEQ ID NO:16)
*MTNKCLLQIALLLCFSTTALSM*GAP**QVQLVESGGGLMQAGGSLRLSCAVSGRTFSTAAMGWFRQAPGKEREFVAAI
RWSGGSAYYADSVKGRFTISRDKAKNTVYLQMNSLKYEDTAVYYCARTENVRSLLSDYATWPYDYWGQGTQVTVS**G
GGGSGGGGSGGGGSID**QVQLVESGGGLMQAGGSLRLSCAVSGRTFSTAAMGWFRQAPGKEREFVAAIRWSGGSAYY
ADSVKGRFTISRDKAKNTVYLQMNSLKYEDTAVYYCARTENVRSLLSDYATWPYDYWGQGTQVTVS**SGTGGGGSGG
GGSGGGGSGSEPKSCDKTHTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRWQQGNVFSCSVMHEALH
NHYTQKSLSLSPGKPRGGGSGGGSGGGSAAAWSHPQFEKGGGSGGGSGGSAWSHPQFEK
INF-β Secretion Sequence: Residues 1-22
Linkers: Residues 23-25; 152-168; 295-314; 547-562
SARS-CoV-2 Spike RBD specific nanobody (H11-D4): 26-151; 169-294
IgG-FC Dimerization domain: 315-546
Dual Strep Tag: 563-591

TABLE 1-continued Nucleic acid sequences are provided in the sequence listing
(odd SEQ ID NOs of the even number polypeptide SEQ ID NOs).
Table 1. Polypeptide Constructs NanoTrim (SEQ ID NO: 17-18)
MTNKCLLQIALLLCFSTTALSM<u>GAP</u>QVQLVESGGGLMQAGGSLRLSCAVSGRTFSTAAMGWFRQAPGKEREFVAAI
RWSGGSAYYADSVKGRFTISRDKAKNTVYLQMNSLKYEDTAVYYCARTENVRSLLSDYATWPYDYWGQGTQVTVS<u>G
GGGSGGGSGGGGS</u>IDQVQLVESGGGLMQAGGSLRLSCAVSGRTFSTAAMGWFRQAPGKEREFVAAIRWSGGSAYY
ADSVKGRFTISRDKAKNTVYLQMNSLKYEDTAVYYCARTENVRSLLSDYATWPYDYWGQGTQVTVS<u>SGT</u>
<u>PRGGGSGGGSGGGSAA</u><u>AWSHP
QFEKGGGSGGGSGGGSWSHPQFEK</u>
INF-β Secretion Sequence: Residues 1-22
Linkers: Residues 23-25; 152-168; 295-297; 360-375
SARS-CoV-2 Spike RBD specific nanobody (H11-D4): 26-151; 169-294
Hinge-isoleucine zipper domain (trimerization domain): 298-359
Dual Strep Tag: 376-404

Odd number SEQ ID NO are nucleotide sequences; event numbers are polypeptide sequences The fusion proteins listed in Table 1 can be expressed in mammalian cells and particularly in human cell lines. In one embodiment the proteins are expressed in human embryonic kidney 293 cells (HEK 293). In another aspect, the proteins are expressed in Expi293F™ Cells (Thermo Fisher Scientific). The proteins are secreted into the media and are purified using affinity chromatography. In one aspect, the proteins are purified using Strep-Tactin®X (IBA) resin or beads on a column or batch format. The purified proteins were desalted and concentrated. Further polishing steps can be performed using ion exchange, gel filtration, or other chromatographic methods known in the art.

The diagnostic assays described herein require a minimal amount of whole blood (e.g., from a finger prick). Alternatively, subject plasma or serum can be used when combined with human red blood cells (e.g., from the subject or washed human red blood cells of blood group 0). A small amount of blood (e.g., 10-20 μL is typically combined with the test or control solutions (concentration of NanoSpike or other constructs: 20-60 μg/mL) at a ratio of ~1:1 in an appropriate vessel (microfuge tub) or directly on a test card; gently mixed; and the reaction mixture is spread over the test card field (~1 cm² diameter). The test card is rotated manually or with a mechanical rotor at 80-100 rpm for up to about 2-5 minutes and immediately read under direct light. The presence of hemagglutination (aggregation of red blood cells) is a positive result that indicates the presence of subject antibodies against SARS-CoV-2 antigens (e.g., surface glycoprotein, nucleocapsid, ORFS, OR3b, or a combination thereof).

The assay method described herein was validated using 40 COVID19-positive subjects (and 42 control subjects), with 98% sensitivity and 98% specificity. This assay enables simple, rapid, sensitive, specific, and inexpensive diagnosis and identification of subjects with SARS-CoV-2-specific antibodies, either as result of previous infection or successful vaccination. Information provided by this test is be valuable for epidemiological surveillance and decisions related to forthcoming vaccination efforts.

One embodiment described herein is a nucleotide sequence encoding a polypeptide, wherein the polypeptide comprises a human red blood cell binding antibody domain (RBD) and a SARS CoV-2 virus protein domain (CVD). In one aspect, the RBD comprises a glycophorin A-binding nanobody comprising 90-99% identity to SEQ ID NO: 22. In another aspect, the CVD comprises one or more of a spike protein, a nucleocapsid protein, ORF8 protein, ORF3b protein, or envelope protein comprising 90-99% identity to all or a portion of SEQ ID NO: 24, 26, 28, or 30.

In one aspect, the polypeptide has the structure:
SS-GAP-RBD-GL2-CVD-GL3-AFT or
SS-G L1-RBD-G L2-CVD-G L3-CVD-GL4-AFT;
wherein:
SS is a secretion signal domain;
RBD is a glycophorin A-binding nanobody domain;
GAP, GL1, GL2, GL3, and GL4 are linker domains;
CVD is a SARS CoV-2 virus polypeptide domain comprising a spike protein, nucleocapsid protein, ORF8 protein, ORF3b protein, or envelope protein domains; and
AFT is an affinity purification tag sequence.

In another aspect, the SS comprises 90-99% identity to SEQ ID NO: 20. In another aspect, the GAP, GL1, GL2, GL3, or GL4 comprises 90-99% identity to one or more of SEQ ID NO: 38, 40, 42, 44, or 46. In another aspect, the AFT comprises 90-99% identity to one or more of SEQ ID NO: 58, 60, 62, or 64. In another aspect, the nucleotide sequence has 90% to 99% identity to SEQ ID NO: 1, 3, 5, 7, 9, or 11. In another aspect, the nucleotide sequence is one of SEQ ID NO: 1, 3, 5, 7, 9, or 11.

Another embodiment described herein is a polynucleotide vector comprising a nucleotide sequence described herein.

Another embodiment described herein is a cell comprising a polynucleotide vector comprising a nucleotide sequence described herein.

Another embodiment described herein is a polypeptide encoded by a nucleotide sequence described herein.

Another embodiment described herein is a polypeptide encoded by a nucleotide sequence described herein, wherein the polypeptide has 90% to 99% identity to SEQ ID NO: 2, 4, 6, 8, 10, or 12.

Another embodiment described herein is a polypeptide encoded by a nucleotide sequence described herein, wherein the polypeptide is SEQ ID NO: 2, 4, 6, 8, 10, or 12.

Another embodiment described herein is a diagnostic reagent or research tool comprising a polypeptide encoded by the nucleotide sequence described herein.

Another embodiment described herein is a method or means for manufacturing a nucleotide sequence as described herein or a polypeptide encoded by the nucleotide sequence, the process comprising: transforming or transfecting a cell with a nucleic acid comprising the nucleotide sequence; growing the cells; optionally, harvesting the cells and isolating quantities of the nucleotide sequence; inducing expression of a polypeptide encoded by the nucleotide sequence; harvesting the cells; and isolating and purifying the polypeptide.

Another embodiment described herein is a nucleotide sequence or a polypeptide encoded by the nucleotide sequence, each produced by a method or means described herein.

Another embodiment described herein is a nucleotide sequence encoding a diagnostic control polypeptide, wherein the polypeptide comprises: (a) a glycophorin A-binding nanobody domain comprising 90-99% identity to SEQ ID NO: 22; (b) one or more anti-SARS Co-V-2 nanobody domains comprising 90-99% identity to SEQ ID NO: 32 and one or more multimerization domains comprising 90-99% identity to SEQ ID NO: 34 o4 36.

In one aspect, the polypeptides have the structure:

SS-GAP-RBD-GL5-AFT;

SS-GAP-anti-CVD-GL6-anti-CVD-GL7-IgGFC-GL8-AFT; or

SS-GAP-anti-CVD-GL6-anti-CVD-SGT-HIZD-GL8-AFT;

wherein:

SS is a secretion signal domain;

RBD is a glycophorin A-binding nanobody domain;

GAP, GL5, GL6, GL7, GL8, and SGT are linker domains;

Anti-CVD is an anti-SARS CoV-2 surface glycoprotein receptor binding domain nanobody domain;

IgGFC is a human immunoglobulin FC dimerization domain;

HIZD is a Hinge-isoleucine zipper trimerization domain; and

AFT is an affinity purification tag sequence.

In another aspect, the SS comprises 90-99% identity to SEQ ID NO: 20. In another aspect, the GAP, SGT, GL5, GL6, GL7, or GL8 comprises 90-99% identity to one or more of SEQ ID NO: 38, 48, 50, 52, 54, or 56. In another aspect, the AFT comprises 90-99% identity to one or more of SEQ ID NO: 58, 60, 62, or 64. In another aspect, the nucleotide sequence has 90% to 99% identity to SEQ ID NO: 13, 15, or 17. In another aspect, the nucleotide sequence is one of SEQ ID NO: 13, 15, or 17.

Another embodiment described herein is a polynucleotide vector comprising a nucleotide sequence encoding a diagnostic control polypeptide as described herein.

Another embodiment described herein is a cell comprising a polynucleotide vector comprising a nucleotide sequence encoding a diagnostic control polypeptide as described herein.

Another embodiment described herein is a diagnostic control polypeptide as described herein.

Another embodiment described herein is a diagnostic control polypeptide having 90% to 99% identity to SEQ ID NO: 14, 16, or 18.

Another embodiment described herein is a diagnostic control polypeptide having the polypeptide sequence of SEQ ID NO: 14, 16, or 18.

Another embodiment described herein is a diagnostic reagent or research tool comprising a polypeptide encoded by a nucleotide sequence described herein.

Another embodiment described herein is a diagnostic or control polypeptide comprising the amino acid sequence of SEQ ID NO: 2, 4, 6, 8, 10, 12, 14, 16, or 18.

Another embodiment described herein is a method for evaluating whether a subject is infected or has been infected with SARS-CoV-2, the method comprising: (a) providing a sample of a biological fluid from a subject in need of diagnosis; (b) combining the biological fluid with a diagnostic polypeptide comprising 90 to 99% identity to the amino acid sequence of SEQ ID NO: 2, 4, 6, 8, 10, 12 to form a subject sample; (c) optionally, combining a negative control reagent or a positive control polypeptide comprising 90 to 95% identity to the amino acid sequence of SEQ ID NO: 14 (negative control) or SEQ ID NO: 16 or 18 (positive controls), with the biological fluid and a diagnostic polypeptide comprising 90 to 99% identity to the amino acid sequence of SEQ ID NO: 2, 10, or 12 to form one or more control samples; (d) permitting the subject sample and control samples to incubate for a period of time; (e) evaluating the results by visualization, imaging, optical density, impedance, or microscopy; and (f) optionally, comparing the subject sample and control samples to validate the subject sample results; wherein the presence of hemagglutination in the subject sample is a positive diagnostic indication of SARS-CoV-2 infection, and the absence of hemagglutination in the subject sample is a negative diagnostic indication of SARS-CoV-2 infection. In one aspect, the biological fluid is whole blood, plasma, or serum. In another aspect, when the biological fluid is plasma or serum, washed human red blood cells of blood group 0 are combined with the subject sample and the diagnostic or control polypeptides in steps (b) or (c). In another aspect, wherein the diagnostic or control polypeptides have a concentration of about 10 μg/mL to about 100 μg/mL. In another aspect, the subject sample and/or control samples in steps (b) and/or (c) are dispensed on a test card, glass slide, microtiter plate, or other substrate prior to step (d). In another aspect, when the subject sample has a positive diagnostic indication of SARS-CoV-2 infection, the method further comprises: (g) administering one or more therapeutics or treatments to the subject.

Another embodiment described herein is a kit comprising: (a) one or more diagnostic or control polypeptides comprising the amino acid sequence of SEQ ID NO: 2, 4, 6, 8, 10, 12, 14, 16, or 18; (b) a test substrate; and (c) optionally, a label or instructions for use. In one aspect, the kit further comprises one or more of alcohol saturated towelettes; finger prick lances, capillaries, or gloves.

Another embodiment described herein is the use of a polypeptide comprising 90 to 99% identity to the amino acid sequence of SEQ ID NO: 2, 4, 6, 8, 10, 12, 14, 16, or 18 for the diagnosis of SARS-CoV-2 in a subject in need of diagnosis thereof.

Another embodiment described herein is a polynucleotide vector comprising one or more nucleotide sequences described herein. In one aspect, the nucleotide sequence comprises 85% to 100% identity to SEQ ID NO: 1, 3, 5, 7, 9, 11, 13, 15, or 17 and encodes a polypeptide having 85% to 100% identity to SEQ ID NO: 2, 4, 6, 8, 10, 12, 14, 16, or 18.

Another embodiment described herein is a cell comprising one or more nucleotide sequences described herein or a polynucleotide vector described herein encoding one or more polypeptides. In one aspect, the nucleotide sequence has 85% to 100% identity to SEQ ID NO: 1, 3, 5, 7, 9, 11, 13, 15, or 17 and the encoded polypeptide has 85% to 100% identity to SEQ ID NO: 2, 4, 6, 8, 10, 12, 14, 16, or 18.

Another embodiment is a diagnostic or control polypeptide encoded by a nucleotide sequence described herein. In one aspect, the nucleotide sequence has 85% to 100% identity to SEQ ID NO: 1, 3, 5, 7, 9, 11, 13, 15, or 17 and the encoded polypeptide has 85% to 100% identity to SEQ ID NO: 2, 4, 6, 8, 10, 12, 14, 16, or 18. In another aspect, the diagnostic polypeptide is selected from SEQ ID NO: 2, 4, 6, 8, 10, or 12. In another aspect the control polypeptide is selected from SEQ ID NO: 14, 16, or 18

Another embodiment described herein is a process for manufacturing one or more of the nucleotide sequence described herein or a polypeptide encoded by the nucleotide sequence described herein, the process comprising: transforming or transfecting a cell with a nucleic acid comprising a nucleotide sequence described herein; growing the cells; optionally isolating additional quantities of a nucleotide sequence described herein; inducing expression of a polypeptide encoded by a nucleotide sequence of described herein; isolating the polypeptide encoded by a nucleotide described herein.

Another embodiment described herein is a means for manufacturing one or more of the nucleotide sequences described herein or a polypeptide encoded by a nucleotide sequence described herein, the process comprising: transforming or transfecting a cell with a nucleic acid comprising a nucleotide sequence described herein; growing the cells; optionally isolating additional quantities of a nucleotide sequence described herein; inducing expression of a polypeptide encoded by a nucleotide sequence of described herein; isolating the polypeptide encoded by a nucleotide described herein.

Another embodiment described herein is a nucleotide sequence or a polypeptide encoded by the nucleotide sequence produced by the method or the means described herein Another embodiment described herein is the use of an effective amount of a polypeptide encoded by one or more of the nucleotide sequences described herein having 85% to 100% identity to SEQ ID NO: 1, 3, 5, 7, 9, 11, 13, 15, 17.

Another embodiment described herein is a research tool comprising a polypeptide encoded by a nucleotide sequence described herein.

Another embodiment described herein is an analytical reagent comprising a polypeptide encoded by a nucleotide sequence described herein.

The polynucleotides described herein include variants that have substitutions, deletions, and/or additions that can involve one or more nucleotides. The variants can be altered in coding regions, non-coding regions, or both. Alterations in the coding regions can produce conservative or non-conservative amino acid substitutions, deletions, or additions. Especially preferred among these are silent substitutions, additions, and deletions, which do not alter the properties and activities of the binding.

Further embodiments described herein include nucleic acid molecules comprising polynucleotides having nucleotide sequences about 50%, 55%, 60%, 65%, 70%, 75%, 80%, 85%, 90%, 91%, 92%, 93%, 94%, 95%, 96%, 97%, 98%, or 99% identical, and more preferably at least about 90-99% or 100% identical to (a) nucleotide sequences, or degenerate, homologous, or codon-optimized variants thereof, encoding polypeptides having the amino acid sequences in SEQ ID NO: 2, 4, 6, 8, 10, 12, 14, 16, or 18 (b) nucleotide sequences, or degenerate, homologous, or codon-optimized variants thereof, encoding polypeptides having the amino acid sequences in SEQ ID NO: 2, 4, 6, 8, 10, 12, 14, 16, or 18; and (c) nucleotide sequences capable of hybridizing to the complement of any of the nucleotide sequences in (a) or (b) above and capable of expressing functional polypeptides of amino acid sequences in SEQ ID NO: 2, 4, 6, 8, 10, 12, 14, 16, or 18.

By a polynucleotide having a nucleotide sequence at least, for example, 90-99% "identical" to a reference nucleotide sequence encoding a polypeptide of SEQ ID NO: 2, 4, 6, 8, 10, 12, 14, 16, or 18 is intended that the nucleotide sequence encoding the polynucleotide be identical to the reference sequence except that the polynucleotide sequence can include up to about 10 to 1 point mutations, additions, or deletions per each 100 nucleotides of the reference nucleotide sequence encoding a polypeptide of SEQ ID NO: 2, 4, 6, 8, 10, 12, 14, 16, or 18.

In other words, to obtain a polynucleotide having a nucleotide sequence about at least 90-99% identical to a reference nucleotide sequence, up to 10% of the nucleotides in the reference sequence can be deleted, added, or substituted, with another nucleotide, or a number of nucleotides up to 10% of the total nucleotides in the reference sequence can be inserted into the reference sequence. These mutations of the reference sequence can occur at the 5'- or 3'-terminal positions of the reference nucleotide sequence or anywhere between those terminal positions, interspersed either individually among nucleotides in the reference sequence or in one or more contiguous groups within the reference sequence. The same is applicable to polypeptide sequences about at least 90-99% identical to a reference polypeptide sequence.

As noted above, two or more polynucleotide sequences can be compared by determining their percent identity. Two or more amino acid sequences likewise can be compared by determining their percent identity. The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2: 4 82-489 (1981). This algorithm can be extended to use with peptide sequences using the scoring matrix developed by Dayhoff, Atlas of Protein Sequences and Structure, M. O. Dayhoff ed., 5 suppl. 3: 353-358, National Biomedical Research Foundation, Washington, D.C., USA, and normalized by Gribskov, Nucl. Acids Res. 14(6): 6745-6763 (1986).

For example, due to the degeneracy of the genetic code, one having ordinary skill in the art will recognize that a large number of the nucleic acid molecules having a sequence at least 50%, 55%, 60%, 65%, 70%, 75%, 80%, 85%, 90%, 91%, 92%, 93%, 94%, 95%, 96%, 97%, 98%, 99%, or 100% identical to the nucleic acid sequence shown in SEQ ID NO: 1, 3, 5, 7, 9, 11, 13, 15, or 17, or degenerate, homologous, or codon-optimized variants thereof, will encode a polypeptide having a sequence at least 50%, 55%, 60%, 65%, 70%, 75%, 80%, 85%, 90%, 91%, 92%, 93%, 94%, 95%, 96%, 97%, 98%, 99%, or 100% identical to the polypeptide sequence shown in SEQ ID NO: 2, 4, 6, 8, 10, 12, 14, 16, or 18.

The polynucleotides described herein include those encoding mutations, variations, substitutions, additions, deletions, and particular examples of the polypeptides described herein. For example, guidance concerning how to make phenotypically silent amino acid substitutions is provided in Bowie, J. U. et al., "Deciphering the Message in Protein Sequences: Tolerance to Amino Acid Substitutions," Science 247: 1306-1310 (1990), wherein the authors indicate that proteins are surprisingly tolerant of amino acid substitutions.

Thus, fragments, derivatives, or analogs of the polypeptides of SEQ ID NO: 2, 4, 6, 8, 10, 12, 14, 16, or 18 can be (i) ones in which one or more of the amino acid residues (e.g., 1, 2, 3, 4, 5, 7, 8, 9, 10, 11, 12, 13, 14, 15, 16, 17, 18, 19, 20, 25, 30, 35, 40, 45, or 50 residues, or even more) are substituted with a conserved or non-conserved amino acid residue (preferably a conserved amino acid residue). Such substituted amino acid residues may or may not be one encoded by the genetic code, or (ii) ones in which one or more of the amino acid residues includes a substituent group (e.g., 1, 2, 3, 4, 5, 7, 8, 9, 10, 15, 20, 25, 30, 35, 40, 45, or 50 residues or even more), or (iii) ones in which the mature polypeptide is fused with another polypeptide or compound, such as a compound to increase the half-life of the polypeptide (for example, polyethylene glycol), or (iv) ones in which the additional amino acids are fused to the mature polypeptide, such as an IgG Fc fusion region peptide or leader or secretory sequence or a sequence which is employed for purification of the mature polypeptide or a proprotein sequence. Such fragments, derivatives, and analogs are deemed to be within the scope of those skilled in the art from the teachings herein.

In addition, fragments, derivatives, or analogs of the polypeptides of SEQ ID NO: 2, 4, 6, 8, 10, 12, 14, 16, or 18 can be substituted with one or more conserved or non-conserved amino acid residue (preferably a conserved amino acid residue). In some cases these polypeptides, fragments, derivatives, or analogs thereof will have a polypeptide sequence at least 50%, 55%, 60%, 65%, 70%, 75%, 80%, 85%, 90%, 91%, 92%, 93%, 94%, 95%, 96%, 97%, 98%, 99% or 100% identical to the polypeptide sequence shown in SEQ ID NO: 2, 4, 6, 8, 10, 12, 14, 16, or 18 and will comprise functional or non-functional proteins or enzymes. Similarly, additions or deletions to the polypeptides can be made either at the N- or C-termini or within non-conserved regions of the polypeptide (which are assumed to be non-critical because they have not been photogenically conserved).

As described herein, in many cases the amino acid substitutions, mutations, additions, or deletions are preferably of a minor nature, such as conservative amino acid substitutions that do not significantly affect the folding or activity of the protein or additions or deletions to the N- or C-termini. Of course, the number of amino acid substitutions, additions, or deletions a skilled artisan would make depends on many factors, including those described herein. Generally, the number of substitutions, additions, or deletions for any given polypeptide will not be more than about 100, 90, 80, 70, 60, 50, 40, 30, 25, 20, 19, 18, 17, 16, 15, 14, 13, 12, 11, 10, 9, 8, 7, 5, 6, 4, 3, 2, or 1.

It will be apparent to one of ordinary skill in the relevant art that suitable modifications and adaptations to the compositions, formulations, methods, processes, apparata, assemblies, and applications described herein can be made without departing from the scope of any embodiments or aspects thereof. The compositions, apparata, assemblies, and methods provided are exemplary and are not intended to limit the scope of any of the disclosed embodiments. All the various embodiments, aspects, and options disclosed herein can be combined in any variations or iterations. The scope of the compositions, formulations, methods, apparata, assemblies, and processes described herein include all actual or potential combinations of embodiments, aspects, options, examples, and preferences described herein. The compositions, formulations, apparata, assemblies, or methods described herein may omit any component or step, substitute any component or step disclosed herein, or include any component or step disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. All patents and publications cited herein are incorporated by reference herein for the specific teachings thereof.

REFERENCES

1. Kontou et al., "Antibody Tests in Detecting SARS-CoV-2 Infection: A Meta-Analysis," *Diagnostics* (Basel) 10(5): 319 (2020).
2. Gudbjartsson et al., "Humoral Immune Response to SARS-CoV-2 in Iceland," *N. Engl. J. Med.* 383(18):1724-1734 (2020).
3. Hachim et al., "ORF8 and ORF3b antibodies are accurate serological markers of early and late SARS-CoV-2 infection," *Nat. Immunol.* 21(10):1293-1301 (2020).
4. Huo et al., "Neutralizing nanobodies bind SARS-CoV-2 spike RBD and block interaction with ACE2," *Nat. Struct. Mol. Biol.* 27(9): 846-854 (2020).
5. Tillib et al., "Formatted single-domain antibodies can protect mice against infection with influenza virus (H5N2)," *Antiviral Res.* 97(3):245-254 (2013).
6. Redecke et al., "Hematopoietic progenitor cell lines with myeloid and lymphoid potential," *Nat. Methods* 10(8): 795-803 (2013).
7. Lee et al., "Production of specific antibodies against SARS-coronavirus nucleocapsid protein without cross reactivity with human coronaviruses 229E and OC43," *J. Vet. Sci.* 11(2): 165-167 (2010).
8. Lee et al., "Detection of antibodies against SARS-Coronavirus using recombinant truncated nucleocapsid proteins by ELISA," *J. Microbiol. Biotechnol.* 18(10): 1717-1721 (2008).
9. Dutta et al., "Search for potential target site of nucleocapsid gene for the design of an epitope-based SARS DNA vaccine," *Immunol. Let.* 118(1): 65-71 (2008).
10. Gupta and Chaudhary, "Whole-blood agglutination assay for on-site detection of human immunodeficiency virus infection," *J. Clin. Microbiol.* 41(7): 2814-2821 (2003).
11. Kemp et al., "Autologous red cell agglutination assay for HIV-1 antibodies: simplified test with whole blood," *Science* 241(4871):1352-1354 (1988).
12. Gupta and Chaudhary, "Expression, purification, and characterization of an anti-RBCFab-p24 fusion protein for hemagglutination-based rapid detection of antibodies to HIV in whole blood," *Protein Expr. Purif.* 26(1): 162-170 (2002).
13. Habib et al., "V(H)H (nanobody) directed against human glycophorin A: a tool for autologous red cell agglutination assays," *Anal. Biochem.* 438(1): 82-89 (2013).
14. Tai et al., "Characterization of the receptor-binding domain (RBD) of 2019 novel coronavirus: implication for development of RBD protein as a viral attachment inhibitor and vaccine," *Cell. Mol. Immunol.* 17(6): 613-620 (2020).
15. Ravichandran et al., "Antibody signature induced by SARS-CoV-2 spike protein immunogens in rabbits," *Sci. Transl. Med.* 12(550): eabc3539 (2020).
16. Grzelak et al., "A comparison of four serological assays for detecting anti-SARS-CoV-2 antibodies in human serum samples from different populations," *Sci. Transl. Med.* 12(559): eabc3103 (2020).

EXAMPLES

Example 1

Plasmids

DNA encoding expressed proteins was synthesized by commercial suppliers (Thermo Fisher Scientific/Invitrogen, Synbio, Biomatic) and cloned by standard molecular biology methods into the mammalian expression vector pcDNA3.1(+) (Invitrogen). All coding sequences were confirmed by Sanger sequencing.

Protein Expression

All proteins were expressed in Expi293F™ cells (Thermo Fisher Scientific) using the ExpiFectamine™ 293 Transfection Kit following the manufacturer's instructions (Thermo Fisher Scientific). In brief, cells were cultured at 37° C. and 8% $CO_2$ in 25 mL of Expi293 expression medium (Thermo Fisher Scientific) in 125 mL bottles on a 25 mm orbital shaker (120 rpm) until reaching a density of 4.5-5.5×$10^6$/mL. Cells were seeded at 3×$10^6$/mL in 25 mL per 125 mL flasks for transfection. 25 μg of DNA and 80 μL of Epifectamine was added to 1.5 mL and 1.4 mL Opti-Plex complexation buffer (Thermo Fisher Scientific), respectively. After a 3-5 min incubation at room temperature (RT), the two solutions were combined, gently mixed, incubated for 15 min at RT and added dropwise to cells. After overnight culture, Epifectamine transfection enhancer 1 (150 μL) and Epifectamine transfection enhancer 2 (1.5 mL) was added, and cell suspensions were harvested two days later.

Protein Purification

Cell suspensions were centrifuged at 450 g for 5 min and protein-containing supernatant was cleared using 0.2 μm filter bottles. To remove biotin (interfering with affinity purification), 3 mL of 10× buffer W (1M Tris-HCl pH 8.0, 1.5 M NaCl, 10 mM EDTA) was added to the supernatant along with 600 μL of BioLock solution (IBA), followed by ultracentrifugation at 20,000×g for 20 min at 4° C. The resulting supernatant was loaded on columns containing 700 μL of washed Strep-Tactin® XT matrix (IBA). The columns were rinsed five times with 1 mL ice-cold PBS, proteins were eluted with 3×500 μL of buffer BXT (IBA), concentrated on Amicon Ultra3k concentration columns (3 kD cutoff) at 14,000×g at 4° C. and desalted by centrifugation at 1500× g for 2 min using TBS-equilibrated Zeba Spin desalting columns (0.5 mL, 7 k MWCO, Thermo Fisher Scientific). 3-10 μg of each purified proteins was analyzed by SDS PAGE and Sypro Ruby staining (Thermo Fisher Scientific).

Example 2

Design, Expression and Purification of Recombinant Proteins

Due to the known robustness of nanobodies and the availability of required sequence information. Methodologically, a modified form of the IH4 nanobody (IH4vs2) was fused to the receptor-binding domain of the Spike protein of SARS-CoV-2, which has been shown in various analyses to represent a highly immunogenic region [6-8]. Mammalian cells were used for protein expression. The SARS Co-V-2 surface "spike" glycoprotein is physiologically targeted to the secretory pathway, which is likely required for proper protein folding and accompanied by glycosylation, which in turn may be relevant for the antibody response and thus test specificity [9]. To allow for proper targeting to the secretory pathway, a secretion signal derived from interferon-β was fused to the N-terminus of the fusion protein (FIG. 1). A tandem Strep-tag was fused to the C-terminus to allow for efficient one-step protein purification. Flexible glycine-serine-containing linkers were placed between the functional units of the fusion protein to avoid interference of the different domains. A similar protein lacking the Spike RBD was cloned as negative control (FIG. 1). The proteins were expressed first in small scale, then in larger scale experiments in either ExpiCho-S™ or Expi293F™ cells (Thermo Fisher Scientific), both of which are optimized for high density growth in suspension and used extensively in the pharmaceutical industry. As shown for experiments based on Expi293F™ cells, protein expression and Strep-tag-based one-step purification was very efficient, resulting in virtually homogenous protein preparations for both the NanoSpike and the NanoControl protein (FIG. 3-5). Around 2 mg of protein were obtained from 30 mL of cell culture, reflecting a highly efficient process.

Example 3

Functional Activity of Recombinant Proteins in Hemagglutination Assays

To determine whether the NanoSpike protein binds to red blood cells, different concentrations of the NanoSpike protein were incubated with human whole blood, followed by visualization using FITC-conjugated anti-Strep-tag antibodies and flow cytometry (FIG. 6-7). As expected, NanoSpike bound efficiently and in a concentration-dependent manner to RBC.

In order to determine if NanoSpike cross-linking induces visible hemagglutination of RBC, the NanoSpike protein was added to a small drop (10 μL) of human whole blood, either in the absence of antibodies, anti-Strep antibodies (crosslinking) or anti-CD4 antibodies (negative control). Indeed, in the presence of NanoSpike, anti-Strep antibodies induced instant hemagglutination in a concentration-dependent way. anti-Strep antibodies alone or anti-Strep antibodies in the presence of αCD4 antibodies showed no effect, demonstrating specificity. Given that the anti-Strep antibodies is a monoclonal IgG1 antibodies, these data also suggest that the valency of IgG is sufficient to trigger agglutination (as opposed to the higher valency of IgM).

To obtain proof of principle for NanoSpike activity in the presence of physiological αSpike antibodies, whole blood of a confirmed COVID19 patient was combined with NanoSpike or NanoControl protein. Indeed, similar to the anti-Strep antibody-treated samples, NanoSpike mediated instant hemagglutination. NanoSpike expressed from ExpiCho-S and Expi293F cells showed the same activity. As the protein amount obtained from Expi293F cells was slightly higher, these cells were used for further expression. Of note, NanoControl protein did not exhibit any agglutination, even during extended periods of time, suggesting that agglutination is solely governed by the Spike RBD moiety, respectively antibodies directed against Spike. This experiment was confirmed with two patients two weeks after being tested PCR-positive (not shown).

Example 4

To further substantiate the initial testing described above, five plasma samples from COVID19 patients with ELISA-positive αSARS-CoV-2 antibody titers was tested, along with five confirmed antibody-negative control samples. Plasma was used for these assays because it was immediately available from frozen stocks maintained at a reference laboratory (ARUP). For these assays, washed RBC from a healthy donor were used and combined NanoSpike (or NanoControl) protein along with plasma from test samples. All COVID19-positive samples showed immediate hemagglutination in the presence of NanoSpike, but not the NanoControl protein, while all COVID19-negative samples remained without detectable hemagglutination. Even though blood plasma is not the intended major type of material typically used for the assay (i.e., the preferred sample is finger stick capillary blood), it has the advantage that it can be titrated independent of RBC and was useful to assess the sensitivity of the assay at different antibodies concentrations. This facilitated the testing and optimization of other viral proteins fused to the Nanobody (e.g., NanoNuc, NanoORF8, NanoORF3b, NanoSpikeORF8, NanoSpikeORF3b).

Example 5

The assay was further validated using serum from patients which had been tested with an FDA-approved Spike-ELISA (Euroimmun). Forty ELISA-positive and forty-two ELISA-negative cases were enrolled. NanoControl, NanoSpike and NanoLink recombinant proteins (30 µg/mL) were added to washed RBC along with the subject serum and the presence or absence of hemagglutination was observed and documented (FIG. 8.). The number of cases that were correctly identified by the NanoSpike test (in a blinded analysis) are shown in Table 2.

Based on these assays, specificity, and sensitivity were calculated according to standard formulas: Sensitivity=number of true test-positive divided by (number of true test-positive plus number of false negatives). Specificity=number of true test-negatives divided by (number of true test-negatives plus number of false positives).

TABLE 2

NanoSpike identifies sero-positive COVID19 patients with high specificity and sensitivity.

|  | Euroimmune (Spike) | ELISA (82 patients) |
|---|---|---|
| ELISA (Number of cases) | 40 (test-positive) | 42 (test-negative) |
| NanoSpike Agglutination (number of correct identifications) | 39 | 41 |
| NanoSpike Agglutination (number of incorrect identifications) | 1 | 1 |
| Specificity (%) |  | 98 |
| Sensitivity (%) |  | 98 |

Example 6

NanoSpike Assay Methodology
Assay Reagents/Components:
Subject sample: blood, serum, plasma, or other bilogical fluid sample (described below)
NanoSpike, NanoNuc, NanoORF8, NanoORF3b, NanoSpikeORF8, NanoSpikeORF3b, or other Nanobody (IH4vs2)-conjugated proteins (20-60 µg/mL): glycophorin targeting nanobody conjugated to SARS-CoV-2 proteins
NanoControl (20-60 µg/mL): Negative control, glycophorin targeting nanobody alone
NanoLink (20-60 µg/mL): Positive control, test substance (20-60 µg/mL); SARS-CoV-2 Spike-targeting nanobody construct (based on the H11-D4 nanobody) fused to the Hinge-FC part of IgG1 protein. This compound mimics dimerizing anti-Spike antibodies.
NanoTrim (20-60 µg/mL):Positive control, test substance (20-60 µg/mL), SARS-CoV-2 Spike-targeting nanobody construct (based on the H11-D4 nanobody) fused to trimerizing Hinge-isoleucine zipper domain. This compound mimics multimerizing anti-Spike antibodies.
Miscellaneous Items: Test cards; gloves; alcohol (70% isopropanol) towelettes; finger prick lances; bandages; pipets, pipet tips, microfuge tubes, magnifying means, bright light; biohazard disposal receptacle; etc.
Specimen Collection
Total Blood
Blood was collected in vacutainers or collection tubes containing EDTA by venipuncture or finger-stick.
Plasma
Blood was collected in vacutainers containing EDTA by venipuncture and plasma was separated by centrifugation.
Serum
Blood was collected in vacutainers containing no anticoagulants by venipuncture and plasma was separated by centrifugation after the blood had clotted.
Test Procedures (at Room Temperature, ~25° C.):
Total Blood
A small amount of blood, e.g., 10-20 µL, was combined with test or control solutions at a ratio of ~1:1, gently mixed, and the reaction mixture was spread over the test card field (~1 cm$^2$ diameter).
The test card was rotated manually or with a mechanical rotor at 80-100 rpm for 2-5 minutes and immediately read under direct light.
The presence of hemagglutination was a positive result. The absence of hemagglutination was a negative result. Results were compared to positive and/or negative control samples using the same subject sample.
Plasma and Serum
A small amount of plasma or serum, e.g. 5-10 µL, was combined with a small amount, e.g., 5-10 µL, of washed human red blood cells (RBC) of blood group 0. RBCs can be used pure or diluted with PBS up to 1:10.
The test or control solutions are added to the plasma/serum/RBC mixture at a ratio of 1:1, gently mixed and the reaction mixture was spread over the test field (~1 cm$^2$ diameter).
The test card was rotated manually or with a mechanical rotor at 80-100 rpm for 2-5 minutes and immediately read under direct light.
The presence of hemagglutination was a positive result. The absence of hemagglutination was a negative result. Results were compared to positive and/or negative control samples using the same subject sample.
Hemagglutination can be visually read on cardboard test cards or on glass slides. Alternative assay systems include the use of microtiter plates, gel immunodiffusion, ouchterlony, or automated systems that can detect agglutination, e.g., by still or video imaging, optical density, impedance, microscopy, or using specific applications developed for this purpose.
Exemplary Cost Analysis
One advantage of the assays described herein is their simplicity and low costs. Based on regular prices (not wholesale), estimated material costs for protein expression and purification amount to ~$0.019/assay, and additional equipment (also regular retail prices), including lancets, capillaries, and ethanol wipes amount to ~$0.30/assay. While overhead costs for personnel and logistics need to be accounted, it is expected that up-scaled protein production and wholesale prizes for equipment will further reduce production costs.

What is claimed:

1. A polypeptide comprising a human red blood cell binding antibody domain (RBD) comprising a glycophorin A-binding nanobody comprising 90-99% identity to the polypeptide sequence of SEQ ID NO: 22 and a SARS CoV-2 virus protein domain (CVD).

2. The polypeptide of claim 1, wherein the RBD comprises a glycophorin A-binding nanobody having a polypeptide sequence of SEQ ID NO: 22.

3. The polypeptide of claim 1, wherein the CVD comprises one or more of a spike protein comprising 90-99% identity to all or a portion of the polypeptide sequence of SEQ ID NO: 24.

4. The polypeptide of claim 3, wherein the polypeptide has the structure:
SS-GAP-RBD-GL2-CVD-GL3-AFT
wherein:
SS is a secretion signal domain;
RBD is a glycophorin A-binding nanobody domain;
GAP is a linker domain;
CVD is a SARS CoV-2 virus polypeptide domain comprising a spike protein domain; and
AFT is an affinity purification tag sequence.

5. The polypeptide of claim 4, wherein the SS comprises 90-99% identity to SEQ ID NO: 20.

6. The polypeptide of claim 4, wherein the GAP domain comprises 90-99% identity to SEQ ID NO: 38.

7. The polypeptide of claim 4, wherein the affinity purification tag (AFT) comprises 90-99% identity to SEQ ID NO: 60.

8. The polypeptide of claim 1, wherein the polypeptide is encoded by a nucleotide sequence having 90% to 99% identity to SEQ ID NO: 1.

9. The polypeptide of claim 1, wherein the polypeptide is encoded by a nucleotide sequence of SEQ ID NO: 1.

10. A polynucleotide vector comprising a nucleotide sequence of claim 9.

11. A cell comprising a polynucleotide vector of claim 10.

12. The polypeptide of claim 1, wherein the polypeptide has 90% to 99% identity to SEQ ID NO: 2.

13. A method for evaluating whether a subject is infected or has been infected with SARS-CoV-2, the method comprising:
(a) providing a sample of a biological fluid from a subject in need of diagnosis;
(b) combining the biological fluid with a polypeptide of claim 12;
(c) permitting the subject sample and control samples to incubate for a period of time;
(d) evaluating the results by visualization, imaging, optical density, impedance, or microscopy; and
wherein the presence of hemagglutination in the subject sample is a positive diagnostic indication of SARS-CoV-2 infection, and the absence of hemagglutination in the subject sample is a negative diagnostic indication of SARS-CoV-2 infection.

14. The method of claim 13, wherein the biological fluid is whole blood, plasma, or serum.

15. The method of claim 14, wherein when the biological fluid is plasma or serum, washed human red blood cells of blood group O are combined with the subject sample and the diagnostic or control polypeptides in steps (b) or (c).

16. The method of claim 13, wherein the diagnostic or control polypeptides have a concentration of about 10 μg/mL to about 100 μg/mL.

17. The method of claim 13, wherein the subject sample in step (b) is dispensed on a test card, glass slide, microtiter plate, or other substrate prior to step (c).

18. The method of claim 13, wherein when the subject sample has a positive diagnostic indication of SARS-CoV-2 infection, the method further comprises:
(g) administering one or more therapeutics or treatments to the subject.

19. A kit comprising:
(a) a diagnostic polypeptide comprising the amino acid sequence of SEQ ID NO: 2;
(b) a test substrate; and
(c) optionally, a label or instructions for use.

20. The kit of claim 19, further comprising one or more of alcohol saturated towelettes; finger prick lances, capillaries, or gloves.

* * * * *

SEQUENCE LISTING

<160> NUMBER OF SEQ ID NOS: 67

<210> SEQ ID NO 1
<211> LENGTH: 1260
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1260)

<400> SEQUENCE: 1

```
atg acc aac aag tgc ctg ctg cag att gcc ctg ctg ctg tgc ttc agc      48
Met Thr Asn Lys Cys Leu Leu Gln Ile Ala Leu Leu Leu Cys Phe Ser
1               5                   10                  15 aca aca gcc ctg tct atg ggc gcg cct caa gtt cag ctt caa gaa tct      96
Thr Thr Ala Leu Ser Met Gly Ala Pro Gln Val Gln Leu Gln Glu Ser
            20                  25                  30 ggc ggc gga agc gtt cag gct ggc gga tct ctg aga ctg agc tgt gtg     144
Gly Gly Gly Ser Val Gln Ala Gly Gly Ser Leu Arg Leu Ser Cys Val
        35                  40                  45 gcc agc ggc tac acc gat agc aca tac tgc gtc ggc tgg ttc aga cag     192
Ala Ser Gly Tyr Thr Asp Ser Thr Tyr Cys Val Gly Trp Phe Arg Gln
    50                  55                  60 gcc cct ggc aaa gag aga gag ggc gtc gcc aga atc aac acc atc agc     240
Ala Pro Gly Lys Glu Arg Glu Gly Val Ala Arg Ile Asn Thr Ile Ser
65                  70                  75                  80 ggc aga cct tgg tac gcc gac tct gtg aag ggc aga ttc aca atc agc     288
Gly Arg Pro Trp Tyr Ala Asp Ser Val Lys Gly Arg Phe Thr Ile Ser
                85                  90                  95 cag gac aac agc aag aac acc gtg tac ctg cag atg aac agc ctg aag     336
Gln Asp Asn Ser Lys Asn Thr Val Tyr Leu Gln Met Asn Ser Leu Lys
            100                 105                 110 cct gag gac acc gcc atc tac tac tgc acc ctg acc acc gcc aac agc     384
Pro Glu Asp Thr Ala Ile Tyr Tyr Cys Thr Leu Thr Thr Ala Asn Ser
        115                 120                 125 aga ggc ttt tgt tcc ggc ggc tac aac tac aaa ggc cag ggc acc caa     432
Arg Gly Phe Cys Ser Gly Gly Tyr Asn Tyr Lys Gly Gln Gly Thr Gln
    130                 135                 140 gtg acc gtg tct ggt ggt acc agc gga ggc gga gga tca ggt ggc gga     480
Val Thr Val Ser Gly Gly Thr Ser Gly Gly Gly Gly Ser Gly Gly Gly
145                 150                 155                 160 ggt agt ggt ggt ggc ggt agc gcg gcc gct aga ttc ccc aac atc acc     528
Gly Ser Gly Gly Gly Gly Ser Ala Ala Ala Arg Phe Pro Asn Ile Thr
                165                 170                 175 aat ctg tgc ccc ttc ggc gag gtg ttc aac gcc aca aga ttc gcc tct     576
Asn Leu Cys Pro Phe Gly Glu Val Phe Asn Ala Thr Arg Phe Ala Ser
            180                 185                 190 gtg tac gcc tgg aac cgg aag cgg atc agc aat tgc gtg gcc gac tac     624
Val Tyr Ala Trp Asn Arg Lys Arg Ile Ser Asn Cys Val Ala Asp Tyr
        195                 200                 205 agc gtg ctg tac aac agc gcc agc ttc tcc acc ttc aag tgc tac ggc     672
Ser Val Leu Tyr Asn Ser Ala Ser Phe Ser Thr Phe Lys Cys Tyr Gly
    210                 215                 220 gtg tcc cct acc aag ctg aac gac ctg tgc ttt acc aac gtg tac gcc     720
Val Ser Pro Thr Lys Leu Asn Asp Leu Cys Phe Thr Asn Val Tyr Ala
225                 230                 235                 240 gat agc ttc gtg atc cgg gga gat gaa gtg cgg cag atc gct cct gga     768
Asp Ser Phe Val Ile Arg Gly Asp Glu Val Arg Gln Ile Ala Pro Gly
                245                 250                 255
```

| | | | | | | | | | | | | | | | | |
|---|---|---|---|---|---|---|---|---|---|---|---|---|---|---|---|---|
| cag | aca | ggc | aag | atc | gcc | gac | tat | aac | tac | aag | ctg | ccc | gac | gac | ttc | 816 |
| Gln | Thr | Gly | Lys | Ile | Ala | Asp | Tyr | Asn | Tyr | Lys | Leu | Pro | Asp | Asp | Phe | |
| | | | 260 | | | | | 265 | | | | | 270 | | | |
| acc | ggc | tgt | gtg | att | gcc | tgg | aac | agc | aac | aac | ctg | gac | agc | aaa | gtc | 864 |
| Thr | Gly | Cys | Val | Ile | Ala | Trp | Asn | Ser | Asn | Asn | Leu | Asp | Ser | Lys | Val | |
| | | 275 | | | | | 280 | | | | | 285 | | | | |
| ggc | ggc | aac | tac | aat | tac | ctg | tac | cgg | ctg | ttc | cgg | aag | tcc | aat | ctg | 912 |
| Gly | Gly | Asn | Tyr | Asn | Tyr | Leu | Tyr | Arg | Leu | Phe | Arg | Lys | Ser | Asn | Leu | |
| | 290 | | | | | 295 | | | | | 300 | | | | | |
| aag | ccc | ttc | gag | cgg | gac | atc | agc | acc | gag | atc | tat | cag | gcc | ggc | agc | 960 |
| Lys | Pro | Phe | Glu | Arg | Asp | Ile | Ser | Thr | Glu | Ile | Tyr | Gln | Ala | Gly | Ser | |
| 305 | | | | | 310 | | | | | 315 | | | | | 320 | |
| acc | cct | tgc | aat | ggc | gtg | gaa | ggc | ttc | aac | tgc | tac | ttc | cca | ctg | cag | 1008 |
| Thr | Pro | Cys | Asn | Gly | Val | Glu | Gly | Phe | Asn | Cys | Tyr | Phe | Pro | Leu | Gln | |
| | | | | 325 | | | | | 330 | | | | | 335 | | |
| tcc | tac | ggc | ttc | cag | cct | aca | aac | ggc | gtg | ggc | tac | cag | cct | tac | aga | 1056 |
| Ser | Tyr | Gly | Phe | Gln | Pro | Thr | Asn | Gly | Val | Gly | Tyr | Gln | Pro | Tyr | Arg | |
| | | | 340 | | | | | 345 | | | | | 350 | | | |
| gtg | gtc | gtc | ctg | agc | ttc | gag | ctg | ctg | cat | gcc | cct | gct | aca | gtg | tgc | 1104 |
| Val | Val | Val | Leu | Ser | Phe | Glu | Leu | Leu | His | Ala | Pro | Ala | Thr | Val | Cys | |
| | | 355 | | | | | 360 | | | | | 365 | | | | |
| ggc | cct | aag | aag | tct | acc | aac | ctg | gaa | ttc | ggc | gga | ggc | agc | ggc | ggt | 1152 |
| Gly | Pro | Lys | Lys | Ser | Thr | Asn | Leu | Glu | Phe | Gly | Gly | Gly | Ser | Gly | Gly | |
| 370 | | | | | 375 | | | | | 380 | | | | | | |
| gga | agc | ggc | gga | ggc | tct | gct | tgg | agc | cac | ccg | cag | ttc | gaa | aaa | ggt | 1200 |
| Gly | Ser | Gly | Gly | Gly | Ser | Ala | Trp | Ser | His | Pro | Gln | Phe | Glu | Lys | Gly | |
| 385 | | | | | 390 | | | | | 395 | | | | | 400 | |
| gga | ggt | tct | ggc | ggt | gga | tcg | gga | ggt | tca | gcg | tgg | agc | cac | ccg | cag | 1248 |
| Gly | Gly | Ser | Gly | Gly | Gly | Ser | Gly | Gly | Ser | Ala | Trp | Ser | His | Pro | Gln | |
| | | | | 405 | | | | | 410 | | | | | 415 | | |
| ttc | gag | aaa | tga | | | | | | | | | | | | | 1260 |
| Phe | Glu | Lys | | | | | | | | | | | | | | |

<210> SEQ ID NO 2
<211> LENGTH: 419
<212> TYPE: PRT
<213> ORGANISM: Artificial Sequence
<220> FEATURE:
<223> OTHER INFORMATION: Synthetic Construct

<400> SEQUENCE: 2

| | | | | | | | | | | | | | | |
|---|---|---|---|---|---|---|---|---|---|---|---|---|---|---|
| Met | Thr | Asn | Lys | Cys | Leu | Leu | Gln | Ile | Ala | Leu | Leu | Leu | Cys | Phe | Ser |
| 1 | | | | 5 | | | | | 10 | | | | | 15 | |
| Thr | Thr | Ala | Leu | Ser | Met | Gly | Ala | Pro | Gln | Val | Gln | Leu | Gln | Glu | Ser |
| | | | 20 | | | | | 25 | | | | | 30 | | |
| Gly | Gly | Gly | Ser | Val | Gln | Ala | Gly | Gly | Ser | Leu | Arg | Leu | Ser | Cys | Val |
| | | 35 | | | | | 40 | | | | | 45 | | | |
| Ala | Ser | Gly | Tyr | Thr | Asp | Ser | Thr | Tyr | Cys | Val | Gly | Trp | Phe | Arg | Gln |
| | 50 | | | | | 55 | | | | | 60 | | | | |
| Ala | Pro | Gly | Lys | Glu | Arg | Glu | Gly | Val | Ala | Arg | Ile | Asn | Thr | Ile | Ser |
| 65 | | | | | 70 | | | | | 75 | | | | | 80 |
| Gly | Arg | Pro | Trp | Tyr | Ala | Asp | Ser | Val | Lys | Gly | Arg | Phe | Thr | Ile | Ser |
| | | | | 85 | | | | | 90 | | | | | 95 | |
| Gln | Asp | Asn | Ser | Lys | Asn | Thr | Val | Tyr | Leu | Gln | Met | Asn | Ser | Leu | Lys |
| | | | 100 | | | | | 105 | | | | | 110 | | |
| Pro | Glu | Asp | Thr | Ala | Ile | Tyr | Tyr | Cys | Thr | Leu | Thr | Thr | Ala | Asn | Ser |
| | | 115 | | | | | 120 | | | | | 125 | | | |
| Arg | Gly | Phe | Cys | Ser | Gly | Gly | Tyr | Asn | Tyr | Lys | Gly | Gln | Gly | Thr | Gln |
| | 130 | | | | | 135 | | | | | 140 | | | | |

```
Val Thr Val Ser Gly Thr Ser Gly Gly Gly Ser Gly Gly Gly
145                 150                 155                 160

Gly Ser Gly Gly Gly Ser Ala Ala Arg Phe Pro Asn Ile Thr
                165                 170                 175

Asn Leu Cys Pro Phe Gly Glu Val Phe Asn Ala Thr Arg Phe Ala Ser
            180                 185                 190

Val Tyr Ala Trp Asn Arg Lys Arg Ile Ser Asn Cys Val Ala Asp Tyr
        195                 200                 205

Ser Val Leu Tyr Asn Ser Ala Ser Phe Ser Thr Phe Lys Cys Tyr Gly
210                 215                 220

Val Ser Pro Thr Lys Leu Asn Asp Leu Cys Phe Thr Asn Val Tyr Ala
225                 230                 235                 240

Asp Ser Phe Val Ile Arg Gly Asp Glu Val Arg Gln Ile Ala Pro Gly
                245                 250                 255

Gln Thr Gly Lys Ile Ala Asp Tyr Asn Tyr Lys Leu Pro Asp Asp Phe
            260                 265                 270

Thr Gly Cys Val Ile Ala Trp Asn Ser Asn Asn Leu Asp Ser Lys Val
        275                 280                 285

Gly Gly Asn Tyr Asn Tyr Leu Tyr Arg Leu Phe Arg Lys Ser Asn Leu
290                 295                 300

Lys Pro Phe Glu Arg Asp Ile Ser Thr Glu Ile Tyr Gln Ala Gly Ser
305                 310                 315                 320

Thr Pro Cys Asn Gly Val Glu Gly Phe Asn Cys Tyr Phe Pro Leu Gln
                325                 330                 335

Ser Tyr Gly Phe Gln Pro Thr Asn Gly Val Gly Tyr Gln Pro Tyr Arg
            340                 345                 350

Val Val Val Leu Ser Phe Glu Leu Leu His Ala Pro Ala Thr Val Cys
        355                 360                 365

Gly Pro Lys Lys Ser Thr Asn Leu Glu Phe Gly Gly Gly Ser Gly Gly
370                 375                 380

Gly Ser Gly Gly Gly Ser Ala Trp Ser His Pro Gln Phe Glu Lys Gly
385                 390                 395                 400

Gly Gly Ser Gly Gly Gly Ser Gly Gly Ser Ala Trp Ser His Pro Gln
                405                 410                 415

Phe Glu Lys

<210> SEQ ID NO 3
<211> LENGTH: 1899
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1899)

<400> SEQUENCE: 3 atg acc aac aag tgc ctg ctg cag att gcc ctg ctg ctg tgc ttc agc    48
Met Thr Asn Lys Cys Leu Leu Gln Ile Ala Leu Leu Leu Cys Phe Ser
1               5                   10                  15 aca aca gcc ctg tct atg ggc gcg cct caa gtt cag ctt caa gaa tct    96
Thr Thr Ala Leu Ser Met Gly Ala Pro Gln Val Gln Leu Gln Glu Ser
                20                  25                  30 ggc ggc gga agc gtt cag gct ggc gga tct ctg aga ctg agc tgt gtg   144
Gly Gly Gly Ser Val Gln Ala Gly Gly Ser Leu Arg Leu Ser Cys Val
            35                  40                  45
```

-continued

| | | |
|---|---|---|
| gcc agc ggc tac acc gat agc aca tac tgc gtc ggc tgg ttc aga cag<br>Ala Ser Gly Tyr Thr Asp Ser Thr Tyr Cys Val Gly Trp Phe Arg Gln<br>50                   55                     60 | 192 |
| gcc cct ggc aaa gag aga gag ggc gtc gcc aga atc aac acc atc agc<br>Ala Pro Gly Lys Glu Arg Glu Gly Val Ala Arg Ile Asn Thr Ile Ser<br>65                   70                 75                     80 | 240 |
| ggc aga cct tgg tac gcc gac tct gtg aag ggc aga ttc aca atc agc<br>Gly Arg Pro Trp Tyr Ala Asp Ser Val Lys Gly Arg Phe Thr Ile Ser<br>                   85                     90                 95 | 288 |
| cag gac aac agc aag aac acc gtg tac ctg cag atg aac agc ctg aag<br>Gln Asp Asn Ser Lys Asn Thr Val Tyr Leu Gln Met Asn Ser Leu Lys<br>             100                    105                    110 | 336 |
| cct gag gac acc gcc atc tac tac tgc acc ctg acc acc gcc aac agc<br>Pro Glu Asp Thr Ala Ile Tyr Tyr Cys Thr Leu Thr Thr Ala Asn Ser<br>             115                    120                    125 | 384 |
| aga ggc ttt tgt tcc ggc ggc tac aac tac aaa ggc cag ggc acc caa<br>Arg Gly Phe Cys Ser Gly Gly Tyr Asn Tyr Lys Gly Gln Gly Thr Gln<br>130                    135                    140 | 432 |
| gtg acc gtg tct ggt ggt acc agc gga ggc gga gga tca ggt ggc gga<br>Val Thr Val Ser Gly Gly Thr Ser Gly Gly Gly Gly Ser Gly Gly Gly<br>145                    150                    155                    160 | 480 |
| ggt agt ggt ggt ggc ggt agc gcg gcc gcc atg tct gat aac ggc cct<br>Gly Ser Gly Gly Gly Gly Ser Ala Ala Ala Met Ser Asp Asn Gly Pro<br>                   165                    170                    175 | 528 |
| cag aac cag cgg aac gcc cct aga atc aca ttt ggc ggc cct agc gat<br>Gln Asn Gln Arg Asn Ala Pro Arg Ile Thr Phe Gly Gly Pro Ser Asp<br>             180                    185                    190 | 576 |
| agc acc ggc agc aat cag aat ggc gag aga agc ggc gcc aga agc aag<br>Ser Thr Gly Ser Asn Gln Asn Gly Glu Arg Ser Gly Ala Arg Ser Lys<br>                   195                    200                    205 | 624 |
| cag aga agg cct caa ggc ctg cct aac aac acc gcc agc tgg ttc aca<br>Gln Arg Arg Pro Gln Gly Leu Pro Asn Asn Thr Ala Ser Trp Phe Thr<br>210                    215                    220 | 672 |
| gcc ctg aca cag cac ggc aaa gag gac ctg aag ttc ccc aga gga cag<br>Ala Leu Thr Gln His Gly Lys Glu Asp Leu Lys Phe Pro Arg Gly Gln<br>225                    230                    235                    240 | 720 |
| ggc gtg ccc atc aac aca aac agc agc ccc gat gac cag atc ggc tac<br>Gly Val Pro Ile Asn Thr Asn Ser Ser Pro Asp Asp Gln Ile Gly Tyr<br>                   245                    250                    255 | 768 |
| tac aga cgg gcc acc aga aga atc aga ggc ggc gac ggc aag atg aag<br>Tyr Arg Arg Ala Thr Arg Arg Ile Arg Gly Gly Asp Gly Lys Met Lys<br>             260                    265                    270 | 816 |
| gat ctg agc ccc aga tgg tac ttc tac tac ctc ggc aca gga ccc gaa<br>Asp Leu Ser Pro Arg Trp Tyr Phe Tyr Tyr Leu Gly Thr Gly Pro Glu<br>             275                    280                    285 | 864 |
| gcc gga ctt cct tat ggc gcc aac aag gac ggc atc atc tgg gtt gca<br>Ala Gly Leu Pro Tyr Gly Ala Asn Lys Asp Gly Ile Ile Trp Val Ala<br>290                    295                    300 | 912 |
| aca gaa ggc gcc ctg aac acc cct aag gac cac atc ggc acc aga aat<br>Thr Glu Gly Ala Leu Asn Thr Pro Lys Asp His Ile Gly Thr Arg Asn<br>305                    310                    315                    320 | 960 |
| ccc gcc aac aat gcc gcc att gtg ctg cag ttg cct cag ggc aca aca<br>Pro Ala Asn Asn Ala Ala Ile Val Leu Gln Leu Pro Gln Gly Thr Thr<br>                   325                    330                    335 | 1008 |
| ctg ccc aag ggc ttt tac gcc gag ggc agc aga gga gga agc cag gcc<br>Leu Pro Lys Gly Phe Tyr Ala Glu Gly Ser Arg Gly Gly Ser Gln Ala<br>             340                    345                    350 | 1056 |
| tct agc aga agc tcc agc aga agc cgg aac tcc agc cgg aat agc aca<br>Ser Ser Arg Ser Ser Ser Arg Ser Arg Asn Ser Ser Arg Asn Ser Thr<br>                   355                    360                    365 | 1104 |

```
cct gga agc agc agg ggc aca agc cct gct aga atg gct ggc aat ggc    1152
Pro Gly Ser Ser Arg Gly Thr Ser Pro Ala Arg Met Ala Gly Asn Gly
        370                 375                 380 gga gat gct gct ctg gcc ctg ttg ctg ctg gac cgg ctg aat cag ctg    1200
Gly Asp Ala Ala Leu Ala Leu Leu Leu Leu Asp Arg Leu Asn Gln Leu
385                 390                 395                 400 gaa agc aag atg agc ggc aag ggc cag caa cag cag gga cag acc gtg    1248
Glu Ser Lys Met Ser Gly Lys Gly Gln Gln Gln Gln Gly Gln Thr Val
                405                 410                 415 acc aaa aag tct gcc gcc gag gcc agc aag aag ccc aga cag aaa aga    1296
Thr Lys Lys Ser Ala Ala Glu Ala Ser Lys Lys Pro Arg Gln Lys Arg
            420                 425                 430 acc gcc acc aag gcc tac aac gtg acc cag gcc ttt gga aga aga ggc    1344
Thr Ala Thr Lys Ala Tyr Asn Val Thr Gln Ala Phe Gly Arg Arg Gly
        435                 440                 445 cct gag cag acc cag ggc aac ttc gga gat caa gag ctg atc aga cag    1392
Pro Glu Gln Thr Gln Gly Asn Phe Gly Asp Gln Glu Leu Ile Arg Gln
450                 455                 460 ggc acc gac tac aag cac tgg cct cag atc gcc cag ttt gcc cca tct    1440
Gly Thr Asp Tyr Lys His Trp Pro Gln Ile Ala Gln Phe Ala Pro Ser
465                 470                 475                 480 gcc agc gcc ttt ttc ggc atg agc cgg atc ggc atg gaa gtg aca cct    1488
Ala Ser Ala Phe Phe Gly Met Ser Arg Ile Gly Met Glu Val Thr Pro
                485                 490                 495 agc ggc acc tgg ctg aca tac aca ggc gcc atc aag ctg gac gac aag    1536
Ser Gly Thr Trp Leu Thr Tyr Thr Gly Ala Ile Lys Leu Asp Asp Lys
            500                 505                 510 gac ccc aac ttc aag gac caa gtg atc ctg ctg aac aag cac atc gac    1584
Asp Pro Asn Phe Lys Asp Gln Val Ile Leu Leu Asn Lys His Ile Asp
        515                 520                 525 gcc tac aag aca ttc cct cca acc gag cct aag aag gac aag aag aag    1632
Ala Tyr Lys Thr Phe Pro Pro Thr Glu Pro Lys Lys Asp Lys Lys Lys
    530                 535                 540 aag gcc gac gag aca cag gcc ctg cct cag cgc cag aaa aag cag cag    1680
Lys Ala Asp Glu Thr Gln Ala Leu Pro Gln Arg Gln Lys Lys Gln Gln
545                 550                 555                 560 aca gtg aca ctg ctg cca gcc gcc gac ctg gac gat ttt tct aag cag    1728
Thr Val Thr Leu Leu Pro Ala Ala Asp Leu Asp Asp Phe Ser Lys Gln
                565                 570                 575 ctg cag cag tcc atg agc agc gcc gat tct acc cag gcc gaa ttc ggc    1776
Leu Gln Gln Ser Met Ser Ser Ala Asp Ser Thr Gln Ala Glu Phe Gly
            580                 585                 590 gga ggt tca ggc ggt gga agt ggt ggt gga tct gct tgg agc cat cct    1824
Gly Gly Ser Gly Gly Gly Ser Gly Gly Gly Ser Ala Trp Ser His Pro
        595                 600                 605 cag ttc gag aaa ggc ggt ggt agc ggc gga gga agc ggt ggc tca gct    1872
Gln Phe Glu Lys Gly Gly Gly Ser Gly Gly Gly Ser Gly Gly Ser Ala
    610                 615                 620 tgg tca cac cca cag ttt gag aag tga                                1899
Trp Ser His Pro Gln Phe Glu Lys
625                 630
```

<210> SEQ ID NO 4
<211> LENGTH: 632
<212> TYPE: PRT
<213> ORGANISM: Artificial Sequence
<220> FEATURE:
<223> OTHER INFORMATION: Synthetic Construct

<400> SEQUENCE: 4

```
Met Thr Asn Lys Cys Leu Leu Gln Ile Ala Leu Leu Leu Cys Phe Ser
1               5                   10                  15

Thr Thr Ala Leu Ser Met Gly Ala Pro Gln Val Gln Leu Gln Glu Ser
            20                  25                  30

Gly Gly Gly Ser Val Gln Ala Gly Gly Ser Leu Arg Leu Ser Cys Val
                35                  40                  45

Ala Ser Gly Tyr Thr Asp Ser Thr Tyr Cys Val Gly Trp Phe Arg Gln
    50                  55                  60

Ala Pro Gly Lys Glu Arg Glu Gly Val Ala Arg Ile Asn Thr Ile Ser
65                  70                  75                  80

Gly Arg Pro Trp Tyr Ala Asp Ser Val Lys Gly Arg Phe Thr Ile Ser
                85                  90                  95

Gln Asp Asn Ser Lys Asn Thr Val Tyr Leu Gln Met Asn Ser Leu Lys
                100                 105                 110

Pro Glu Asp Thr Ala Ile Tyr Tyr Cys Thr Leu Thr Thr Ala Asn Ser
            115                 120                 125

Arg Gly Phe Cys Ser Gly Gly Tyr Asn Tyr Lys Gly Gln Gly Thr Gln
130                 135                 140

Val Thr Val Ser Gly Gly Thr Ser Gly Gly Gly Ser Gly Gly Gly
145             150                 155                 160

Gly Ser Gly Gly Gly Gly Ser Ala Ala Ala Met Ser Asp Asn Gly Pro
                165                 170                 175

Gln Asn Gln Arg Asn Ala Pro Arg Ile Thr Phe Gly Gly Pro Ser Asp
                180                 185                 190

Ser Thr Gly Ser Asn Gln Asn Gly Glu Arg Ser Gly Ala Arg Ser Lys
            195                 200                 205

Gln Arg Arg Pro Gln Gly Leu Pro Asn Asn Thr Ala Ser Trp Phe Thr
210                 215                 220

Ala Leu Thr Gln His Gly Lys Glu Asp Leu Lys Phe Pro Arg Gly Gln
225                 230                 235                 240

Gly Val Pro Ile Asn Thr Asn Ser Ser Pro Asp Asp Gln Ile Gly Tyr
                245                 250                 255

Tyr Arg Arg Ala Thr Arg Arg Ile Arg Gly Gly Asp Gly Lys Met Lys
                260                 265                 270

Asp Leu Ser Pro Arg Trp Tyr Phe Tyr Tyr Leu Gly Thr Gly Pro Glu
            275                 280                 285

Ala Gly Leu Pro Tyr Gly Ala Asn Lys Asp Gly Ile Ile Trp Val Ala
                290                 295                 300

Thr Glu Gly Ala Leu Asn Thr Pro Lys Asp His Ile Gly Thr Arg Asn
305                 310                 315                 320

Pro Ala Asn Asn Ala Ala Ile Val Leu Gln Leu Pro Gln Gly Thr Thr
                325                 330                 335

Leu Pro Lys Gly Phe Tyr Ala Glu Gly Ser Arg Gly Gly Ser Gln Ala
                340                 345                 350

Ser Ser Arg Ser Ser Ser Arg Ser Arg Asn Ser Ser Arg Asn Ser Thr
            355                 360                 365

Pro Gly Ser Ser Arg Gly Thr Ser Pro Ala Arg Met Ala Gly Asn Gly
            370                 375                 380

Gly Asp Ala Ala Leu Ala Leu Leu Leu Leu Asp Arg Leu Asn Gln Leu
385                 390                 395                 400

Glu Ser Lys Met Ser Gly Lys Gly Gln Gln Gln Gln Gly Gln Thr Val
            405                 410                 415

Thr Lys Lys Ser Ala Ala Glu Ala Ser Lys Lys Pro Arg Gln Lys Arg
```

-continued

```
                420                 425                 430
Thr Ala Thr Lys Ala Tyr Asn Val Thr Gln Ala Phe Gly Arg Arg Gly
            435                 440                 445

Pro Glu Gln Thr Gln Gly Asn Phe Gly Asp Gln Glu Leu Ile Arg Gln
450                 455                 460

Gly Thr Asp Tyr Lys His Trp Pro Gln Ile Ala Gln Phe Ala Pro Ser
465                 470                 475                 480

Ala Ser Ala Phe Phe Gly Met Ser Arg Ile Gly Met Glu Val Thr Pro
                485                 490                 495

Ser Gly Thr Trp Leu Thr Tyr Thr Gly Ala Ile Lys Leu Asp Asp Lys
            500                 505                 510

Asp Pro Asn Phe Lys Asp Gln Val Ile Leu Leu Asn Lys His Ile Asp
            515                 520                 525

Ala Tyr Lys Thr Phe Pro Pro Thr Glu Pro Lys Lys Asp Lys Lys Lys
            530                 535                 540

Lys Ala Asp Glu Thr Gln Ala Leu Pro Gln Arg Gln Lys Lys Gln Gln
545                 550                 555                 560

Thr Val Thr Leu Leu Pro Ala Ala Asp Leu Asp Asp Phe Ser Lys Gln
                565                 570                 575

Leu Gln Gln Ser Met Ser Ser Ala Asp Ser Thr Gln Ala Glu Phe Gly
                580                 585                 590

Gly Gly Ser Gly Gly Gly Ser Gly Gly Ser Ala Trp Ser His Pro
            595                 600                 605

Gln Phe Glu Lys Gly Gly Gly Ser Gly Gly Gly Ser Gly Gly Ser Ala
            610                 615                 620

Trp Ser His Pro Gln Phe Glu Lys
625                 630

<210> SEQ ID NO 5
<211> LENGTH: 954
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(954)

<400> SEQUENCE: 5 atg acc aac aag tgc ctg ctg cag att gcc ctg ctg ctg tgc ttc agc      48
Met Thr Asn Lys Cys Leu Leu Gln Ile Ala Leu Leu Leu Cys Phe Ser
1               5                   10                  15 aca aca gcc ctg tct atg ggc gcg cct caa gtt cag ctt caa gaa tct      96
Thr Thr Ala Leu Ser Met Gly Ala Pro Gln Val Gln Leu Gln Glu Ser
            20                  25                  30 ggc ggc gga agc gtt cag gct ggc gga tct ctg aga ctg agc tgt gtg     144
Gly Gly Gly Ser Val Gln Ala Gly Gly Ser Leu Arg Leu Ser Cys Val
        35                  40                  45 gcc agc ggc tac acc gat agc aca tac tgc gtc ggc tgg ttc aga cag     192
Ala Ser Gly Tyr Thr Asp Ser Thr Tyr Cys Val Gly Trp Phe Arg Gln
    50                  55                  60 gcc cct ggc aaa gag aga gag ggc gtc gcc aga atc aac acc atc agc     240
Ala Pro Gly Lys Glu Arg Glu Gly Val Ala Arg Ile Asn Thr Ile Ser
65                  70                  75                  80 ggc aga cct tgg tac gcc gac tct gtg aag ggc aga ttc aca atc agc     288
Gly Arg Pro Trp Tyr Ala Asp Ser Val Lys Gly Arg Phe Thr Ile Ser
                85                  90                  95 cag gac aac agc aag aac acc gtg tac ctg cag atg aac agc ctg aag     336
```

```
cct gag gac acc gcc atc tac tac tgc acc ctg acc acc gcc aac agc      384
Pro Glu Asp Thr Ala Ile Tyr Tyr Cys Thr Leu Thr Thr Ala Asn Ser
        115                 120                 125 aga ggc ttt tgt tcc ggc ggc tac aac tac aaa ggc cag ggc acc caa      432
Arg Gly Phe Cys Ser Gly Gly Tyr Asn Tyr Lys Gly Gln Gly Thr Gln
130                 135                 140 gtg acc gtg tct ggt ggt acc agc gga ggc gga gga tca ggt ggc gga      480
Val Thr Val Ser Gly Gly Thr Ser Gly Gly Gly Gly Ser Gly Gly Gly
145                 150                 155                 160 ggt agt ggt ggt ggc ggt agc gcg gcc gcc caa gaa tgt agc ctg cag      528
Gly Ser Gly Gly Gly Gly Ser Ala Ala Ala Gln Glu Cys Ser Leu Gln
                165                 170                 175 agc tgc aca cag cac cag cct tac gtg gtg gac gac ccc tgt cct atc      576
Ser Cys Thr Gln His Gln Pro Tyr Val Val Asp Asp Pro Cys Pro Ile
                180                 185                 190 cac ttc tac agc aag tgg tac atc aga gtg ggc gcc aga aag agc gcc      624
His Phe Tyr Ser Lys Trp Tyr Ile Arg Val Gly Ala Arg Lys Ser Ala
            195                 200                 205 cca ctg att gag ctg tgt gtg gat gag gcc ggc agc aag agc ccc atc      672
Pro Leu Ile Glu Leu Cys Val Asp Glu Ala Gly Ser Lys Ser Pro Ile
210                 215                 220 cag tac atc gac atc ggc aac tac acc gtg tcc tgc ctg cct ttc acc      720
Gln Tyr Ile Asp Ile Gly Asn Tyr Thr Val Ser Cys Leu Pro Phe Thr
225                 230                 235                 240 atc aac tgc caa gag cct aag ctg ggc tct ctg gtc gtg cgg tgc agc      768
Ile Asn Cys Gln Glu Pro Lys Leu Gly Ser Leu Val Val Arg Cys Ser
                245                 250                 255 ttc tac gag gac ttc ctg gaa tac cac gac gtg cgc gtg gtg ctg gat      816
Phe Tyr Glu Asp Phe Leu Glu Tyr His Asp Val Arg Val Val Leu Asp
            260                 265                 270 ttc atc ccg cgg ggt ggt ggt agt ggc gga gga agt ggt ggc gga tct      864
Phe Ile Pro Arg Gly Gly Gly Ser Gly Gly Gly Ser Gly Gly Gly Ser
        275                 280                 285 gct tgg agc cat cct cag ttc gag aaa ggc ggc ggt tca ggt ggt gga      912
Ala Trp Ser His Pro Gln Phe Glu Lys Gly Gly Gly Ser Gly Gly Gly
290                 295                 300 tca ggc ggt tct gca tgg tca cac cca cag ttt gag aag tga              954
Ser Gly Gly Ser Ala Trp Ser His Pro Gln Phe Glu Lys
305                 310                 315

<210> SEQ ID NO 6
<211> LENGTH: 317
<212> TYPE: PRT
<213> ORGANISM: Artificial Sequence
<220> FEATURE:
<223> OTHER INFORMATION: Synthetic Construct

<400> SEQUENCE: 6

Met Thr Asn Lys Cys Leu Leu Gln Ile Ala Leu Leu Leu Cys Phe Ser
1               5                   10                  15

Thr Thr Ala Leu Ser Met Gly Ala Pro Gln Val Gln Leu Gln Glu Ser
            20                  25                  30

Gly Gly Gly Ser Val Gln Ala Gly Gly Ser Leu Arg Leu Ser Cys Val
        35                  40                  45

Ala Ser Gly Tyr Thr Asp Ser Thr Tyr Cys Val Gly Trp Phe Arg Gln
    50                  55                  60

Ala Pro Gly Lys Glu Arg Glu Gly Val Ala Arg Ile Asn Thr Ile Ser
65                  70                  75                  80
```

```
Gly Arg Pro Trp Tyr Ala Asp Ser Val Lys Gly Arg Phe Thr Ile Ser
                 85                  90                  95

Gln Asp Asn Ser Lys Asn Thr Val Tyr Leu Gln Met Asn Ser Leu Lys
            100                 105                 110

Pro Glu Asp Thr Ala Ile Tyr Tyr Cys Thr Leu Thr Thr Ala Asn Ser
        115                 120                 125

Arg Gly Phe Cys Ser Gly Gly Tyr Asn Tyr Lys Gly Gln Gly Thr Gln
    130                 135                 140

Val Thr Val Ser Gly Gly Thr Ser Gly Gly Gly Ser Gly Gly Gly
145                 150                 155                 160

Gly Ser Gly Gly Gly Ser Ala Ala Gln Glu Cys Ser Leu Gln
                165                 170                 175

Ser Cys Thr Gln His Gln Pro Tyr Val Val Asp Asp Pro Cys Pro Ile
            180                 185                 190

His Phe Tyr Ser Lys Trp Tyr Ile Arg Val Gly Ala Arg Lys Ser Ala
        195                 200                 205

Pro Leu Ile Glu Leu Cys Val Asp Glu Ala Gly Ser Lys Ser Pro Ile
    210                 215                 220

Gln Tyr Ile Asp Ile Gly Asn Tyr Thr Val Ser Cys Leu Pro Phe Thr
225                 230                 235                 240

Ile Asn Cys Gln Glu Pro Lys Leu Gly Ser Leu Val Val Arg Cys Ser
                245                 250                 255

Phe Tyr Glu Asp Phe Leu Glu Tyr His Asp Val Arg Val Val Leu Asp
            260                 265                 270

Phe Ile Pro Arg Gly Gly Gly Ser Gly Gly Gly Ser Gly Gly Gly Ser
        275                 280                 285

Ala Trp Ser His Pro Gln Phe Glu Lys Gly Gly Gly Ser Gly Gly Gly
    290                 295                 300

Ser Gly Gly Ser Ala Trp Ser His Pro Gln Phe Glu Lys
305                 310                 315

<210> SEQ ID NO 7
<211> LENGTH: 1635
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1635)

<400> SEQUENCE: 7 atg acc aac aag tgc ctg ctg cag att gcc ctg ctg ctg tgc ttc agc     48
Met Thr Asn Lys Cys Leu Leu Gln Ile Ala Leu Leu Leu Cys Phe Ser
1               5                   10                  15 aca aca gcc ctg tct atg ggc gcg cct caa gtt cag ctt caa gaa tct     96
Thr Thr Ala Leu Ser Met Gly Ala Pro Gln Val Gln Leu Gln Glu Ser
            20                  25                  30 ggc ggc gga agc gtt cag gct ggc gga tct ctg aga ctg agc tgt gtg    144
Gly Gly Gly Ser Val Gln Ala Gly Gly Ser Leu Arg Leu Ser Cys Val
        35                  40                  45 gcc agc ggc tac acc gat agc aca tac tgc gtc ggc tgg ttc aga cag    192
Ala Ser Gly Tyr Thr Asp Ser Thr Tyr Cys Val Gly Trp Phe Arg Gln
    50                  55                  60 gcc cct ggc aaa gag aga gag ggc gtc gcc aga atc aac acc atc agc    240
Ala Pro Gly Lys Glu Arg Glu Gly Val Ala Arg Ile Asn Thr Ile Ser
65                  70                  75                  80
```

```
ggc aga cct tgg tac gcc gac tct gtg aag ggc aga ttc aca atc agc    288
Gly Arg Pro Trp Tyr Ala Asp Ser Val Lys Gly Arg Phe Thr Ile Ser
             85                  90                  95 cag gac aac agc aag aac acc gtg tac ctg cag atg aac agc ctg aag    336
Gln Asp Asn Ser Lys Asn Thr Val Tyr Leu Gln Met Asn Ser Leu Lys
            100                 105                 110 cct gag gac acc gcc atc tac tac tgc acc ctg acc acc gcc aac agc    384
Pro Glu Asp Thr Ala Ile Tyr Tyr Cys Thr Leu Thr Thr Ala Asn Ser
            115                 120                 125 aga ggc ttt tgt tcc ggc ggc tac aac tac aaa ggc cag ggc acc caa    432
Arg Gly Phe Cys Ser Gly Gly Tyr Asn Tyr Lys Gly Gln Gly Thr Gln
130                 135                 140 gtg acc gtg tct ggt ggt acc agc gga ggc gga gga tca ggt ggc gga    480
Val Thr Val Ser Gly Gly Thr Ser Gly Gly Gly Gly Ser Gly Gly Gly
145                 150                 155                 160 ggt agt ggt ggt ggc ggt agc gcg gcc gct aga ttc ccc aac atc acc    528
Gly Ser Gly Gly Gly Gly Ser Ala Ala Ala Arg Phe Pro Asn Ile Thr
                165                 170                 175 aat ctg tgc ccc ttc ggc gag gtg ttc aac gcc aca aga ttc gcc tct    576
Asn Leu Cys Pro Phe Gly Glu Val Phe Asn Ala Thr Arg Phe Ala Ser
            180                 185                 190 gtg tac gcc tgg aac cgg aag cgg atc agc aat tgc gtg gcc gac tac    624
Val Tyr Ala Trp Asn Arg Lys Arg Ile Ser Asn Cys Val Ala Asp Tyr
            195                 200                 205 agc gtg ctg tac aac agc gcc agc ttc tcc acc ttc aag tgc tac ggc    672
Ser Val Leu Tyr Asn Ser Ala Ser Phe Ser Thr Phe Lys Cys Tyr Gly
        210                 215                 220 gtg tcc cct acc aag ctg aac gac ctg tgc ttt acc aac gtg tac gcc    720
Val Ser Pro Thr Lys Leu Asn Asp Leu Cys Phe Thr Asn Val Tyr Ala
225                 230                 235                 240 gat agc ttc gtg atc cgg gga gat gaa gtg cgg cag atc gct cct gga    768
Asp Ser Phe Val Ile Arg Gly Asp Glu Val Arg Gln Ile Ala Pro Gly
                245                 250                 255 cag aca ggc aag atc gcc gac tat aac tac aag ctg ccc gac gac ttc    816
Gln Thr Gly Lys Ile Ala Asp Tyr Asn Tyr Lys Leu Pro Asp Asp Phe
            260                 265                 270 acc ggc tgt gtg att gcc tgg aac agc aac aac ctg gac agc aaa gtc    864
Thr Gly Cys Val Ile Ala Trp Asn Ser Asn Asn Leu Asp Ser Lys Val
            275                 280                 285 ggc ggc aac tac aat tac ctg tac cgg ctg ttc cgg aag tcc aat ctg    912
Gly Gly Asn Tyr Asn Tyr Leu Tyr Arg Leu Phe Arg Lys Ser Asn Leu
290                 295                 300 aag ccc ttc gag cgg gac atc agc acc gag atc tat cag gcc ggc agc    960
Lys Pro Phe Glu Arg Asp Ile Ser Thr Glu Ile Tyr Gln Ala Gly Ser
305                 310                 315                 320 acc cct tgc aat ggc gtg gaa ggc ttc aac tgc tac ttc cca ctg cag   1008
Thr Pro Cys Asn Gly Val Glu Gly Phe Asn Cys Tyr Phe Pro Leu Gln
                325                 330                 335 tcc tac ggc ttc cag cct aca aac ggc gtg ggc tac cag cct tac aga   1056
Ser Tyr Gly Phe Gln Pro Thr Asn Gly Val Gly Tyr Gln Pro Tyr Arg
            340                 345                 350 gtg gtg gtc ctg agc ttc gag ctg ctg cat gcc cct gct aca gtg tgc   1104
Val Val Val Leu Ser Phe Glu Leu Leu His Ala Pro Ala Thr Val Cys
            355                 360                 365 ggc cct aag aag tct acc aac ctg gaa ttc tct ggc ggc gga gga tct   1152
Gly Pro Lys Lys Ser Thr Asn Leu Glu Phe Ser Gly Gly Gly Gly Ser
370                 375                 380 ggc gga ggt gga agc gga ggc ggt gga tct gcg gcc gcc caa gaa tgt   1200
Gly Gly Gly Gly Ser Gly Gly Gly Gly Ser Ala Ala Ala Gln Glu Cys
385                 390                 395                 400
```

```
agc ctg cag agc tgc aca cag cac cag cct tac gtg gtg gac gac ccc    1248
Ser Leu Gln Ser Cys Thr Gln His Gln Pro Tyr Val Val Asp Asp Pro
            405                 410                 415 tgt cct atc cac ttc tac agc aag tgg tac atc aga gtg ggc gcc aga    1296
Cys Pro Ile His Phe Tyr Ser Lys Trp Tyr Ile Arg Val Gly Ala Arg
        420                 425                 430 aag agc gcc cca ctg att gag ctg tgt gtg gat gag gcc ggc agc aag    1344
Lys Ser Ala Pro Leu Ile Glu Leu Cys Val Asp Glu Ala Gly Ser Lys
    435                 440                 445 agc ccc atc cag tac atc gac atc ggc aac tac acc gtg tcc tgc ctg    1392
Ser Pro Ile Gln Tyr Ile Asp Ile Gly Asn Tyr Thr Val Ser Cys Leu
450                 455                 460 cct ttc acc atc aac tgc caa gag cct aag ctg ggc tct ctg gtc gtg    1440
Pro Phe Thr Ile Asn Cys Gln Glu Pro Lys Leu Gly Ser Leu Val Val
465                 470                 475                 480 cgg tgc agc ttc tac gag gac ttc ctg gaa tac cac gac gtg cgc gtg    1488
Arg Cys Ser Phe Tyr Glu Asp Phe Leu Glu Tyr His Asp Val Arg Val
                485                 490                 495 gtg ctg gat ttc atc ccg cgg ggt ggt ggt agt ggc gga gga agt ggt    1536
Val Leu Asp Phe Ile Pro Arg Gly Gly Gly Ser Gly Gly Gly Ser Gly
            500                 505                 510 ggc gga tct gct tgg agc cat cct cag ttc gag aaa ggc ggc ggt tca    1584
Gly Gly Ser Ala Trp Ser His Pro Gln Phe Glu Lys Gly Gly Gly Ser
        515                 520                 525 ggt ggt gga tca ggc ggt tct gca tgg tca cac cca cag ttt gag aag    1632
Gly Gly Gly Ser Gly Gly Ser Ala Trp Ser His Pro Gln Phe Glu Lys
    530                 535                 540 tga                                                                 1635

<210> SEQ ID NO 8
<211> LENGTH: 544
<212> TYPE: PRT
<213> ORGANISM: Artificial Sequence
<220> FEATURE:
<223> OTHER INFORMATION: Synthetic Construct

<400> SEQUENCE: 8

Met Thr Asn Lys Cys Leu Leu Gln Ile Ala Leu Leu Leu Cys Phe Ser
1               5                   10                  15

Thr Thr Ala Leu Ser Met Gly Ala Pro Gln Val Gln Leu Gln Glu Ser
            20                  25                  30

Gly Gly Gly Ser Val Gln Ala Gly Gly Ser Leu Arg Leu Ser Cys Val
        35                  40                  45

Ala Ser Gly Tyr Thr Asp Ser Thr Tyr Cys Val Gly Trp Phe Arg Gln
    50                  55                  60

Ala Pro Gly Lys Glu Arg Glu Gly Val Ala Arg Ile Asn Thr Ile Ser
65                  70                  75                  80

Gly Arg Pro Trp Tyr Ala Asp Ser Val Lys Gly Arg Phe Thr Ile Ser
                85                  90                  95

Gln Asp Asn Ser Lys Asn Thr Val Tyr Leu Gln Met Asn Ser Leu Lys
            100                 105                 110

Pro Glu Asp Thr Ala Ile Tyr Tyr Cys Thr Leu Thr Thr Ala Asn Ser
        115                 120                 125

Arg Gly Phe Cys Ser Gly Gly Tyr Asn Tyr Lys Gly Gln Gly Thr Gln
    130                 135                 140

Val Thr Val Ser Gly Gly Thr Ser Gly Gly Gly Ser Gly Gly Gly Gly
145                 150                 155                 160
```

Gly Ser Gly Gly Gly Ser Ala Ala Arg Phe Pro Asn Ile Thr
         165             170             175

Asn Leu Cys Pro Phe Gly Glu Val Phe Asn Ala Thr Arg Phe Ala Ser
         180             185             190

Val Tyr Ala Trp Asn Arg Lys Arg Ile Ser Asn Cys Val Ala Asp Tyr
    195             200             205

Ser Val Leu Tyr Asn Ser Ala Ser Phe Ser Thr Phe Lys Cys Tyr Gly
210             215             220

Val Ser Pro Thr Lys Leu Asn Asp Leu Cys Phe Thr Asn Val Tyr Ala
225             230             235             240

Asp Ser Phe Val Ile Arg Gly Asp Glu Val Arg Gln Ile Ala Pro Gly
             245             250             255

Gln Thr Gly Lys Ile Ala Asp Tyr Asn Tyr Lys Leu Pro Asp Asp Phe
         260             265             270

Thr Gly Cys Val Ile Ala Trp Asn Ser Asn Asn Leu Asp Ser Lys Val
    275             280             285

Gly Gly Asn Tyr Asn Tyr Leu Tyr Arg Leu Phe Arg Lys Ser Asn Leu
290             295             300

Lys Pro Phe Glu Arg Asp Ile Ser Thr Glu Ile Tyr Gln Ala Gly Ser
305             310             315             320

Thr Pro Cys Asn Gly Val Glu Gly Phe Asn Cys Tyr Phe Pro Leu Gln
             325             330             335

Ser Tyr Gly Phe Gln Pro Thr Asn Gly Val Gly Tyr Gln Pro Tyr Arg
         340             345             350

Val Val Val Leu Ser Phe Glu Leu Leu His Ala Pro Ala Thr Val Cys
    355             360             365

Gly Pro Lys Lys Ser Thr Asn Leu Glu Phe Ser Gly Gly Gly Gly Ser
370             375             380

Gly Gly Gly Gly Ser Gly Gly Gly Ser Ala Ala Ala Gln Glu Cys
385             390             395             400

Ser Leu Gln Ser Cys Thr Gln His Gln Pro Tyr Val Val Asp Asp Pro
             405             410             415

Cys Pro Ile His Phe Tyr Ser Lys Trp Tyr Ile Arg Val Gly Ala Arg
         420             425             430

Lys Ser Ala Pro Leu Ile Glu Leu Cys Val Asp Glu Ala Gly Ser Lys
    435             440             445

Ser Pro Ile Gln Tyr Ile Asp Ile Gly Asn Tyr Thr Val Ser Cys Leu
450             455             460

Pro Phe Thr Ile Asn Cys Gln Glu Pro Lys Leu Gly Ser Leu Val Val
465             470             475             480

Arg Cys Ser Phe Tyr Glu Asp Phe Leu Glu Tyr His Asp Val Arg Val
             485             490             495

Val Leu Asp Phe Ile Pro Arg Gly Gly Ser Gly Gly Gly Ser Gly
         500             505             510

Gly Gly Ser Ala Trp Ser His Pro Gln Phe Glu Lys Gly Gly Ser
         515             520             525

Gly Gly Gly Ser Gly Gly Ser Ala Trp Ser His Pro Gln Phe Glu Lys
         530             535             540

<210> SEQ ID NO 9
<211> LENGTH: 810
<212> TYPE: DNA
<213> ORGANISM: Artificial Sequence
<220> FEATURE:
<223> OTHER INFORMATION: Synthetic

```
<220> FEATURE:
<221> NAME/KEY: CDS
<222> LOCATION: (1)..(810)

<400> SEQUENCE: 9 atg acc aac aag tgc ctg ctg cag att gcc ctg ctg tgc ttc agc      48
Met Thr Asn Lys Cys Leu Leu Gln Ile Ala Leu Leu Leu Cys Phe Ser
1               5                   10                  15 aca aca gcc ctg tct atg ggc gcg cct caa gtt cag ctt caa gaa tct  96
Thr Thr Ala Leu Ser Met Gly Ala Pro Gln Val Gln Leu Gln Glu Ser
                20                  25                  30 ggc ggc gga agc gtt cag gct ggc gga tct ctg aga ctg agc tgt gtg 144
Gly Gly Gly Ser Val Gln Ala Gly Gly Ser Leu Arg Leu Ser Cys Val
            35                  40                  45 gcc agc ggc tac acc gat agc aca tac tgc gtc ggc tgg ttc aga cag 192
Ala Ser Gly Tyr Thr Asp Ser Thr Tyr Cys Val Gly Trp Phe Arg Gln
        50                  55                  60 gcc cct ggc aaa gag aga gag ggc gtc gcc aga atc aac acc atc agc 240
Ala Pro Gly Lys Glu Arg Glu Gly Val Ala Arg Ile Asn Thr Ile Ser
65                  70                  75                  80 ggc aga cct tgg tac gcc gac tct gtg aag ggc aga ttc aca atc agc 288
Gly Arg Pro Trp Tyr Ala Asp Ser Val Lys Gly Arg Phe Thr Ile Ser
                85                  90                  95 cag gac aac agc aag aac acc gtg tac ctg cag atg aac agc ctg aag 336
Gln Asp Asn Ser Lys Asn Thr Val Tyr Leu Gln Met Asn Ser Leu Lys
            100                 105                 110 cct gag gac acc gcc atc tac tac tgc acc ctg acc acc gcc aac agc 384
Pro Glu Asp Thr Ala Ile Tyr Tyr Cys Thr Leu Thr Thr Ala Asn Ser
        115                 120                 125 aga ggc ttt tgt tcc ggc ggc tac aac tac aaa ggc cag ggc acc caa 432
Arg Gly Phe Cys Ser Gly Gly Tyr Asn Tyr Lys Gly Gln Gly Thr Gln
130                 135                 140 gtg acc gtg tct ggt ggt acc agc gga ggc gga gga tca ggt ggc gga 480
Val Thr Val Ser Gly Gly Thr Ser Gly Gly Gly Gly Ser Gly Gly Gly
145                 150                 155                 160 ggt agt ggt ggt ggc ggt agc gcg gcc gct atg gcc tac tgt tgg aga 528
Gly Ser Gly Gly Gly Gly Ser Ala Ala Ala Met Ala Tyr Cys Trp Arg
                165                 170                 175 tgc acc agc tgc tgc ttc agc gag cgg ttc cag aac cac aat cct cag 576
Cys Thr Ser Cys Cys Phe Ser Glu Arg Phe Gln Asn His Asn Pro Gln
            180                 185                 190 aaa gag atg gcc acc agc aca ctg cag ggc tgt tct ctg tgt ctg cag 624
Lys Glu Met Ala Thr Ser Thr Leu Gln Gly Cys Ser Leu Cys Leu Gln
        195                 200                 205 ctg gcc gtg gtg gtc aac tct ctg ctg acc cct ttc gcc aga tgc tgc 672
Leu Ala Val Val Val Asn Ser Leu Leu Thr Pro Phe Ala Arg Cys Cys
210                 215                 220 tgg cct gaa ttc ggc gga ggc agc ggc ggt gga agc ggc gga ggc tct 720
Trp Pro Glu Phe Gly Gly Gly Ser Gly Gly Gly Ser Gly Gly Gly Ser
225                 230                 235                 240 gct tgg agc cac ccg cag ttc gaa aaa ggt gga ggt tct ggc ggt gga 768
Ala Trp Ser His Pro Gln Phe Glu Lys Gly Gly Gly Ser Gly Gly Gly
                245                 250                 255 tcg gga ggt tca gcg tgg agc cac ccg cag ttc gag aaa tga          810
Ser Gly Gly Ser Ala Trp Ser His Pro Gln Phe Glu Lys
            260                 265

<210> SEQ ID NO 10
<211> LENGTH: 269
<212> TYPE: PRT
<213> ORGANISM: Artificial Sequence
```

<220> FEATURE:
<223> OTHER INFORMATION: Synthetic Construct

<400> SEQUENCE: 10

```
Met Thr Asn Lys Cys Leu Leu Gln Ile Ala Leu Leu Leu Cys Phe Ser
1               5                   10                  15

Thr Thr Ala Leu Ser Met Gly Ala Pro Gln Val Gln Leu Gln Glu Ser
            20                  25                  30

Gly Gly Gly Ser Val Gln Ala Gly Gly Ser Leu Arg Leu Ser Cys Val
        35                  40                  45

Ala Ser Gly Tyr Thr Asp Ser Thr Tyr Cys Val Gly Trp Phe Arg Gln
50                  55                  60

Ala Pro Gly Lys Glu Arg Glu Gly Val Ala Arg Ile Asn Thr Ile Ser
65                  70                  75                  80

Gly Arg Pro Trp Tyr Ala Asp Ser Val Lys Gly Arg Phe Thr Ile Ser
                85                  90                  95

Gln Asp Asn Ser Lys Asn Thr Val Tyr Leu Gln Met Asn Ser Leu Lys
            100                 105                 110

Pro Glu Asp Thr Ala Ile Tyr Tyr Cys Thr Leu Thr Thr Ala Asn Ser
        115                 120                 125

Arg Gly Phe Cys Ser Gly Gly Tyr Asn Tyr Lys Gly Gln Gly Thr Gln
130                 135                 140

Val Thr Val Ser Gly Gly Thr Ser Gly Gly Gly Ser Gly Gly Gly Gly
145                 150                 155                 160

Gly Ser Gly Gly Gly Gly Ser Ala Ala Ala Met Ala Tyr Cys Trp Arg
                165                 170                 175

Cys Thr Ser Cys Cys Phe Ser Glu Arg Phe Gln Asn His Asn Pro Gln
            180                 185                 190

Lys Glu Met Ala Thr Ser Thr Leu Gln Gly Cys Ser Leu Cys Leu Gln
        195                 200                 205

Leu Ala Val Val Val Asn Ser Leu Leu Thr Pro Phe Ala Arg Cys Cys
210                 215                 220

Trp Pro Glu Phe Gly Gly Gly Ser Gly Gly Gly Ser Gly Gly Gly Ser
225                 230                 235                 240

Ala Trp Ser His Pro Gln Phe Glu Lys Gly Gly Gly Ser Gly Gly Gly
                245                 250                 255

Ser Gly Gly Ser Ala Trp Ser His Pro Gln Phe Glu Lys
            260                 265
```

<210> SEQ ID NO 11
<211> LENGTH: 1491
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1491)

<400> SEQUENCE: 11

```
atg acc aac aag tgc ctg ctg cag att gcc ctg ctg ctg tgc ttc agc    48
Met Thr Asn Lys Cys Leu Leu Gln Ile Ala Leu Leu Leu Cys Phe Ser
1               5                   10                  15 aca aca gcc ctg tct atg ggc gcg cct caa gtt cag ctt caa gaa tct    96
Thr Thr Ala Leu Ser Met Gly Ala Pro Gln Val Gln Leu Gln Glu Ser
            20                  25                  30 ggc ggc gga agc gtt cag gct ggc gga tct ctg aga ctg agc tgt gtg   144
Gly Gly Gly Ser Val Gln Ala Gly Gly Ser Leu Arg Leu Ser Cys Val
```

```
                    35                  40                  45
gcc agc ggc tac acc gat agc aca tac tgc gtc ggc tgg ttc aga cag       192
Ala Ser Gly Tyr Thr Asp Ser Thr Tyr Cys Val Gly Trp Phe Arg Gln
 50                  55                  60 gcc cct ggc aaa gag aga gag ggc gtc gcc aga atc aac acc atc agc       240
Ala Pro Gly Lys Glu Arg Glu Gly Val Ala Arg Ile Asn Thr Ile Ser
 65                  70                  75                  80 ggc aga cct tgg tac gcc gac tct gtg aag ggc aga ttc aca atc agc       288
Gly Arg Pro Trp Tyr Ala Asp Ser Val Lys Gly Arg Phe Thr Ile Ser
                 85                  90                  95 cag gac aac agc aag aac acc gtg tac ctg cag atg aac agc ctg aag       336
Gln Asp Asn Ser Lys Asn Thr Val Tyr Leu Gln Met Asn Ser Leu Lys
            100                 105                 110 cct gag gac acc gcc atc tac tac tgc acc ctg acc acc gcc aac agc       384
Pro Glu Asp Thr Ala Ile Tyr Tyr Cys Thr Leu Thr Thr Ala Asn Ser
        115                 120                 125 aga ggc ttt tgt tcc ggc ggc tac aac tac aaa ggc cag ggc acc caa       432
Arg Gly Phe Cys Ser Gly Gly Tyr Asn Tyr Lys Gly Gln Gly Thr Gln
130                 135                 140 gtg acc gtg tct ggt ggt acc agc gga ggc gga gga tca ggt ggc gga       480
Val Thr Val Ser Gly Gly Thr Ser Gly Gly Gly Gly Ser Gly Gly Gly
145                 150                 155                 160 ggt agt ggt ggt ggc ggt agc gcg gcc gct aga ttc ccc aac atc acc       528
Gly Ser Gly Gly Gly Gly Ser Ala Ala Ala Arg Phe Pro Asn Ile Thr
                165                 170                 175 aat ctg tgc ccc ttc ggc gag gtg ttc aac gcc aca aga ttc gcc tct       576
Asn Leu Cys Pro Phe Gly Glu Val Phe Asn Ala Thr Arg Phe Ala Ser
            180                 185                 190 gtg tac gcc tgg aac cgg aag cgg atc agc aat tgc gtg gcc gac tac       624
Val Tyr Ala Trp Asn Arg Lys Arg Ile Ser Asn Cys Val Ala Asp Tyr
        195                 200                 205 agc gtg ctg tac aac agc gcc agc ttc tcc acc ttc aag tgc tac ggc       672
Ser Val Leu Tyr Asn Ser Ala Ser Phe Ser Thr Phe Lys Cys Tyr Gly
210                 215                 220 gtg tcc cct acc aag ctg aac gac ctg tgc ttt acc aac gtg tac gcc       720
Val Ser Pro Thr Lys Leu Asn Asp Leu Cys Phe Thr Asn Val Tyr Ala
225                 230                 235                 240 gat agc ttc gtg atc cgg gga gat gaa gtg cgg cag atc gct cct gga       768
Asp Ser Phe Val Ile Arg Gly Asp Glu Val Arg Gln Ile Ala Pro Gly
                245                 250                 255 cag aca ggc aag atc gcc gac tat aac tac aag ctg ccc gac gac ttc       816
Gln Thr Gly Lys Ile Ala Asp Tyr Asn Tyr Lys Leu Pro Asp Asp Phe
            260                 265                 270 acc ggc tgt gtg att gcc tgg aac agc aac aac ctg gac agc aaa gtc       864
Thr Gly Cys Val Ile Ala Trp Asn Ser Asn Asn Leu Asp Ser Lys Val
        275                 280                 285 ggc ggc aac tac aat tac ctg tac cgg ctg ttc cgg aag tcc aat ctg       912
Gly Gly Asn Tyr Asn Tyr Leu Tyr Arg Leu Phe Arg Lys Ser Asn Leu
290                 295                 300 aag ccc ttc gag cgg gac atc agc acc gag atc tat cag gcc ggc agc       960
Lys Pro Phe Glu Arg Asp Ile Ser Thr Glu Ile Tyr Gln Ala Gly Ser
305                 310                 315                 320 acc cct tgc aat ggc gtg gaa ggc ttc aac tgc tac ttc cca ctg cag      1008
Thr Pro Cys Asn Gly Val Glu Gly Phe Asn Cys Tyr Phe Pro Leu Gln
                325                 330                 335 tcc tac ggc ttc cag cct aca aac ggc gtg ggc tac cag cct tac aga      1056
Ser Tyr Gly Phe Gln Pro Thr Asn Gly Val Gly Tyr Gln Pro Tyr Arg
            340                 345                 350 gtg gtg gtc ctg agc ttc gag ctg ctg cat gcc cct gct aca gtg tgc      1104
```

```
                Val Val Val Leu Ser Phe Glu Leu Leu His Ala Pro Ala Thr Val Cys
                        355                 360                 365 ggc cct aag aag tct acc aac ctg gaa ttc tct ggc ggc gga gga tct        1152
Gly Pro Lys Lys Ser Thr Asn Leu Glu Phe Ser Gly Gly Gly Gly Ser
        370                 375                 380 ggc gga ggt gga agc gga ggc ggt gga tct gcg gcc gct atg gcc tac        1200
Gly Gly Gly Gly Ser Gly Gly Gly Gly Ser Ala Ala Ala Met Ala Tyr
385                 390                 395                 400 tgt tgg aga tgc acc agc tgc tgc ttc agc gag cgg ttc cag aac cac        1248
Cys Trp Arg Cys Thr Ser Cys Cys Phe Ser Glu Arg Phe Gln Asn His
                405                 410                 415 aat cct cag aaa gag atg gcc acc agc aca ctg cag ggc tgt tct ctg        1296
Asn Pro Gln Lys Glu Met Ala Thr Ser Thr Leu Gln Gly Cys Ser Leu
            420                 425                 430 tgt ctg cag ctg gcc gtg gtg gtc aac tct ctg ctg acc cct ttc gcc        1344
Cys Leu Gln Leu Ala Val Val Val Asn Ser Leu Leu Thr Pro Phe Ala
        435                 440                 445 aga tgc tgc tgg cct gaa ttc ggc gga ggc agc ggc ggt gga agc ggc        1392
Arg Cys Cys Trp Pro Glu Phe Gly Gly Gly Ser Gly Gly Gly Ser Gly
450                 455                 460 gga ggc tct gct tgg agc cac ccg cag ttc gaa aaa ggt gga ggt tct        1440
Gly Gly Ser Ala Trp Ser His Pro Gln Phe Glu Lys Gly Gly Gly Ser
465                 470                 475                 480 ggc ggt gga tcg gga ggt tca gcg tgg agc cac ccg cag ttc gag aaa        1488
Gly Gly Gly Ser Gly Gly Ser Ala Trp Ser His Pro Gln Phe Glu Lys
                485                 490                 495 tga                                                                     1491

<210> SEQ ID NO 12
<211> LENGTH: 496
<212> TYPE: PRT
<213> ORGANISM: Artificial Sequence
<220> FEATURE:
<223> OTHER INFORMATION: Synthetic Construct

<400> SEQUENCE: 12

Met Thr Asn Lys Cys Leu Leu Gln Ile Ala Leu Leu Leu Cys Phe Ser
1               5                   10                  15

Thr Thr Ala Leu Ser Met Gly Ala Pro Gln Val Gln Leu Gln Glu Ser
            20                  25                  30

Gly Gly Gly Ser Val Gln Ala Gly Gly Ser Leu Arg Leu Ser Cys Val
        35                  40                  45

Ala Ser Gly Tyr Thr Asp Ser Thr Tyr Cys Val Gly Trp Phe Arg Gln
    50                  55                  60

Ala Pro Gly Lys Glu Arg Glu Gly Val Ala Arg Ile Asn Thr Ile Ser
65                  70                  75                  80

Gly Arg Pro Trp Tyr Ala Asp Ser Val Lys Gly Arg Phe Thr Ile Ser
                85                  90                  95

Gln Asp Asn Ser Lys Asn Thr Val Tyr Leu Gln Met Asn Ser Leu Lys
            100                 105                 110

Pro Glu Asp Thr Ala Ile Tyr Tyr Cys Thr Leu Thr Thr Ala Asn Ser
        115                 120                 125

Arg Gly Phe Cys Ser Gly Gly Tyr Asn Tyr Lys Gly Gln Gly Thr Gln
    130                 135                 140

Val Thr Val Ser Gly Gly Thr Ser Gly Gly Gly Ser Gly Gly Gly Gly
145                 150                 155                 160

Gly Ser Gly Gly Gly Gly Ser Ala Ala Ala Arg Phe Pro Asn Ile Thr
                165                 170                 175
```

Asn Leu Cys Pro Phe Gly Glu Val Phe Asn Ala Thr Arg Phe Ala Ser
        180                 185                 190

Val Tyr Ala Trp Asn Arg Lys Arg Ile Ser Asn Cys Val Ala Asp Tyr
    195                 200                 205

Ser Val Leu Tyr Asn Ser Ala Ser Phe Ser Thr Phe Lys Cys Tyr Gly
    210                 215                 220

Val Ser Pro Thr Lys Leu Asn Asp Leu Cys Phe Thr Asn Val Tyr Ala
225                 230                 235                 240

Asp Ser Phe Val Ile Arg Gly Asp Glu Val Arg Gln Ile Ala Pro Gly
                245                 250                 255

Gln Thr Gly Lys Ile Ala Asp Tyr Asn Tyr Lys Leu Pro Asp Asp Phe
                260                 265                 270

Thr Gly Cys Val Ile Ala Trp Asn Ser Asn Asn Leu Asp Ser Lys Val
            275                 280                 285

Gly Gly Asn Tyr Asn Tyr Leu Tyr Arg Leu Phe Arg Lys Ser Asn Leu
        290                 295                 300

Lys Pro Phe Glu Arg Asp Ile Ser Thr Glu Ile Tyr Gln Ala Gly Ser
305                 310                 315                 320

Thr Pro Cys Asn Gly Val Glu Gly Phe Asn Cys Tyr Phe Pro Leu Gln
                325                 330                 335

Ser Tyr Gly Phe Gln Pro Thr Asn Gly Val Gly Tyr Gln Pro Tyr Arg
                340                 345                 350

Val Val Val Leu Ser Phe Glu Leu Leu His Ala Pro Ala Thr Val Cys
            355                 360                 365

Gly Pro Lys Lys Ser Thr Asn Leu Glu Phe Ser Gly Gly Gly Gly Ser
        370                 375                 380

Gly Gly Gly Gly Ser Gly Gly Gly Ser Ala Ala Ala Met Ala Tyr
385                 390                 395                 400

Cys Trp Arg Cys Thr Ser Cys Cys Phe Ser Glu Arg Phe Gln Asn His
                405                 410                 415

Asn Pro Gln Lys Glu Met Ala Thr Ser Thr Leu Gln Gly Cys Ser Leu
                420                 425                 430

Cys Leu Gln Leu Ala Val Val Val Asn Ser Leu Leu Thr Pro Phe Ala
            435                 440                 445

Arg Cys Cys Trp Pro Glu Phe Gly Gly Ser Gly Gly Gly Ser Gly
        450                 455                 460

Gly Gly Ser Ala Trp Ser His Pro Gln Phe Glu Lys Gly Gly Gly Ser
465                 470                 475                 480

Gly Gly Gly Ser Gly Gly Ser Ala Trp Ser His Pro Gln Phe Glu Lys
                485                 490                 495

<210> SEQ ID NO 13
<211> LENGTH: 579
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(579)

<400> SEQUENCE: 13 atg acc aac aag tgc ctg ctg cag att gcc ctg ctg ctg tgc ttc agc      48
Met Thr Asn Lys Cys Leu Leu Gln Ile Ala Leu Leu Leu Cys Phe Ser
1               5                   10                  15 aca aca gcc ctg tct atg ggc gcg cct caa gtt cag ctt caa gaa tct      96

```
Thr Thr Ala Leu Ser Met Gly Ala Pro Gln Val Gln Leu Gln Glu Ser
         20                  25                  30 ggc gga gga agc gtt cag gct gga gga tct ctg aga ctg agc tgt gtg      144
Gly Gly Gly Ser Val Gln Ala Gly Gly Ser Leu Arg Leu Ser Cys Val
         35                  40                  45 gcc agc ggc tac acc gat agc aca tac tgc gtc ggc tgg ttc aga cag      192
Ala Ser Gly Tyr Thr Asp Ser Thr Tyr Cys Val Gly Trp Phe Arg Gln
 50                  55                  60 gcc cct ggc aaa gag aga gag ggc gtc gcc aga atc aac acc atc agc      240
Ala Pro Gly Lys Glu Arg Glu Gly Val Ala Arg Ile Asn Thr Ile Ser
 65                  70                  75                  80 ggc aga cct tgg tac gcc gac tct gtg aag ggc aga ttc aca atc agc      288
Gly Arg Pro Trp Tyr Ala Asp Ser Val Lys Gly Arg Phe Thr Ile Ser
                 85                  90                  95 cag gac aac agc aag aac acc gtg tac ctg cag atg aac agc ctg aag      336
Gln Asp Asn Ser Lys Asn Thr Val Tyr Leu Gln Met Asn Ser Leu Lys
            100                 105                 110 cct gag gac acc gcc atc tac tac tgc acc ctg acc acc gcc aac agc      384
Pro Glu Asp Thr Ala Ile Tyr Tyr Cys Thr Leu Thr Thr Ala Asn Ser
        115                 120                 125 aga ggc ttt tgt tcc ggc ggc tac aac tac aaa ggc cag ggc acc caa      432
Arg Gly Phe Cys Ser Gly Gly Tyr Asn Tyr Lys Gly Gln Gly Thr Gln
130                 135                 140 gtg acc gtg tct ggt gaa ttc ggc gga ggc agc ggc ggt gga agc ggc      480
Val Thr Val Ser Gly Glu Phe Gly Gly Gly Ser Gly Gly Gly Ser Gly
145                 150                 155                 160 gga ggc tct gct tgg agc cac ccg cag ttc gaa aaa ggt gga ggt tct      528
Gly Gly Ser Ala Trp Ser His Pro Gln Phe Glu Lys Gly Gly Gly Ser
                165                 170                 175 ggc ggt gga tcg gga ggt tca gcg tgg agc cac ccg cag ttc gag aaa      576
Gly Gly Gly Ser Gly Gly Ser Ala Trp Ser His Pro Gln Phe Glu Lys
            180                 185                 190 tga                                                                   579
```

<210> SEQ ID NO 14
<211> LENGTH: 192
<212> TYPE: PRT
<213> ORGANISM: Artificial Sequence
<220> FEATURE:
<223> OTHER INFORMATION: Synthetic Construct

<400> SEQUENCE: 14

```
Met Thr Asn Lys Cys Leu Leu Gln Ile Ala Leu Leu Leu Cys Phe Ser
 1               5                  10                  15

Thr Thr Ala Leu Ser Met Gly Ala Pro Gln Val Gln Leu Gln Glu Ser
             20                  25                  30

Gly Gly Gly Ser Val Gln Ala Gly Gly Ser Leu Arg Leu Ser Cys Val
         35                  40                  45

Ala Ser Gly Tyr Thr Asp Ser Thr Tyr Cys Val Gly Trp Phe Arg Gln
 50                  55                  60

Ala Pro Gly Lys Glu Arg Glu Gly Val Ala Arg Ile Asn Thr Ile Ser
 65                  70                  75                  80

Gly Arg Pro Trp Tyr Ala Asp Ser Val Lys Gly Arg Phe Thr Ile Ser
                 85                  90                  95

Gln Asp Asn Ser Lys Asn Thr Val Tyr Leu Gln Met Asn Ser Leu Lys
            100                 105                 110

Pro Glu Asp Thr Ala Ile Tyr Tyr Cys Thr Leu Thr Thr Ala Asn Ser
        115                 120                 125
```

```
                    Arg Gly Phe Cys Ser Gly Gly Tyr Asn Tyr Lys Gly Gln Gly Thr Gln
                        130                 135                 140

Val Thr Val Ser Gly Glu Phe Gly Gly Ser Gly Gly Gly Ser Gly
                    145                 150                 155                 160

Gly Gly Ser Ala Trp Ser His Pro Gln Phe Glu Lys Gly Gly Gly Ser
                                    165                 170                 175

Gly Gly Gly Ser Gly Gly Ser Ala Trp Ser His Pro Gln Phe Glu Lys
                                    180                 185                 190

<210> SEQ ID NO 15
<211> LENGTH: 1776
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1776)

<400> SEQUENCE: 15 atg acc aac aag tgc ctg ctg cag att gcc ctg ctg ctg tgc ttc agc      48
Met Thr Asn Lys Cys Leu Leu Gln Ile Ala Leu Leu Leu Cys Phe Ser
1               5                   10                  15 aca aca gcc ctg tct atg ggc gcg cct cag gtt cag ctg gtt gaa tct      96
Thr Thr Ala Leu Ser Met Gly Ala Pro Gln Val Gln Leu Val Glu Ser
            20                  25                  30 ggc gga ggc ctg atg caa gct ggc gga tct ctg aga ctg agc tgt gcc     144
Gly Gly Gly Leu Met Gln Ala Gly Gly Ser Leu Arg Leu Ser Cys Ala
        35                  40                  45 gtg tcc ggc aga acc ttt tct aca gcc gcc atg ggc tgg ttc aga cag     192
Val Ser Gly Arg Thr Phe Ser Thr Ala Ala Met Gly Trp Phe Arg Gln
    50                  55                  60 gcc cct gga aaa gaa cgc gag ttc gtg gcc gct atc cgt tgg agc gga     240
Ala Pro Gly Lys Glu Arg Glu Phe Val Ala Ala Ile Arg Trp Ser Gly
65                  70                  75                  80 ggc tct gcc tac tac gcc gat tct gtg aag ggc aga ttc acc atc agc     288
Gly Ser Ala Tyr Tyr Ala Asp Ser Val Lys Gly Arg Phe Thr Ile Ser
                85                  90                  95 aga gac aag gcc aag aac acc gtg tac ctg cag atg aac agc ctg aag     336
Arg Asp Lys Ala Lys Asn Thr Val Tyr Leu Gln Met Asn Ser Leu Lys
            100                 105                 110 tac gag gac acc gcc gtg tac tac tgc gcc aga aca gag aat gtg cgg     384
Tyr Glu Asp Thr Ala Val Tyr Tyr Cys Ala Arg Thr Glu Asn Val Arg
        115                 120                 125 agc ctg ctg agc gac tac gcc acc tgg cct tac gat tat tgg ggc cag     432
Ser Leu Leu Ser Asp Tyr Ala Thr Trp Pro Tyr Asp Tyr Trp Gly Gln
    130                 135                 140 ggc acc caa gtg acc gtt tct ggt ggc gga gga agc gga ggc gga gga     480
Gly Thr Gln Val Thr Val Ser Gly Gly Gly Gly Ser Gly Gly Gly Gly
145                 150                 155                 160 tca ggt ggc ggt gga tct atc gat cag gtg cag ctc gtg gaa agc ggt     528
Ser Gly Gly Gly Gly Ser Ile Asp Gln Val Gln Leu Val Glu Ser Gly
                165                 170                 175 ggc gga ctt atg cag gca ggc gga agc ctg aga ctg tct tgt gct gtg     576
Gly Gly Leu Met Gln Ala Gly Gly Ser Leu Arg Leu Ser Cys Ala Val
            180                 185                 190 tct ggc cgg acc ttt agc acc gct gct atg gga tgg ttt agg cag gct     624
Ser Gly Arg Thr Phe Ser Thr Ala Ala Met Gly Trp Phe Arg Gln Ala
        195                 200                 205 cca ggc aaa gaa agg gaa ttt gtg gcc gcc att cgt tgg agt ggc ggc     672
Pro Gly Lys Glu Arg Glu Phe Val Ala Ala Ile Arg Trp Ser Gly Gly
```

```
                 210                 215                 220
agc gcc tat tat gcc gat agc gtg aaa ggc cgg ttc acc atc tct cgc      720
Ser Ala Tyr Tyr Ala Asp Ser Val Lys Gly Arg Phe Thr Ile Ser Arg
225                 230                 235                 240 gat aag gct aag aat acg gtc tat ctc cag atg aac tcc ctc aaa tat      768
Asp Lys Ala Lys Asn Thr Val Tyr Leu Gln Met Asn Ser Leu Lys Tyr
                    245                 250                 255 gag gat acg gcc gtc tac tat tgt gcc cgg acc gaa aat gtg cgc tcc      816
Glu Asp Thr Ala Val Tyr Tyr Cys Ala Arg Thr Glu Asn Val Arg Ser
            260                 265                 270 ctg ctg tct gat tat gcc aca tgg ccc tat gac tac tgg gga cag gga      864
Leu Leu Ser Asp Tyr Ala Thr Trp Pro Tyr Asp Tyr Trp Gly Gln Gly
                275                 280                 285 aca caa gtc aca gtg tcc agc ggt acc ggc gga ggt gga agc gga ggc      912
Thr Gln Val Thr Val Ser Ser Gly Thr Gly Gly Gly Gly Ser Gly Gly
        290                 295                 300 gga ggc tct ggc ggc ggt gga tct gga tcc gag cct aag agc tgc gac      960
Gly Gly Ser Gly Gly Gly Gly Ser Gly Ser Glu Pro Lys Ser Cys Asp
305                 310                 315                 320 aag acc cac acc tgt cct cca tgt cct gct cca gaa ctg ctc ggc gga     1008
Lys Thr His Thr Cys Pro Pro Cys Pro Ala Pro Glu Leu Leu Gly Gly
                    325                 330                 335 cct tcc gtg ttc ctg ttt cct cca aag cct aag gac acc ctg atg atc     1056
Pro Ser Val Phe Leu Phe Pro Pro Lys Pro Lys Asp Thr Leu Met Ile
            340                 345                 350 agc aga acc cct gaa gtg acc tgc gtg gtg gtg gat gtg tcc cac gaa     1104
Ser Arg Thr Pro Glu Val Thr Cys Val Val Val Asp Val Ser His Glu
                355                 360                 365 gat ccc gaa gtg aag ttc aat tgg tac gtg gac ggc gtg gaa gtg cac     1152
Asp Pro Glu Val Lys Phe Asn Trp Tyr Val Asp Gly Val Glu Val His
370                 375                 380 aac gcc aag acc aag cct aga gag gaa cag tac aac agc acc tac aga     1200
Asn Ala Lys Thr Lys Pro Arg Glu Glu Gln Tyr Asn Ser Thr Tyr Arg
385                 390                 395                 400 gtg gtg tcc gtg ctg acc gtg ctg cac cag gat tgg ctg aac ggc aaa     1248
Val Val Ser Val Leu Thr Val Leu His Gln Asp Trp Leu Asn Gly Lys
                    405                 410                 415 gag tac aag tgc aag gtg tcc aac aag gcc ctg cct gct cct atc gag     1296
Glu Tyr Lys Cys Lys Val Ser Asn Lys Ala Leu Pro Ala Pro Ile Glu
            420                 425                 430 aaa acc atc agc aag gcc aag ggc cag cct agg gaa ccc cag gtt tac     1344
Lys Thr Ile Ser Lys Ala Lys Gly Gln Pro Arg Glu Pro Gln Val Tyr
                435                 440                 445 aca ctg cct cca agc cgg gaa gag atg acc aag aac cag gtg tcc ctg     1392
Thr Leu Pro Pro Ser Arg Glu Glu Met Thr Lys Asn Gln Val Ser Leu
450                 455                 460 acc tgc ctg gtc aag ggc ttc tac cct tcc gat atc gcc gtg gaa tgg     1440
Thr Cys Leu Val Lys Gly Phe Tyr Pro Ser Asp Ile Ala Val Glu Trp
465                 470                 475                 480 gag agc aat ggc cag cct gag aac aac tac aag aca acc cct cct gtg     1488
Glu Ser Asn Gly Gln Pro Glu Asn Asn Tyr Lys Thr Thr Pro Pro Val
                    485                 490                 495 ctg gac agc gac ggc tca ttc ttc ctg tat agc aag ctg aca gtg gac     1536
Leu Asp Ser Asp Gly Ser Phe Phe Leu Tyr Ser Lys Leu Thr Val Asp
            500                 505                 510 aag agc aga tgg cag cag ggc aac gtg ttc agc tgc agc gtg atg cac     1584
Lys Ser Arg Trp Gln Gln Gly Asn Val Phe Ser Cys Ser Val Met His
                515                 520                 525 gag gcc ctg cac aac cac tac acc cag aag tcc ctg agc ctg tct cct     1632
```

```
                Glu Ala Leu His Asn His Tyr Thr Gln Lys Ser Leu Ser Leu Ser Pro
                                530                 535                 540 ggc aag ccg cgg ggt ggt ggt tcc ggc gga ggt agt ggc ggc gga tct       1680
Gly Lys Pro Arg Gly Gly Gly Ser Gly Gly Gly Ser Gly Gly Gly Ser
545                 550                 555                 560 gcg gcc gct tgg agc cat cct cag ttc gag aaa ggc gga agc ggc           1728
Ala Ala Ala Trp Ser His Pro Gln Phe Glu Lys Gly Gly Ser Gly
                565                 570                 575 gga ggc agc ggt ggt ggc tct tgg tca cat ccc cag ttt gag aag tga       1776
Gly Gly Ser Gly Gly Gly Ser Trp Ser His Pro Gln Phe Glu Lys
580                 585                 590
```

<210> SEQ ID NO 16
<211> LENGTH: 591
<212> TYPE: PRT
<213> ORGANISM: Artificial Sequence
<220> FEATURE:
<223> OTHER INFORMATION: Synthetic Construct

<400> SEQUENCE: 16

```
Met Thr Asn Lys Cys Leu Leu Gln Ile Ala Leu Leu Leu Cys Phe Ser
1               5                   10                  15

Thr Thr Ala Leu Ser Met Gly Ala Pro Gln Val Gln Leu Val Glu Ser
            20                  25                  30

Gly Gly Gly Leu Met Gln Ala Gly Gly Ser Leu Arg Leu Ser Cys Ala
        35                  40                  45

Val Ser Gly Arg Thr Phe Ser Thr Ala Ala Met Gly Trp Phe Arg Gln
    50                  55                  60

Ala Pro Gly Lys Glu Arg Glu Phe Val Ala Ala Ile Arg Trp Ser Gly
65                  70                  75                  80

Gly Ser Ala Tyr Tyr Ala Asp Ser Val Lys Gly Arg Phe Thr Ile Ser
                85                  90                  95

Arg Asp Lys Ala Lys Asn Thr Val Tyr Leu Gln Met Asn Ser Leu Lys
            100                 105                 110

Tyr Glu Asp Thr Ala Val Tyr Tyr Cys Ala Arg Thr Glu Asn Val Arg
        115                 120                 125

Ser Leu Leu Ser Asp Tyr Ala Thr Trp Pro Tyr Asp Tyr Trp Gly Gln
    130                 135                 140

Gly Thr Gln Val Thr Val Ser Gly Gly Gly Ser Gly Gly Gly Gly
145                 150                 155                 160

Ser Gly Gly Gly Gly Ser Ile Asp Gln Val Gln Leu Val Glu Ser Gly
                165                 170                 175

Gly Gly Leu Met Gln Ala Gly Gly Ser Leu Arg Leu Ser Cys Ala Val
            180                 185                 190

Ser Gly Arg Thr Phe Ser Thr Ala Ala Met Gly Trp Phe Arg Gln Ala
        195                 200                 205

Pro Gly Lys Glu Arg Glu Phe Val Ala Ala Ile Arg Trp Ser Gly Gly
    210                 215                 220

Ser Ala Tyr Tyr Ala Asp Ser Val Lys Gly Arg Phe Thr Ile Ser Arg
225                 230                 235                 240

Asp Lys Ala Lys Asn Thr Val Tyr Leu Gln Met Asn Ser Leu Lys Tyr
                245                 250                 255

Glu Asp Thr Ala Val Tyr Tyr Cys Ala Arg Thr Glu Asn Val Arg Ser
            260                 265                 270

Leu Leu Ser Asp Tyr Ala Thr Trp Pro Tyr Asp Tyr Trp Gly Gln Gly
        275                 280                 285
```

```
Thr Gln Val Thr Val Ser Ser Gly Thr Gly Gly Gly Ser Gly Gly
    290                 295                 300
Gly Gly Ser Gly Gly Gly Ser Gly Ser Glu Pro Lys Ser Cys Asp
305                 310                 315                 320
Lys Thr His Thr Cys Pro Pro Cys Pro Ala Pro Glu Leu Leu Gly Gly
                325                 330                 335
Pro Ser Val Phe Leu Phe Pro Pro Lys Pro Lys Asp Thr Leu Met Ile
                340                 345                 350
Ser Arg Thr Pro Glu Val Thr Cys Val Val Val Asp Val Ser His Glu
                355                 360                 365
Asp Pro Glu Val Lys Phe Asn Trp Tyr Val Asp Gly Val Glu Val His
370                 375                 380
Asn Ala Lys Thr Lys Pro Arg Glu Glu Gln Tyr Asn Ser Thr Tyr Arg
385                 390                 395                 400
Val Val Ser Val Leu Thr Val Leu His Gln Asp Trp Leu Asn Gly Lys
                405                 410                 415
Glu Tyr Lys Cys Lys Val Ser Asn Lys Ala Leu Pro Ala Pro Ile Glu
                420                 425                 430
Lys Thr Ile Ser Lys Ala Lys Gly Gln Pro Arg Glu Pro Gln Val Tyr
                435                 440                 445
Thr Leu Pro Pro Ser Arg Glu Glu Met Thr Lys Asn Gln Val Ser Leu
450                 455                 460
Thr Cys Leu Val Lys Gly Phe Tyr Pro Ser Asp Ile Ala Val Glu Trp
465                 470                 475                 480
Glu Ser Asn Gly Gln Pro Glu Asn Asn Tyr Lys Thr Thr Pro Pro Val
                485                 490                 495
Leu Asp Ser Asp Gly Ser Phe Phe Leu Tyr Ser Lys Leu Thr Val Asp
                500                 505                 510
Lys Ser Arg Trp Gln Gln Gly Asn Val Phe Ser Cys Ser Val Met His
                515                 520                 525
Glu Ala Leu His Asn His Tyr Thr Gln Lys Ser Leu Ser Leu Ser Pro
530                 535                 540
Gly Lys Pro Arg Gly Gly Gly Ser Gly Gly Gly Ser Gly Gly Gly Ser
545                 550                 555                 560
Ala Ala Ala Trp Ser His Pro Gln Phe Glu Lys Gly Gly Gly Ser Gly
                565                 570                 575
Gly Gly Ser Gly Gly Gly Ser Trp Ser His Pro Gln Phe Glu Lys
                580                 585                 590

<210> SEQ ID NO 17
<211> LENGTH: 1215
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1215)

<400> SEQUENCE: 17 atg acc aac aag tgc ctg ctg cag att gcc ctg ctg ctg tgc ttc agc    48
Met Thr Asn Lys Cys Leu Leu Gln Ile Ala Leu Leu Leu Cys Phe Ser
1               5                   10                  15 aca aca gcc ctg tct atg ggc gcg cct cag gtt cag ctg gtt gaa tct    96
Thr Thr Ala Leu Ser Met Gly Ala Pro Gln Val Gln Leu Val Glu Ser
            20                  25                  30 ggc gga ggc ctg atg caa gct ggc gga tct ctg aga ctg agc tgt gcc   144
```

|     |     |     |     |     |     |     |     |     |     |     |     |     |     |     |     |     |
|---|---|---|---|---|---|---|---|---|---|---|---|---|---|---|---|---|
| Gly | Gly | Gly<br>35 | Leu | Met | Gln | Ala<br>40 | Gly | Gly | Ser | Leu<br>45 | Arg | Leu | Ser | Cys | Ala | |

| gtg | tcc | ggc | aga | acc | ttt | tct | aca | gcc | gcc | atg | ggc | tgg | ttc | aga | cag | 192 |
|---|---|---|---|---|---|---|---|---|---|---|---|---|---|---|---|---|
| Val | Ser<br>50 | Gly | Arg | Thr | Phe | Ser<br>55 | Thr | Ala | Ala | Met | Gly<br>60 | Trp | Phe | Arg | Gln | |

| gcc | cct | gga | aaa | gaa | cgc | gag | ttc | gtg | gcc | gct | atc | cgt | tgg | agc | gga | 240 |
|---|---|---|---|---|---|---|---|---|---|---|---|---|---|---|---|---|
| Ala<br>65 | Pro | Gly | Lys | Glu<br>70 | Arg | Glu | Phe | Val | Ala<br>75 | Ala | Ile | Arg | Trp | Ser<br>80 | Gly | |

| ggc | tct | gcc | tac | tac | gcc | gat | tct | gtg | aag | ggc | aga | ttc | acc | atc | agc | 288 |
|---|---|---|---|---|---|---|---|---|---|---|---|---|---|---|---|---|
| Gly | Ser | Ala | Tyr | Tyr<br>85 | Ala | Asp | Ser | Val | Lys<br>90 | Gly | Arg | Phe | Thr | Ile<br>95 | Ser | |

| aga | gac | aag | gcc | aag | aac | acc | gtg | tac | ctg | cag | atg | aac | agc | ctg | aag | 336 |
|---|---|---|---|---|---|---|---|---|---|---|---|---|---|---|---|---|
| Arg | Asp | Lys | Ala<br>100 | Lys | Asn | Thr | Val | Tyr<br>105 | Leu | Gln | Met | Asn | Ser<br>110 | Leu | Lys | |

| tac | gag | gac | acc | gcc | gtg | tac | tac | tgc | gcc | aga | aca | gag | aat | gtg | cgg | 384 |
|---|---|---|---|---|---|---|---|---|---|---|---|---|---|---|---|---|
| Tyr | Glu | Asp | Thr | Ala<br>115 | Val | Tyr | Tyr | Cys | Ala<br>120 | Arg | Thr | Glu | Asn | Val<br>125 | Arg | |

| agc | ctg | ctg | agc | gac | tac | gcc | acc | tgg | cct | tac | gat | tat | tgg | ggc | cag | 432 |
|---|---|---|---|---|---|---|---|---|---|---|---|---|---|---|---|---|
| Ser | Leu | Leu<br>130 | Ser | Asp | Tyr | Ala | Thr<br>135 | Trp | Pro | Tyr | Asp | Tyr<br>140 | Trp | Gly | Gln | |

| ggc | acc | caa | gtg | acc | gtt | tct | ggt | ggc | gga | gga | agc | gga | ggc | gga | gga | 480 |
|---|---|---|---|---|---|---|---|---|---|---|---|---|---|---|---|---|
| Gly<br>145 | Thr | Gln | Val | Thr | Val<br>150 | Ser | Gly | Gly | Gly | Gly<br>155 | Ser | Gly | Gly | Gly | Gly<br>160 | |

| tca | ggt | ggc | ggt | gga | tct | atc | gat | cag | gtg | cag | ctc | gtg | gaa | agc | ggt | 528 |
|---|---|---|---|---|---|---|---|---|---|---|---|---|---|---|---|---|
| Ser | Gly | Gly | Gly | Gly<br>165 | Ser | Ile | Asp | Gln | Val<br>170 | Gln | Leu | Val | Glu | Ser<br>175 | Gly | |

| ggc | gga | ctt | atg | cag | gca | ggc | gga | agc | ctg | aga | ctg | tct | tgt | gct | gtg | 576 |
|---|---|---|---|---|---|---|---|---|---|---|---|---|---|---|---|---|
| Gly | Gly | Leu | Met<br>180 | Gln | Ala | Gly | Gly | Ser<br>185 | Leu | Arg | Leu | Ser | Cys<br>190 | Ala | Val | |

| tct | ggc | cgg | acc | ttt | agc | acc | gct | gct | atg | gga | tgg | ttt | agg | cag | gct | 624 |
|---|---|---|---|---|---|---|---|---|---|---|---|---|---|---|---|---|
| Ser | Gly | Arg<br>195 | Thr | Phe | Ser | Thr | Ala<br>200 | Ala | Met | Gly | Trp | Phe<br>205 | Arg | Gln | Ala | |

| cca | ggc | aaa | gaa | agg | gaa | ttt | gtg | gcc | gcc | att | cgt | tgg | agt | ggc | ggc | 672 |
|---|---|---|---|---|---|---|---|---|---|---|---|---|---|---|---|---|
| Pro | Gly<br>210 | Lys | Glu | Arg | Glu | Phe<br>215 | Val | Ala | Ala | Ile | Arg<br>220 | Trp | Ser | Gly | Gly | |

| agc | gcc | tat | tat | gcc | gat | agc | gtg | aaa | ggc | cgg | ttc | acc | atc | tct | cgc | 720 |
|---|---|---|---|---|---|---|---|---|---|---|---|---|---|---|---|---|
| Ser | Ala<br>225 | Tyr | Tyr | Ala | Asp<br>230 | Ser | Val | Lys | Gly | Arg<br>235 | Phe | Thr | Ile | Ser | Arg<br>240 | |

| gat | aag | gct | aag | aat | acg | gtc | tat | ctc | cag | atg | aac | tcc | ctc | aaa | tat | 768 |
|---|---|---|---|---|---|---|---|---|---|---|---|---|---|---|---|---|
| Asp | Lys | Ala | Lys | Asn<br>245 | Thr | Val | Tyr | Leu | Gln<br>250 | Met | Asn | Ser | Leu | Lys<br>255 | Tyr | |

| gag | gat | acg | gcc | gtc | tac | tat | tgt | gcc | cgg | acc | gaa | aat | gtg | cgc | tcc | 816 |
|---|---|---|---|---|---|---|---|---|---|---|---|---|---|---|---|---|
| Glu | Asp | Thr | Ala | Val<br>260 | Tyr | Tyr | Cys | Ala | Arg<br>265 | Thr | Glu | Asn | Val | Arg<br>270 | Ser | |

| ctg | ctg | tct | gat | tat | gcc | aca | tgg | ccc | tat | gac | tac | tgg | gga | cag | gga | 864 |
|---|---|---|---|---|---|---|---|---|---|---|---|---|---|---|---|---|
| Leu | Leu | Ser | Asp<br>275 | Tyr | Ala | Thr | Trp | Pro<br>280 | Tyr | Asp | Tyr | Trp | Gly<br>285 | Gln | Gly | |

| aca | caa | gtc | aca | gtg | tcc | agc | ggt | acc | gag | cct | aag | atc | cct | cag | cct | 912 |
|---|---|---|---|---|---|---|---|---|---|---|---|---|---|---|---|---|
| Thr | Gln | Val | Thr | Val<br>290 | Ser | Ser | Gly | Thr | Glu<br>295 | Pro | Lys | Ile | Pro | Gln<br>300 | Pro | |

| cag | cca | aag | cct | caa | cca | caa | ccg | cag | cca | cag | cct | aaa | ccg | cag | cct | 960 |
|---|---|---|---|---|---|---|---|---|---|---|---|---|---|---|---|---|
| Gln | Pro<br>305 | Lys | Pro | Gln | Pro | Gln<br>310 | Pro | Gln | Pro | Gln | Pro<br>315 | Lys | Pro | Gln | Pro<br>320 | |

| aag | cca | gag | cct | gag | cag | cgg | atg | aag | cag | atc | gag | gac | aag | atc | gaa | 1008 |
|---|---|---|---|---|---|---|---|---|---|---|---|---|---|---|---|---|
| Lys | Pro | Glu | Pro | Glu<br>325 | Gln | Arg | Met | Lys | Gln<br>330 | Ile | Glu | Asp | Lys | Ile<br>335 | Glu | |

| gag | atc | ctg | agc | aaa | atc | tac | cac | atc | gag | aac | gag | atc | gcc | cgg | atc | 1056 |
|---|---|---|---|---|---|---|---|---|---|---|---|---|---|---|---|---|
| Glu | Ile | Leu | Ser | Lys<br>340 | Ile | Tyr | His | Ile | Glu<br>345 | Asn | Glu | Ile | Ala<br>350 | Arg | Ile | |

-continued

```
aag aag ctc gtc ggc gaa aga ccg cgg ggt ggt ggt tcc ggc gga ggt       1104
Lys Lys Leu Val Gly Glu Arg Pro Arg Gly Gly Gly Ser Gly Gly Gly
        355                 360                 365 agt ggc ggc gga tct gcg gcc gct tgg agc cat cct cag ttc gag aaa       1152
Ser Gly Gly Gly Ser Ala Ala Ala Trp Ser His Pro Gln Phe Glu Lys
370                 375                 380 ggc gga gga agc ggc gga ggc agc ggt ggt ggc tct tgg tca cat ccc       1200
Gly Gly Gly Ser Gly Gly Gly Ser Gly Gly Gly Ser Trp Ser His Pro
385                 390                 395                 400 cag ttt gag aag tga                                                    1215
Gln Phe Glu Lys
```

<210> SEQ ID NO 18
<211> LENGTH: 404
<212> TYPE: PRT
<213> ORGANISM: Artificial Sequence
<220> FEATURE:
<223> OTHER INFORMATION: Synthetic Construct

<400> SEQUENCE: 18

```
Met Thr Asn Lys Cys Leu Leu Gln Ile Ala Leu Leu Cys Phe Ser
1               5                   10                  15

Thr Thr Ala Leu Ser Met Gly Ala Pro Gln Val Gln Leu Val Glu Ser
            20                  25                  30

Gly Gly Gly Leu Met Gln Ala Gly Gly Ser Leu Arg Leu Ser Cys Ala
        35                  40                  45

Val Ser Gly Arg Thr Phe Ser Thr Ala Ala Met Gly Trp Phe Arg Gln
    50                  55                  60

Ala Pro Gly Lys Glu Arg Glu Phe Val Ala Ala Ile Arg Trp Ser Gly
65                  70                  75                  80

Gly Ser Ala Tyr Tyr Ala Asp Ser Val Lys Gly Arg Phe Thr Ile Ser
                85                  90                  95

Arg Asp Lys Ala Lys Asn Thr Val Tyr Leu Gln Met Asn Ser Leu Lys
            100                 105                 110

Tyr Glu Asp Thr Ala Val Tyr Tyr Cys Ala Arg Thr Glu Asn Val Arg
        115                 120                 125

Ser Leu Leu Ser Asp Tyr Ala Thr Trp Pro Tyr Asp Tyr Trp Gly Gln
    130                 135                 140

Gly Thr Gln Val Thr Val Ser Gly Gly Gly Ser Gly Gly Gly Gly
145                 150                 155                 160

Ser Gly Gly Gly Gly Ser Ile Asp Gln Val Gln Leu Val Glu Ser Gly
                165                 170                 175

Gly Gly Leu Met Gln Ala Gly Gly Ser Leu Arg Leu Ser Cys Ala Val
            180                 185                 190

Ser Gly Arg Thr Phe Ser Thr Ala Ala Met Gly Trp Phe Arg Gln Ala
        195                 200                 205

Pro Gly Lys Glu Arg Glu Phe Val Ala Ala Ile Arg Trp Ser Gly Gly
    210                 215                 220

Ser Ala Tyr Tyr Ala Asp Ser Val Lys Gly Arg Phe Thr Ile Ser Arg
225                 230                 235                 240

Asp Lys Ala Lys Asn Thr Val Tyr Leu Gln Met Asn Ser Leu Lys Tyr
                245                 250                 255

Glu Asp Thr Ala Val Tyr Tyr Cys Ala Arg Thr Glu Asn Val Arg Ser
            260                 265                 270

Leu Leu Ser Asp Tyr Ala Thr Trp Pro Tyr Asp Tyr Trp Gly Gln Gly
        275                 280                 285
```

```
Thr Gln Val Thr Val Ser Ser Gly Thr Glu Pro Lys Ile Pro Gln Pro
    290                 295                 300

Gln Pro Lys Pro Gln Pro Gln Pro Gln Pro Lys Pro Gln Pro
305                 310                 315                 320

Lys Pro Glu Pro Glu Gln Arg Met Lys Gln Ile Glu Asp Lys Ile Glu
                325                 330                 335

Glu Ile Leu Ser Lys Ile Tyr His Ile Glu Asn Glu Ile Ala Arg Ile
                340                 345                 350

Lys Lys Leu Val Gly Glu Arg Pro Arg Gly Gly Ser Gly Gly Gly
            355                 360                 365

Ser Gly Gly Gly Ser Ala Ala Ala Trp Ser His Pro Gln Phe Glu Lys
    370                 375                 380

Gly Gly Gly Ser Gly Gly Gly Ser Gly Gly Gly Ser Trp Ser His Pro
385                 390                 395                 400

Gln Phe Glu Lys

<210> SEQ ID NO 19
<211> LENGTH: 66
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(66)

<400> SEQUENCE: 19 atg acc aac aag tgc ctg ctg cag att gcc ctg ctg ctg tgc ttc agc      48
Met Thr Asn Lys Cys Leu Leu Gln Ile Ala Leu Leu Leu Cys Phe Ser
1               5                   10                  15 aca aca gcc ctg tct atg                                              66
Thr Thr Ala Leu Ser Met
            20

<210> SEQ ID NO 20
<211> LENGTH: 22
<212> TYPE: PRT
<213> ORGANISM: Artificial Sequence
<220> FEATURE:
<223> OTHER INFORMATION: Synthetic Construct

<400> SEQUENCE: 20

Met Thr Asn Lys Cys Leu Leu Gln Ile Ala Leu Leu Leu Cys Phe Ser
1               5                   10                  15

Thr Thr Ala Leu Ser Met
            20

<210> SEQ ID NO 21
<211> LENGTH: 369
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(369)

<400> SEQUENCE: 21 caa gtt cag ctt caa gaa tct ggc ggc gga agc gtt cag gct ggc gga      48
Gln Val Gln Leu Gln Glu Ser Gly Gly Gly Ser Val Gln Ala Gly Gly
1               5                   10                  15 tct ctg aga ctg agc tgt gtg gcc agc ggc tac acc gat agc aca tac      96
Ser Leu Arg Leu Ser Cys Val Ala Ser Gly Tyr Thr Asp Ser Thr Tyr
```

```
                    20                  25                  30
tgc gtc ggc tgg ttc aga cag gcc cct ggc aaa gag aga gag ggc gtc      144
Cys Val Gly Trp Phe Arg Gln Ala Pro Gly Lys Glu Arg Glu Gly Val
             35                  40                  45 gcc aga atc aac acc atc agc ggc aga cct tgg tac gcc gac tct gtg      192
Ala Arg Ile Asn Thr Ile Ser Gly Arg Pro Trp Tyr Ala Asp Ser Val
     50                  55                  60 aag ggc aga ttc aca atc agc cag gac aac agc aag aac acc gtg tac      240
Lys Gly Arg Phe Thr Ile Ser Gln Asp Asn Ser Lys Asn Thr Val Tyr
65                  70                  75                  80 ctg cag atg aac agc ctg aag cct gag gac acc gcc atc tac tac tgc      288
Leu Gln Met Asn Ser Leu Lys Pro Glu Asp Thr Ala Ile Tyr Tyr Cys
                 85                  90                  95 acc ctg acc acc gcc aac agc aga ggc ttt tgt tcc ggc ggc tac aac      336
Thr Leu Thr Thr Ala Asn Ser Arg Gly Phe Cys Ser Gly Gly Tyr Asn
            100                 105                 110 tac aaa ggc cag ggc acc caa gtg acc gtg tct                          369
Tyr Lys Gly Gln Gly Thr Gln Val Thr Val Ser
        115                 120

<210> SEQ ID NO 22
<211> LENGTH: 123
<212> TYPE: PRT
<213> ORGANISM: Artificial Sequence
<220> FEATURE:
<223> OTHER INFORMATION: Synthetic Construct

<400> SEQUENCE: 22

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Thr Asp Ser Thr Tyr
            20                  25                  30

Cys Val Gly Trp Phe Arg Gln Ala Pro Gly Lys Glu Arg Glu Gly Val
        35                  40                  45

Ala Arg Ile Asn Thr Ile Ser Gly Arg Pro Trp Tyr Ala Asp Ser Val
    50                  55                  60

Lys Gly Arg Phe Thr Ile Ser Gln Asp Asn Ser Lys Asn Thr Val Tyr
65                  70                  75                  80

Leu Gln Met Asn Ser Leu Lys Pro Glu Asp Thr Ala Ile Tyr Tyr Cys
                85                  90                  95

Thr Leu Thr Thr Ala Asn Ser Arg Gly Phe Cys Ser Gly Gly Tyr Asn
            100                 105                 110

Tyr Lys Gly Gln Gly Thr Gln Val Thr Val Ser
        115                 120

<210> SEQ ID NO 23
<211> LENGTH: 3822
<212> TYPE: DNA
<213> ORGANISM: SARS-CoV-2
<220> FEATURE:
<221> NAME/KEY: CDS
<222> LOCATION: (1)..(3822)

<400> SEQUENCE: 23 atg ttt gtt ttt ctt gtt tta ttg cca cta gtc tct agt cag tgt gtt       48
Met Phe Val Phe Leu Val Leu Leu Pro Leu Val Ser Ser Gln Cys Val
1               5                   10                  15 aat ctt aca acc aga act caa tta ccc cct gca tac act aat tct ttc       96
Asn Leu Thr Thr Arg Thr Gln Leu Pro Pro Ala Tyr Thr Asn Ser Phe
            20                  25                  30
```

| | | |
|---|---|---|
| aca cgt ggt gtt tat tac cct gac aaa gtt ttc aga tcc tca gtt tta<br>Thr Arg Gly Val Tyr Tyr Pro Asp Lys Val Phe Arg Ser Ser Val Leu<br>35 40 45 | | 144 |
| cat tca act cag gac ttg ttc tta cct ttc ttt tcc aat gtt act tgg<br>His Ser Thr Gln Asp Leu Phe Leu Pro Phe Phe Ser Asn Val Thr Trp<br>50 55 60 | | 192 |
| ttc cat gct ata cat gtc tct ggg acc aat ggt act aag agg ttt gat<br>Phe His Ala Ile His Val Ser Gly Thr Asn Gly Thr Lys Arg Phe Asp<br>65 70 75 80 | | 240 |
| aac cct gtc cta cca ttt aat gat ggt gtt tat ttt gct tcc act gag<br>Asn Pro Val Leu Pro Phe Asn Asp Gly Val Tyr Phe Ala Ser Thr Glu<br>85 90 95 | | 288 |
| aag tct aac ata ata aga ggc tgg att ttt ggt act act tta gat tcg<br>Lys Ser Asn Ile Ile Arg Gly Trp Ile Phe Gly Thr Thr Leu Asp Ser<br>100 105 110 | | 336 |
| aag acc cag tcc cta ctt att gtt aat aac gct act aat gtt gtt att<br>Lys Thr Gln Ser Leu Leu Ile Val Asn Asn Ala Thr Asn Val Val Ile<br>115 120 125 | | 384 |
| aaa gtc tgt gaa ttt caa ttt tgt aat gat cca ttt ttg ggt gtt tat<br>Lys Val Cys Glu Phe Gln Phe Cys Asn Asp Pro Phe Leu Gly Val Tyr<br>130 135 140 | | 432 |
| tac cac aaa aac aac aaa agt tgg atg gaa agt gag ttc aga gtt tat<br>Tyr His Lys Asn Asn Lys Ser Trp Met Glu Ser Glu Phe Arg Val Tyr<br>145 150 155 160 | | 480 |
| tct agt gcg aat aat tgc act ttt gaa tat gtc tct cag cct ttt ctt<br>Ser Ser Ala Asn Asn Cys Thr Phe Glu Tyr Val Ser Gln Pro Phe Leu<br>165 170 175 | | 528 |
| atg gac ctt gaa gga aaa cag ggt aat ttc aaa aat ctt agg gaa ttt<br>Met Asp Leu Glu Gly Lys Gln Gly Asn Phe Lys Asn Leu Arg Glu Phe<br>180 185 190 | | 576 |
| gtg ttt aag aat att gat ggt tat ttt aaa ata tat tct aag cac acg<br>Val Phe Lys Asn Ile Asp Gly Tyr Phe Lys Ile Tyr Ser Lys His Thr<br>195 200 205 | | 624 |
| cct att aat tta gtg cgt gat ctc cct cag ggt ttt tcg gct tta gaa<br>Pro Ile Asn Leu Val Arg Asp Leu Pro Gln Gly Phe Ser Ala Leu Glu<br>210 215 220 | | 672 |
| cca ttg gta gat ttg cca ata ggt att aac atc act agg ttt caa act<br>Pro Leu Val Asp Leu Pro Ile Gly Ile Asn Ile Thr Arg Phe Gln Thr<br>225 230 235 240 | | 720 |
| tta ctt gct tta cat aga agt tat ttg act cct ggt gat tct tct tca<br>Leu Leu Ala Leu His Arg Ser Tyr Leu Thr Pro Gly Asp Ser Ser Ser<br>245 250 255 | | 768 |
| ggt tgg aca gct ggt gct gca gct tat tat gtg ggt tat ctt caa cct<br>Gly Trp Thr Ala Gly Ala Ala Ala Tyr Tyr Val Gly Tyr Leu Gln Pro<br>260 265 270 | | 816 |
| agg act ttt cta tta aaa tat aat gaa aat gga acc att aca gat gct<br>Arg Thr Phe Leu Leu Lys Tyr Asn Glu Asn Gly Thr Ile Thr Asp Ala<br>275 280 285 | | 864 |
| gta gac tgt gca ctt gac cct ctc tca gaa aca aag tgt acg ttg aaa<br>Val Asp Cys Ala Leu Asp Pro Leu Ser Glu Thr Lys Cys Thr Leu Lys<br>290 295 300 | | 912 |
| tcc ttc act gta gaa aaa gga atc tat caa act tct aac ttt aga gtc<br>Ser Phe Thr Val Glu Lys Gly Ile Tyr Gln Thr Ser Asn Phe Arg Val<br>305 310 315 320 | | 960 |
| caa cca aca gaa tct att gtt aga ttt cct aat att aca aac ttg tgc<br>Gln Pro Thr Glu Ser Ile Val Arg Phe Pro Asn Ile Thr Asn Leu Cys<br>325 330 335 | | 1008 |
| cct ttt ggt gaa gtt ttt aac gcc acc aga ttt gca tct gtt tat gct<br>Pro Phe Gly Glu Val Phe Asn Ala Thr Arg Phe Ala Ser Val Tyr Ala<br>340 345 350 | | 1056 |

| | | | | | | | | | | | | | | | | |
|---|---|---|---|---|---|---|---|---|---|---|---|---|---|---|---|---|
| tgg | aac | agg | aag | aga | atc | agc | aac | tgt | gtt | gct | gat | tat | tct | gtc | cta | 1104 |
| Trp | Asn | Arg | Lys | Arg | Ile | Ser | Asn | Cys | Val | Ala | Asp | Tyr | Ser | Val | Leu | |
| | | | 355 | | | | 360 | | | | 365 | | | | | |
| tat | aat | tcc | gca | tca | ttt | tcc | act | ttt | aag | tgt | tat | gga | gtg | tct | cct | 1152 |
| Tyr | Asn | Ser | Ala | Ser | Phe | Ser | Thr | Phe | Lys | Cys | Tyr | Gly | Val | Ser | Pro | |
| | 370 | | | | 375 | | | | 380 | | | | | | | |
| act | aaa | tta | aat | gat | ctc | tgc | ttt | act | aat | gtc | tat | gca | gat | tca | ttt | 1200 |
| Thr | Lys | Leu | Asn | Asp | Leu | Cys | Phe | Thr | Asn | Val | Tyr | Ala | Asp | Ser | Phe | |
| 385 | | | | | 390 | | | | | 395 | | | | | 400 | |
| gta | att | aga | ggt | gat | gaa | gtc | aga | caa | atc | gct | cca | ggg | caa | act | gga | 1248 |
| Val | Ile | Arg | Gly | Asp | Glu | Val | Arg | Gln | Ile | Ala | Pro | Gly | Gln | Thr | Gly | |
| | | | | 405 | | | | | 410 | | | | | 415 | | |
| aag | att | gct | gat | tat | aat | tat | aaa | tta | cca | gat | gat | ttt | aca | ggc | tgc | 1296 |
| Lys | Ile | Ala | Asp | Tyr | Asn | Tyr | Lys | Leu | Pro | Asp | Asp | Phe | Thr | Gly | Cys | |
| | | | 420 | | | | 425 | | | | 430 | | | | | |
| gtt | ata | gct | tgg | aat | tct | aac | aat | ctt | gat | tct | aag | gtt | ggt | ggt | aat | 1344 |
| Val | Ile | Ala | Trp | Asn | Ser | Asn | Asn | Leu | Asp | Ser | Lys | Val | Gly | Gly | Asn | |
| | | | | 435 | | | | | 440 | | | | | 445 | | |
| tat | aat | tac | ctg | tat | aga | ttg | ttt | agg | aag | tct | aat | ctc | aaa | cct | ttt | 1392 |
| Tyr | Asn | Tyr | Leu | Tyr | Arg | Leu | Phe | Arg | Lys | Ser | Asn | Leu | Lys | Pro | Phe | |
| | 450 | | | | 455 | | | | 460 | | | | | | | |
| gag | aga | gat | att | tca | act | gaa | atc | tat | cag | gcc | ggt | agc | aca | cct | tgt | 1440 |
| Glu | Arg | Asp | Ile | Ser | Thr | Glu | Ile | Tyr | Gln | Ala | Gly | Ser | Thr | Pro | Cys | |
| 465 | | | | | 470 | | | | | 475 | | | | | 480 | |
| aat | ggt | gtt | gaa | ggt | ttt | aat | tgt | tac | ttt | cct | tta | caa | tca | tat | ggt | 1488 |
| Asn | Gly | Val | Glu | Gly | Phe | Asn | Cys | Tyr | Phe | Pro | Leu | Gln | Ser | Tyr | Gly | |
| | | | | 485 | | | | | 490 | | | | | 495 | | |
| ttc | caa | ccc | act | aat | ggt | gtt | ggt | tac | caa | cca | tac | aga | gta | gta | gta | 1536 |
| Phe | Gln | Pro | Thr | Asn | Gly | Val | Gly | Tyr | Gln | Pro | Tyr | Arg | Val | Val | Val | |
| | | | 500 | | | | 505 | | | | 510 | | | | | |
| ctt | tct | ttt | gaa | ctt | cta | cat | gca | cca | gca | act | gtt | tgt | gga | cct | aaa | 1584 |
| Leu | Ser | Phe | Glu | Leu | Leu | His | Ala | Pro | Ala | Thr | Val | Cys | Gly | Pro | Lys | |
| | | 515 | | | | | 520 | | | | | 525 | | | | |
| aag | tct | act | aat | ttg | gtt | aaa | aac | aaa | tgt | gtc | aat | ttc | aac | ttc | aat | 1632 |
| Lys | Ser | Thr | Asn | Leu | Val | Lys | Asn | Lys | Cys | Val | Asn | Phe | Asn | Phe | Asn | |
| | 530 | | | | 535 | | | | 540 | | | | | | | |
| ggt | tta | aca | ggc | aca | ggt | gtt | ctt | act | gag | tct | aac | aaa | aag | ttt | ctg | 1680 |
| Gly | Leu | Thr | Gly | Thr | Gly | Val | Leu | Thr | Glu | Ser | Asn | Lys | Lys | Phe | Leu | |
| 545 | | | | | 550 | | | | | 555 | | | | | 560 | |
| cct | ttc | caa | caa | ttt | ggc | aga | gac | att | gct | gac | act | act | gat | gct | gtc | 1728 |
| Pro | Phe | Gln | Gln | Phe | Gly | Arg | Asp | Ile | Ala | Asp | Thr | Thr | Asp | Ala | Val | |
| | | | | 565 | | | | | 570 | | | | | 575 | | |
| cgt | gat | cca | cag | aca | ctt | gag | att | ctt | gac | att | aca | cca | tgt | tct | ttt | 1776 |
| Arg | Asp | Pro | Gln | Thr | Leu | Glu | Ile | Leu | Asp | Ile | Thr | Pro | Cys | Ser | Phe | |
| | | | 580 | | | | | 585 | | | | | 590 | | | |
| ggt | ggt | gtc | agt | gtt | ata | aca | cca | gga | aca | aat | act | tct | aac | cag | gtt | 1824 |
| Gly | Gly | Val | Ser | Val | Ile | Thr | Pro | Gly | Thr | Asn | Thr | Ser | Asn | Gln | Val | |
| | | 595 | | | | | 600 | | | | | 605 | | | | |
| gct | gtt | ctt | tat | cag | gat | gtt | aac | tgc | aca | gaa | gtc | cct | gtt | gct | att | 1872 |
| Ala | Val | Leu | Tyr | Gln | Asp | Val | Asn | Cys | Thr | Glu | Val | Pro | Val | Ala | Ile | |
| | 610 | | | | | 615 | | | | | 620 | | | | | |
| cat | gca | gat | caa | ctt | act | cct | act | tgg | cgt | gtt | tat | tct | aca | ggt | tct | 1920 |
| His | Ala | Asp | Gln | Leu | Thr | Pro | Thr | Trp | Arg | Val | Tyr | Ser | Thr | Gly | Ser | |
| 625 | | | | | 630 | | | | | 635 | | | | | 640 | |
| aat | gtt | ttt | caa | aca | cgt | gca | ggc | tgt | tta | ata | ggg | gct | gaa | cat | gtc | 1968 |
| Asn | Val | Phe | Gln | Thr | Arg | Ala | Gly | Cys | Leu | Ile | Gly | Ala | Glu | His | Val | |
| | | | | 645 | | | | | 650 | | | | | 655 | | |
| aac | aac | tca | tat | gag | tgt | gac | ata | ccc | att | ggt | gca | ggt | ata | tgc | gct | 2016 |
| Asn | Asn | Ser | Tyr | Glu | Cys | Asp | Ile | Pro | Ile | Gly | Ala | Gly | Ile | Cys | Ala | |

|                                                              |      |
|--------------------------------------------------------------|------|
| agt tat cag act cag act aat tct cct cgg cgg gca cgt agt gta gct | 2064 |
| Ser Tyr Gln Thr Gln Thr Asn Ser Pro Arg Arg Ala Arg Ser Val Ala |      |
|         675             680             685                   |      |
| agt caa tcc atc att gcc tac act atg tca ctt ggt gca gaa aat tca | 2112 |
| Ser Gln Ser Ile Ile Ala Tyr Thr Met Ser Leu Gly Ala Glu Asn Ser |      |
|     690             695             700                       |      |
| gtt gct tac tct aat aac tct att gcc ata ccc aca aat ttt act att | 2160 |
| Val Ala Tyr Ser Asn Asn Ser Ile Ala Ile Pro Thr Asn Phe Thr Ile |      |
| 705             710             715             720           |      |
| agt gtt acc aca gaa att cta cca gtg tct atg acc aag aca tca gta | 2208 |
| Ser Val Thr Thr Glu Ile Leu Pro Val Ser Met Thr Lys Thr Ser Val |      |
|             725             730             735               |      |
| gat tgt aca atg tac att tgt ggt gat tca act gaa tgc agc aat ctt | 2256 |
| Asp Cys Thr Met Tyr Ile Cys Gly Asp Ser Thr Glu Cys Ser Asn Leu |      |
|         740             745             750                   |      |
| ttg ttg caa tat ggc agt ttt tgt aca caa tta aac cgt gct tta act | 2304 |
| Leu Leu Gln Tyr Gly Ser Phe Cys Thr Gln Leu Asn Arg Ala Leu Thr |      |
|     755             760             765                       |      |
| gga ata gct gtt gaa caa gac aaa aac acc caa gaa gtt ttt gca caa | 2352 |
| Gly Ile Ala Val Glu Gln Asp Lys Asn Thr Gln Glu Val Phe Ala Gln |      |
| 770             775             780                           |      |
| gtc aaa caa att tac aaa aca cca cca att aaa gat ttt ggt ggt ttt | 2400 |
| Val Lys Gln Ile Tyr Lys Thr Pro Pro Ile Lys Asp Phe Gly Gly Phe |      |
| 785             790             795             800           |      |
| aat ttt tca caa ata tta cca gat cca tca aaa cca agc aag agg tca | 2448 |
| Asn Phe Ser Gln Ile Leu Pro Asp Pro Ser Lys Pro Ser Lys Arg Ser |      |
|             805             810             815               |      |
| ttt att gaa gat cta ctt ttc aac aaa gtg aca ctt gca gat gct ggc | 2496 |
| Phe Ile Glu Asp Leu Leu Phe Asn Lys Val Thr Leu Ala Asp Ala Gly |      |
|         820             825             830                   |      |
| ttc atc aaa caa tat ggt gat tgc ctt ggt gat att gct gct aga gac | 2544 |
| Phe Ile Lys Gln Tyr Gly Asp Cys Leu Gly Asp Ile Ala Ala Arg Asp |      |
|     835             840             845                       |      |
| ctc att tgt gca caa aag ttt aac ggc ctt act gtt ttg cca cct ttg | 2592 |
| Leu Ile Cys Ala Gln Lys Phe Asn Gly Leu Thr Val Leu Pro Pro Leu |      |
| 850             855             860                           |      |
| ctc aca gat gaa atg att gct caa tac act tct gca ctg tta gcg ggt | 2640 |
| Leu Thr Asp Glu Met Ile Ala Gln Tyr Thr Ser Ala Leu Leu Ala Gly |      |
| 865             870             875             880           |      |
| aca atc act tct ggt tgg acc ttt ggt gca ggt gct gca tta caa ata | 2688 |
| Thr Ile Thr Ser Gly Trp Thr Phe Gly Ala Gly Ala Ala Leu Gln Ile |      |
|             885             890             895               |      |
| cca ttt gct atg caa atg gct tat agg ttt aat ggt att gga gtt aca | 2736 |
| Pro Phe Ala Met Gln Met Ala Tyr Arg Phe Asn Gly Ile Gly Val Thr |      |
|         900             905             910                   |      |
| cag aat gtt ctc tat gag aac caa aaa ttg att gcc aac caa ttt aat | 2784 |
| Gln Asn Val Leu Tyr Glu Asn Gln Lys Leu Ile Ala Asn Gln Phe Asn |      |
|     915             920             925                       |      |
| agt gct att ggc aaa att caa gac tca ctt tct tcc aca gca agt gca | 2832 |
| Ser Ala Ile Gly Lys Ile Gln Asp Ser Leu Ser Ser Thr Ala Ser Ala |      |
| 930             935             940                           |      |
| ctt gga aaa ctt caa gat gtg gtc aac caa aat gca caa gct tta aac | 2880 |
| Leu Gly Lys Leu Gln Asp Val Val Asn Gln Asn Ala Gln Ala Leu Asn |      |
| 945             950             955             960           |      |
| acg ctt gtt aaa caa ctt agc tcc aat ttt ggt gca att tca agt gtt | 2928 |
| Thr Leu Val Lys Gln Leu Ser Ser Asn Phe Gly Ala Ile Ser Ser Val |      |
|             965             970             975               |      |
| tta aat gat atc ctt tca cgt ctt gac aaa gtt gag gct gaa gtg caa | 2976 |

-continued

```
                Leu Asn Asp Ile Leu Ser Arg Leu Asp Lys Val Glu Ala Glu Val Gln
                                    980                 985                 990 att gat agg ttg atc aca ggc aga  ctt caa agt ttg cag  aca tat gtg      3024
Ile Asp Arg Leu Ile Thr Gly Arg  Leu Gln Ser Leu Gln  Thr Tyr Val
            995                 1000                 1005 act caa caa tta att aga gct gca gaa atc aga gct tct gct aat           3069
Thr Gln Gln Leu Ile Arg Ala Ala Glu Ile Arg Ala Ser Ala Asn
        1010                1015                1020 ctt gct gct act aaa atg tca gag tgt gta ctt gga caa tca aaa           3114
Leu Ala Ala Thr Lys Met Ser Glu Cys Val Leu Gly Gln Ser Lys
        1025                1030                1035 aga gtt gat ttt tgt gga aag ggc tat cat ctt atg tcc ttc cct           3159
Arg Val Asp Phe Cys Gly Lys Gly Tyr His Leu Met Ser Phe Pro
        1040                1045                1050 cag tca gca cct cat ggt gta gtc ttc ttg cat gtg act tat gtc           3204
Gln Ser Ala Pro His Gly Val Val Phe Leu His Val Thr Tyr Val
        1055                1060                1065 cct gca caa gaa aag aac ttc aca act gct cct gcc att tgt cat           3249
Pro Ala Gln Glu Lys Asn Phe Thr Thr Ala Pro Ala Ile Cys His
        1070                1075                1080 gat gga aaa gca cac ttt cct cgt gaa ggt gtc ttt gtt tca aat           3294
Asp Gly Lys Ala His Phe Pro Arg Glu Gly Val Phe Val Ser Asn
        1085                1090                1095 ggc aca cac tgg ttt gta aca caa agg aat ttt tat gaa cca caa           3339
Gly Thr His Trp Phe Val Thr Gln Arg Asn Phe Tyr Glu Pro Gln
        1100                1105                1110 atc att act aca gac aac aca ttt gtg tct ggt aac tgt gat gtt           3384
Ile Ile Thr Thr Asp Asn Thr Phe Val Ser Gly Asn Cys Asp Val
        1115                1120                1125 gta ata gga att gtc aac aac aca gtt tat gat cct ttg caa cct           3429
Val Ile Gly Ile Val Asn Asn Thr Val Tyr Asp Pro Leu Gln Pro
        1130                1135                1140 gaa tta gac tca ttc aag gag gag tta gat aaa tat ttt aag aat           3474
Glu Leu Asp Ser Phe Lys Glu Glu Leu Asp Lys Tyr Phe Lys Asn
        1145                1150                1155 cat aca tca cca gat gtt gat tta ggt gac atc tct ggc att aat           3519
His Thr Ser Pro Asp Val Asp Leu Gly Asp Ile Ser Gly Ile Asn
        1160                1165                1170 gct tca gtt gta aac att caa aaa gaa att gac cgc ctc aat gag           3564
Ala Ser Val Val Asn Ile Gln Lys Glu Ile Asp Arg Leu Asn Glu
        1175                1180                1185 gtt gcc aag aat tta aat gaa tct ctc atc gat ctc caa gaa ctt           3609
Val Ala Lys Asn Leu Asn Glu Ser Leu Ile Asp Leu Gln Glu Leu
        1190                1195                1200 gga aag tat gag cag tat ata aaa tgg cca tgg tac att tgg cta           3654
Gly Lys Tyr Glu Gln Tyr Ile Lys Trp Pro Trp Tyr Ile Trp Leu
        1205                1210                1215 ggt ttt ata gct ggc ttg att gcc ata gta atg gtg aca att atg           3699
Gly Phe Ile Ala Gly Leu Ile Ala Ile Val Met Val Thr Ile Met
        1220                1225                1230 ctt tgc tgt atg acc agt tgc tgt agt tgt ctc aag ggc tgt tgt           3744
Leu Cys Cys Met Thr Ser Cys Cys Ser Cys Leu Lys Gly Cys Cys
        1235                1240                1245 tct tgt gga tcc tgc tgc aaa ttt gat gaa gac gac tct gag cca           3789
Ser Cys Gly Ser Cys Cys Lys Phe Asp Glu Asp Asp Ser Glu Pro
        1250                1255                1260 gtg ctc aaa gga gtc aaa tta cat tac aca taa                           3822
Val Leu Lys Gly Val Lys Leu His Tyr Thr
        1265                1270
```

```
<210> SEQ ID NO 24
<211> LENGTH: 1273
<212> TYPE: PRT
<213> ORGANISM: SARS-CoV-2

<400> SEQUENCE: 24

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380
```

```
Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
    515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
        610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
    675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
    755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800
```

```
Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
        820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
        900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
        930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn
        1010                1015                1020

Leu Ala Ala Thr Lys Met Ser Glu Cys Val Leu Gly Gln Ser Lys
        1025                1030                1035

Arg Val Asp Phe Cys Gly Lys Gly Tyr His Leu Met Ser Phe Pro
        1040                1045                1050

Gln Ser Ala Pro His Gly Val Val Phe Leu His Val Thr Tyr Val
        1055                1060                1065

Pro Ala Gln Glu Lys Asn Phe Thr Thr Ala Pro Ala Ile Cys His
        1070                1075                1080

Asp Gly Lys Ala His Phe Pro Arg Glu Gly Val Phe Val Ser Asn
        1085                1090                1095

Gly Thr His Trp Phe Val Thr Gln Arg Asn Phe Tyr Glu Pro Gln
        1100                1105                1110

Ile Ile Thr Thr Asp Asn Thr Phe Val Ser Gly Asn Cys Asp Val
        1115                1120                1125

Val Ile Gly Ile Val Asn Asn Thr Val Tyr Asp Pro Leu Gln Pro
        1130                1135                1140

Glu Leu Asp Ser Phe Lys Glu Glu Leu Asp Lys Tyr Phe Lys Asn
        1145                1150                1155

His Thr Ser Pro Asp Val Asp Leu Gly Asp Ile Ser Gly Ile Asn
        1160                1165                1170

Ala Ser Val Val Asn Ile Gln Lys Glu Ile Asp Arg Leu Asn Glu
        1175                1180                1185

Val Ala Lys Asn Leu Asn Glu Ser Leu Ile Asp Leu Gln Glu Leu
        1190                1195                1200

Gly Lys Tyr Glu Gln Tyr Ile Lys Trp Pro Trp Tyr Ile Trp Leu
```

```
                 1205               1210                1215
Gly Phe Ile Ala Gly Leu Ile Ala Ile Val Met Val Thr Ile Met
         1220                1225                1230

Leu Cys Cys Met Thr Ser Cys Cys Ser Cys Leu Lys Gly Cys Cys
         1235                1240                1245

Ser Cys Gly Ser Cys Cys Lys Phe Asp Glu Asp Asp Ser Glu Pro
         1250                1255                1260

Val Leu Lys Gly Val Lys Leu His Tyr Thr
         1265                1270

<210> SEQ ID NO 25
<211> LENGTH: 1260
<212> TYPE: DNA
<213> ORGANISM: SARS-CoV-2
<220> FEATURE:
<221> NAME/KEY: CDS
<222> LOCATION: (1)..(1260)

<400> SEQUENCE: 25 atg tct gat aat gga ccc caa aat cag cga aat gca ccc cgc att acg      48
Met Ser Asp Asn Gly Pro Gln Asn Gln Arg Asn Ala Pro Arg Ile Thr
1               5                   10                  15 ttt ggt gga ccc tca gat tca act ggc agt aac cag aat gga gaa cgc      96
Phe Gly Gly Pro Ser Asp Ser Thr Gly Ser Asn Gln Asn Gly Glu Arg
                20                  25                  30 agt ggg gcg cga tca aaa caa cgt cgg ccc caa ggt tta ccc aat aat     144
Ser Gly Ala Arg Ser Lys Gln Arg Arg Pro Gln Gly Leu Pro Asn Asn
            35                  40                  45 act gcg tct tgg ttc acc gct ctc act caa cat ggc aag gaa gac ctt     192
Thr Ala Ser Trp Phe Thr Ala Leu Thr Gln His Gly Lys Glu Asp Leu
        50                  55                  60 aaa ttc cct cga gga caa ggc gtt cca att aac acc aat agc agt cca     240
Lys Phe Pro Arg Gly Gln Gly Val Pro Ile Asn Thr Asn Ser Ser Pro
65                  70                  75                  80 gat gac caa att ggc tac tac cga aga gct acc aga cga att cgt ggt     288
Asp Asp Gln Ile Gly Tyr Tyr Arg Arg Ala Thr Arg Arg Ile Arg Gly
                85                  90                  95 ggt gac ggt aaa atg aaa gat ctc agt cca aga tgg tat ttc tac tac     336
Gly Asp Gly Lys Met Lys Asp Leu Ser Pro Arg Trp Tyr Phe Tyr Tyr
            100                 105                 110 cta gga act ggg cca gaa gct gga ctt ccc tat ggt gct aac aaa gac     384
Leu Gly Thr Gly Pro Glu Ala Gly Leu Pro Tyr Gly Ala Asn Lys Asp
        115                 120                 125 ggc atc ata tgg gtt gca act gag gga gcc ttg aat aca cca aaa gat     432
Gly Ile Ile Trp Val Ala Thr Glu Gly Ala Leu Asn Thr Pro Lys Asp
    130                 135                 140 cac att ggc acc cgc aat cct gct aac aat gct gca atc gtg cta caa     480
His Ile Gly Thr Arg Asn Pro Ala Asn Asn Ala Ala Ile Val Leu Gln
145                 150                 155                 160 ctt cct caa gga aca aca ttg cca aaa ggc ttc tac gca gaa ggg agc     528
Leu Pro Gln Gly Thr Thr Leu Pro Lys Gly Phe Tyr Ala Glu Gly Ser
                165                 170                 175 aga ggc ggc agt caa gcc tct tct cgt tcc tca tca cgt agt cgc aac     576
Arg Gly Gly Ser Gln Ala Ser Ser Arg Ser Ser Ser Arg Ser Arg Asn
            180                 185                 190 agt tca aga aat tca act cca ggc agc agt agg gga act tct cct gct     624
Ser Ser Arg Asn Ser Thr Pro Gly Ser Ser Arg Gly Thr Ser Pro Ala
        195                 200                 205 aga atg gct ggc aat ggc ggt gat gct gct ctt gct ttg ctg ctg ctt     672
Arg Met Ala Gly Asn Gly Gly Asp Ala Ala Leu Ala Leu Leu Leu Leu
```

-continued

```
                  210                 215                  220
gac aga ttg aac cag ctt gag agc aaa atg tct ggt aaa ggc caa caa            720
Asp Arg Leu Asn Gln Leu Glu Ser Lys Met Ser Gly Lys Gly Gln Gln
225                 230                 235                 240 caa caa ggc caa act gtc act aag aaa tct gct gct gag gct tct aag            768
Gln Gln Gly Gln Thr Val Thr Lys Lys Ser Ala Ala Glu Ala Ser Lys
                245                 250                 255 aag cct cgg caa aaa cgt act gcc act aaa gca tac aat gta aca caa            816
Lys Pro Arg Gln Lys Arg Thr Ala Thr Lys Ala Tyr Asn Val Thr Gln
            260                 265                 270 gct ttc ggc aga cgt ggt cca gaa caa acc caa gga aat ttt ggg gac            864
Ala Phe Gly Arg Arg Gly Pro Glu Gln Thr Gln Gly Asn Phe Gly Asp
        275                 280                 285 cag gaa cta atc aga caa gga act gat tac aaa cat tgg ccg caa att            912
Gln Glu Leu Ile Arg Gln Gly Thr Asp Tyr Lys His Trp Pro Gln Ile
    290                 295                 300 gca caa ttt gcc ccc agc gct tca gcg ttc ttc gga atg tcg cgc att            960
Ala Gln Phe Ala Pro Ser Ala Ser Ala Phe Phe Gly Met Ser Arg Ile
305                 310                 315                 320 ggc atg gaa gtc aca cct tcg gga acg tgg ttg acc tac aca ggt gcc           1008
Gly Met Glu Val Thr Pro Ser Gly Thr Trp Leu Thr Tyr Thr Gly Ala
                325                 330                 335 atc aaa ttg gat gac aaa gat cca aat ttc aaa gat caa gtc att ttg           1056
Ile Lys Leu Asp Asp Lys Asp Pro Asn Phe Lys Asp Gln Val Ile Leu
            340                 345                 350 ctg aat aag cat att gac gca tac aaa aca ttc cca cca aca gag cct           1104
Leu Asn Lys His Ile Asp Ala Tyr Lys Thr Phe Pro Pro Thr Glu Pro
        355                 360                 365 aaa aag gac aaa aag aag aag gct gat gaa act caa gcc tta ccg cag           1152
Lys Lys Asp Lys Lys Lys Lys Ala Asp Glu Thr Gln Ala Leu Pro Gln
370                 375                 380 aga cag aag aaa cag caa act gtg act ctt ctt cct gct gca gat ttg           1200
Arg Gln Lys Lys Gln Gln Thr Val Thr Leu Leu Pro Ala Ala Asp Leu
385                 390                 395                 400 gat gat ttc tcc aaa caa ttg caa caa tcc atg agc agt gct gac tca           1248
Asp Asp Phe Ser Lys Gln Leu Gln Gln Ser Met Ser Ser Ala Asp Ser
                405                 410                 415 act cag gcc taa                                                           1260
Thr Gln Ala <210> SEQ ID NO 26
<211> LENGTH: 419
<212> TYPE: PRT
<213> ORGANISM: SARS-CoV-2

<400> SEQUENCE: 26

Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
        35                  40                  45

Thr Ala Ser Trp Phe Thr Ala Leu Thr Gln His Gly Lys Glu Asp Leu
    50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95
```

Gly Asp Gly Lys Met Lys Asp Leu Ser Pro Arg Trp Tyr Phe Tyr Tyr
            100                 105                 110

Leu Gly Thr Gly Pro Glu Ala Gly Leu Pro Tyr Gly Ala Asn Lys Asp
        115                 120                 125

Gly Ile Ile Trp Val Ala Thr Glu Gly Ala Leu Asn Thr Pro Lys Asp
    130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
            180                 185                 190

Ser Ser Arg Asn Ser Thr Pro Gly Ser Ser Arg Gly Thr Ser Pro Ala
        195                 200                 205

Arg Met Ala Gly Asn Gly Gly Asp Ala Ala Leu Ala Leu Leu Leu Leu
    210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Ala Tyr Asn Val Thr Gln
            260                 265                 270

Ala Phe Gly Arg Arg Gly Pro Glu Gln Thr Gln Gly Asn Phe Gly Asp
        275                 280                 285

Gln Glu Leu Ile Arg Gln Gly Thr Asp Tyr Lys His Trp Pro Gln Ile
    290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
            340                 345                 350

Leu Asn Lys His Ile Asp Ala Tyr Lys Thr Phe Pro Pro Thr Glu Pro
        355                 360                 365

Lys Lys Asp Lys Lys Lys Ala Asp Glu Thr Gln Ala Leu Pro Gln
    370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
                405                 410                 415

Thr Gln Ala

<210> SEQ ID NO 27
<211> LENGTH: 366
<212> TYPE: DNA
<213> ORGANISM: SARS-CoV-2
<220> FEATURE:
<221> NAME/KEY: CDS
<222> LOCATION: (1)..(366)

<400> SEQUENCE: 27 atg aaa ttt ctt gtt ttc tta gga atc atc aca act gta gct gca ttt    48
Met Lys Phe Leu Val Phe Leu Gly Ile Ile Thr Thr Val Ala Ala Phe
1               5                   10                  15 cac caa gaa tgt agt tta cag tca tgt act caa cat caa cca tat gta    96
His Gln Glu Cys Ser Leu Gln Ser Cys Thr Gln His Gln Pro Tyr Val

```
                    20                  25                  30
gtt gat gac ccg tgt cct att cac ttc tat tct aaa tgg tat att aga      144
Val Asp Asp Pro Cys Pro Ile His Phe Tyr Ser Lys Trp Tyr Ile Arg
        35                  40                  45 gta gga gct aga aaa tca gca cct tta att gaa ttg tgc gtg gat gag      192
Val Gly Ala Arg Lys Ser Ala Pro Leu Ile Glu Leu Cys Val Asp Glu
    50                  55                  60 gct ggt tct aaa tca ccc att cag tac atc gat atc ggt aat tat aca      240
Ala Gly Ser Lys Ser Pro Ile Gln Tyr Ile Asp Ile Gly Asn Tyr Thr
65                  70                  75                  80 gtt tcc tgt tta cct ttt aca att aat tgc cag gaa cct aaa ttg ggt      288
Val Ser Cys Leu Pro Phe Thr Ile Asn Cys Gln Glu Pro Lys Leu Gly
                85                  90                  95 agt ctt gta gtg cgt tgt tcg ttc tat gaa gac ttt tta gag tat cat      336
Ser Leu Val Val Arg Cys Ser Phe Tyr Glu Asp Phe Leu Glu Tyr His
            100                 105                 110 gac gtt cgt gtt gtt tta gat ttc atc taa                              366
Asp Val Arg Val Val Leu Asp Phe Ile
        115                 120
```

<210> SEQ ID NO 28
<211> LENGTH: 121
<212> TYPE: PRT
<213> ORGANISM: SARS-CoV-2

<400> SEQUENCE: 28

```
Met Lys Phe Leu Val Phe Leu Gly Ile Ile Thr Thr Val Ala Ala Phe
1               5                   10                  15

His Gln Glu Cys Ser Leu Gln Ser Cys Thr Gln His Gln Pro Tyr Val
            20                  25                  30

Val Asp Asp Pro Cys Pro Ile His Phe Tyr Ser Lys Trp Tyr Ile Arg
        35                  40                  45

Val Gly Ala Arg Lys Ser Ala Pro Leu Ile Glu Leu Cys Val Asp Glu
    50                  55                  60

Ala Gly Ser Lys Ser Pro Ile Gln Tyr Ile Asp Ile Gly Asn Tyr Thr
65                  70                  75                  80

Val Ser Cys Leu Pro Phe Thr Ile Asn Cys Gln Glu Pro Lys Leu Gly
                85                  90                  95

Ser Leu Val Val Arg Cys Ser Phe Tyr Glu Asp Phe Leu Glu Tyr His
            100                 105                 110

Asp Val Arg Val Val Leu Asp Phe Ile
        115                 120
```

<210> SEQ ID NO 29
<211> LENGTH: 300
<212> TYPE: DNA
<213> ORGANISM: SARS-CoV-2
<220> FEATURE:
<221> NAME/KEY: CDS
<222> LOCATION: (1)..(300)

<400> SEQUENCE: 29

```
atg gcc tac tgt tgg aga tgc acc agc tgc tgc ttc agc gag cgg ttc      48
Met Ala Tyr Cys Trp Arg Cys Thr Ser Cys Cys Phe Ser Glu Arg Phe
1               5                   10                  15 cag aac cac aat cct cag aaa gag atg gcc acc agc aca ctg cag ggc      96
Gln Asn His Asn Pro Gln Lys Glu Met Ala Thr Ser Thr Leu Gln Gly
            20                  25                  30 tgt tct ctg tgt ctg cag ctg gcc gtg gtg gtc aac tct ctg ctg acc      144
Cys Ser Leu Cys Leu Gln Leu Ala Val Val Val Asn Ser Leu Leu Thr
```

```
        35                  40                  45
cct ttc gcc aga tgc tgc tgg cct gaa ttc ggc gga ggc agc ggc ggt        192
Pro Phe Ala Arg Cys Cys Trp Pro Glu Phe Gly Gly Gly Ser Gly Gly
         50                  55                  60 gga agc ggc gga ggc tct gct tgg agc cac ccg cag ttc gaa aaa ggt        240
Gly Ser Gly Gly Gly Ser Ala Trp Ser His Pro Gln Phe Glu Lys Gly
 65                  70                  75                  80 gga ggt tct ggc ggt gga tcg gga ggt tca gcg tgg agc cac ccg cag        288
Gly Gly Ser Gly Gly Gly Ser Gly Gly Ser Ala Trp Ser His Pro Gln
                 85                  90                  95 ttc gag aaa tga                                                        300
Phe Glu Lys <210> SEQ ID NO 30
<211> LENGTH: 99
<212> TYPE: PRT
<213> ORGANISM: SARS-CoV-2

<400> SEQUENCE: 30

Met Ala Tyr Cys Trp Arg Cys Thr Ser Cys Cys Phe Ser Glu Arg Phe
 1               5                  10                  15

Gln Asn His Asn Pro Gln Lys Glu Met Ala Thr Ser Thr Leu Gln Gly
             20                  25                  30

Cys Ser Leu Cys Leu Gln Leu Ala Val Val Val Asn Ser Leu Leu Thr
         35                  40                  45

Pro Phe Ala Arg Cys Cys Trp Pro Glu Phe Gly Gly Gly Ser Gly Gly
     50                  55                  60

Gly Ser Gly Gly Gly Ser Ala Trp Ser His Pro Gln Phe Glu Lys Gly
 65                  70                  75                  80

Gly Gly Ser Gly Gly Gly Ser Gly Gly Ser Ala Trp Ser His Pro Gln
                 85                  90                  95

Phe Glu Lys

<210> SEQ ID NO 31
<211> LENGTH: 378
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(378)

<400> SEQUENCE: 31 cag gtt cag ctg gtt gaa tct ggc gga ggc ctg atg caa gct ggc gga         48
Gln Val Gln Leu Val Glu Ser Gly Gly Gly Leu Met Gln Ala Gly Gly
 1               5                  10                  15 tct ctg aga ctg agc tgt gcc gtg tcc ggc aga acc ttt tct aca gcc         96
Ser Leu Arg Leu Ser Cys Ala Val Ser Gly Arg Thr Phe Ser Thr Ala
             20                  25                  30 gcc atg ggc tgg ttc aga cag gcc cct gga aaa gaa cgc gag ttc gtg        144
Ala Met Gly Trp Phe Arg Gln Ala Pro Gly Lys Glu Arg Glu Phe Val
         35                  40                  45 gcc gct atc cgt tgg agc gga ggc tct gcc tac tac gcc gat tct gtg        192
Ala Ala Ile Arg Trp Ser Gly Gly Ser Ala Tyr Tyr Ala Asp Ser Val
     50                  55                  60 aag ggc aga ttc acc atc agc aga gac aag gcc aag aac acc gtg tac        240
Lys Gly Arg Phe Thr Ile Ser Arg Asp Lys Ala Lys Asn Thr Val Tyr
 65                  70                  75                  80 ctg cag atg aac agc ctg aag tac gag gac acc gcc gtg tac tac tgc        288
```

```
Leu Gln Met Asn Ser Leu Lys Tyr Glu Asp Thr Ala Val Tyr Tyr Cys
                 85                  90                  95 gcc aga aca gag aat gtg cgg agc ctg ctg agc gac tac gcc acc tgg       336
Ala Arg Thr Glu Asn Val Arg Ser Leu Leu Ser Asp Tyr Ala Thr Trp
            100                 105                 110 cct tac gat tat tgg ggc cag ggc acc caa gtg acc gtt tct               378
Pro Tyr Asp Tyr Trp Gly Gln Gly Thr Gln Val Thr Val Ser
        115                 120                 125

<210> SEQ ID NO 32
<211> LENGTH: 126
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Val Glu Ser Gly Gly Gly Leu Met Gln Ala Gly Gly
1               5                   10                  15

Ser Leu Arg Leu Ser Cys Ala Val Ser Gly Arg Thr Phe Ser Thr Ala
            20                  25                  30

Ala Met Gly Trp Phe Arg Gln Ala Pro Gly Lys Glu Arg Glu Phe Val
        35                  40                  45

Ala Ala Ile Arg Trp Ser Gly Gly Ser Ala Tyr Tyr Ala Asp Ser Val
    50                  55                  60

Lys Gly Arg Phe Thr Ile Ser Arg Asp Lys Ala Lys Asn Thr Val Tyr
65                  70                  75                  80

Leu Gln Met Asn Ser Leu Lys Tyr Glu Asp Thr Ala Val Tyr Tyr Cys
                85                  90                  95

Ala Arg Thr Glu Asn Val Arg Ser Leu Leu Ser Asp Tyr Ala Thr Trp
            100                 105                 110

Pro Tyr Asp Tyr Trp Gly Gln Gly Thr Gln Val Thr Val Ser
        115                 120                 125

<210> SEQ ID NO 33
<211> LENGTH: 696
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(696)

<400> SEQUENCE: 33 gag cct aag agc tgc gac aag acc cac acc tgt cct cca tgt cct gct       48
Glu Pro Lys Ser Cys Asp Lys Thr His Thr Cys Pro Pro Cys Pro Ala
1               5                   10                  15 cca gaa ctg ctc ggc gga cct tcc gtg ttc ctg ttt cct cca aag cct       96
Pro Glu Leu Leu Gly Gly Pro Ser Val Phe Leu Phe Pro Pro Lys Pro
            20                  25                  30 aag gac acc ctg atg atc agc aga acc cct gaa gtg acc tgc gtg gtg       144
Lys Asp Thr Leu Met Ile Ser Arg Thr Pro Glu Val Thr Cys Val Val
        35                  40                  45 gtg gat gtg tcc cac gaa gat ccc gaa gtg aag ttc aat tgg tac gtg       192
Val Asp Val Ser His Glu Asp Pro Glu Val Lys Phe Asn Trp Tyr Val
    50                  55                  60 gac ggc gtg gaa gtg cac aac gcc aag acc aag cct aga gag gaa cag       240
Asp Gly Val Glu Val His Asn Ala Lys Thr Lys Pro Arg Glu Glu Gln
65                  70                  75                  80 tac aac agc acc tac aga gtg gtg tcc gtg ctg acc gtg ctg cac cag       288
```

```
                Tyr Asn Ser Thr Tyr Arg Val Val Ser Val Leu Thr Val Leu His Gln
                                 85                  90                  95 gat tgg ctg aac ggc aaa gag tac aag tgc aag gtg tcc aac aag gcc         336
Asp Trp Leu Asn Gly Lys Glu Tyr Lys Cys Lys Val Ser Asn Lys Ala
            100                 105                 110 ctg cct gct cct atc gag aaa acc atc agc aag gcc aag ggc cag cct         384
Leu Pro Ala Pro Ile Glu Lys Thr Ile Ser Lys Ala Lys Gly Gln Pro
        115                 120                 125 agg gaa ccc cag gtt tac aca ctg cct cca agc cgg gaa gag atg acc         432
Arg Glu Pro Gln Val Tyr Thr Leu Pro Pro Ser Arg Glu Glu Met Thr
    130                 135                 140 aag aac cag gtg tcc ctg acc tgc ctg gtc aag ggc ttc tac cct tcc         480
Lys Asn Gln Val Ser Leu Thr Cys Leu Val Lys Gly Phe Tyr Pro Ser
145                 150                 155                 160 gat atc gcc gtg gaa tgg gag agc aat ggc cag cct gag aac aac tac         528
Asp Ile Ala Val Glu Trp Glu Ser Asn Gly Gln Pro Glu Asn Asn Tyr
                165                 170                 175 aag aca acc cct cct gtg ctg gac agc gac ggc tca ttc ttc ctg tat         576
Lys Thr Thr Pro Pro Val Leu Asp Ser Asp Gly Ser Phe Phe Leu Tyr
            180                 185                 190 agc aag ctg aca gtg gac aag agc aga tgg cag cag ggc aac gtg ttc         624
Ser Lys Leu Thr Val Asp Lys Ser Arg Trp Gln Gln Gly Asn Val Phe
        195                 200                 205 agc tgc agc gtg atg cac gag gcc ctg cac aac cac tac acc cag aag         672
Ser Cys Ser Val Met His Glu Ala Leu His Asn His Tyr Thr Gln Lys
    210                 215                 220 tcc ctg agc ctg tct cct ggc aag                                         696
Ser Leu Ser Leu Ser Pro Gly Lys
225                 230

<210> SEQ ID NO 34
<211> LENGTH: 232
<212> TYPE: PRT
<213> ORGANISM: Artificial Sequence
<220> FEATURE:
<223> OTHER INFORMATION: Synthetic Construct

<400> SEQUENCE: 34

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160
```

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 35
<211> LENGTH: 186
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(186)

<400> SEQUENCE: 35 gag cct aag atc cct cag cct cag cca aag cct caa cca caa ccg cag       48
Glu Pro Lys Ile Pro Gln Pro Gln Pro Lys Pro Gln Pro Gln Pro Gln
1               5                   10                  15 cca cag cct aaa ccg cag cct aag cca gag cct gag cag cgg atg aag       96
Pro Gln Pro Lys Pro Gln Pro Lys Pro Glu Pro Glu Gln Arg Met Lys
            20                  25                  30 cag atc gag gac aag atc gaa gag atc ctg agc aaa atc tac cac atc      144
Gln Ile Glu Asp Lys Ile Glu Glu Ile Leu Ser Lys Ile Tyr His Ile
        35                  40                  45 gag aac gag atc gcc cgg atc aag aag ctc gtc ggc gaa aga              186
Glu Asn Glu Ile Ala Arg Ile Lys Lys Leu Val Gly Glu Arg
    50                  55                  60

<210> SEQ ID NO 36
<211> LENGTH: 62
<212> TYPE: PRT
<213> ORGANISM: Artificial Sequence
<220> FEATURE:
<223> OTHER INFORMATION: Synthetic Construct

<400> SEQUENCE: 36

Glu Pro Lys Ile Pro Gln Pro Gln Pro Lys Pro Gln Pro Gln Pro Gln
1               5                   10                  15

Pro Gln Pro Lys Pro Gln Pro Lys Pro Glu Pro Glu Gln Arg Met Lys
            20                  25                  30

Gln Ile Glu Asp Lys Ile Glu Glu Ile Leu Ser Lys Ile Tyr His Ile
        35                  40                  45

Glu Asn Glu Ile Ala Arg Ile Lys Lys Leu Val Gly Glu Arg
    50                  55                  60

<210> SEQ ID NO 37
<211> LENGTH: 9
<212> TYPE: DNA
<213> ORGANISM: Artificial Sequence
<220> FEATURE:
<223> OTHER INFORMATION: Sythetic
<220> FEATURE:
<221> NAME/KEY: CDS
<222> LOCATION: (1)..(9)

<400> SEQUENCE: 37
```

```
ggc gcg cct                                                     9
Gly Ala Pro
 1

<210> SEQ ID NO 38
<211> LENGTH: 3
<212> TYPE: PRT
<213> ORGANISM: Artificial Sequence
<220> FEATURE:
<223> OTHER INFORMATION: Synthetic

<400> SEQUENCE: 38

Gly Ala Pro
 1

<210> SEQ ID NO 39
<211> LENGTH: 66
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(66)

<400> SEQUENCE: 39 ggt ggt acc agc gga ggc gga gga tca ggt ggc gga ggt agt ggt ggt     48
Gly Gly Thr Ser Gly Gly Gly Gly Ser Gly Gly Gly Gly Ser Gly Gly
 1               5                   10                  15 ggc ggt agc gcg gcc gcc                                         66
Gly Gly Ser Ala Ala Ala
            20

<210> SEQ ID NO 40
<211> LENGTH: 22
<212> TYPE: PRT
<213> ORGANISM: Artificial Sequence
<220> FEATURE:
<223> OTHER INFORMATION: Synthetic Construct

<400> SEQUENCE: 40

Gly Gly Thr Ser Gly Gly Gly Gly Ser Gly Gly Gly Gly Ser Gly Gly
 1               5                   10                  15

Gly Gly Ser Ala Ala Ala
            20

<210> SEQ ID NO 41
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(42)

<400> SEQUENCE: 41 gaa ttc ggc gga ggc agc ggc ggt gga agc ggc gga ggc tct         42
Glu Phe Gly Gly Gly Ser Gly Gly Gly Ser Gly Gly Gly Ser
 1               5                   10

<210> SEQ ID NO 42
<211> LENGTH: 14
<212> TYPE: PRT
<213> ORGANISM: Artificial Sequence
<220> FEATURE:
<223> OTHER INFORMATION: Synthetic Construct
```

```
<400> SEQUENCE: 42

Glu Phe Gly Gly Gly Ser Gly Gly Gly Ser Gly Gly Gly Ser
1               5                   10

<210> SEQ ID NO 43
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(45)

<400> SEQUENCE: 43 atc ccg cgg ggt ggt ggt agt ggc gga gga agt ggt ggc gga tct      45
Ile Pro Arg Gly Gly Gly Ser Gly Gly Gly Ser Gly Gly Gly Ser
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetic Construct

<400> SEQUENCE: 44

Ile Pro Arg Gly Gly Gly Ser Gly Gly Gly Ser Gly Gly Gly Ser
1               5                   10                  15

<210> SEQ ID NO 45
<211> LENGTH: 63
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(63)

<400> SEQUENCE: 45 gaa ttc tct ggc ggc gga gga tct ggc gga ggt gga agc gga ggc ggt      48
Glu Phe Ser Gly Gly Gly Gly Ser Gly Gly Gly Gly Ser Gly Gly Gly
1               5                   10                  15 gga tct gcg gcc gcc                                                 63
Gly Ser Ala Ala Ala
            20

<210> SEQ ID NO 46
<211> LENGTH: 21
<212> TYPE: PRT
<213> ORGANISM: Artificial Sequence
<220> FEATURE:
<223> OTHER INFORMATION: Synthetic Construct

<400> SEQUENCE: 46

Glu Phe Ser Gly Gly Gly Gly Ser Gly Gly Gly Gly Ser Gly Gly Gly
1               5                   10                  15

Gly Ser Ala Ala Ala
            20

<210> SEQ ID NO 47
<211> LENGTH: 9
<212> TYPE: DNA
<213> ORGANISM: Artificial Sequence
<220> FEATURE:
<223> OTHER INFORMATION: Synthetic
```

```
<220> FEATURE:
<221> NAME/KEY: CDS
<222> LOCATION: (1)..(9)

<400> SEQUENCE: 47 agc ggt acc                                                              9
Ser Gly Thr
1

<210> SEQ ID NO 48
<211> LENGTH: 3
<212> TYPE: PRT
<213> ORGANISM: Artificial Sequence
<220> FEATURE:
<223> OTHER INFORMATION: Synthetic

<400> SEQUENCE: 48

Ser Gly Thr
1

<210> SEQ ID NO 49
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(45)

<400> SEQUENCE: 49 ggt gaa ttc ggc gga ggc agc ggc ggt gga agc ggc gga ggc tct             45
Gly Glu Phe Gly Gly Gly Ser Gly Gly Gly Ser Gly Gly Gly Ser
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic Construct

<400> SEQUENCE: 50

Gly Glu Phe Gly Gly Gly Ser Gly Gly Gly Ser Gly Gly Gly Ser
1               5                   10                  15

<210> SEQ ID NO 51
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(51)

<400> SEQUENCE: 51 ggt ggc gga gga agc gga ggc gga gga tca ggt ggc ggt gga tct atc         48
Gly Gly Gly Gly Ser Gly Gly Gly Gly Ser Gly Gly Gly Gly Ser Ile
1               5                   10                  15 gat                                                                     51
Asp

<210> SEQ ID NO 52
<211> LENGTH: 17
<212> TYPE: PRT
<213> ORGANISM: Artificial Sequence
<220> FEATURE:
```

<223> OTHER INFORMATION: Synthetic Construct

<400> SEQUENCE: 52

Gly Gly Gly Gly Ser Gly Gly Gly Ser Gly Gly Gly Ser Ile
1               5                   10                  15

Asp

<210> SEQ ID NO 53
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(60)

<400> SEQUENCE: 53 agc ggt acc ggc gga ggt gga agc gga ggc gga ggc tct ggc ggc ggt     48
Ser Gly Thr Gly Gly Gly Gly Ser Gly Gly Gly Gly Ser Gly Gly Gly
1               5                   10                  15 gga tct gga tcc                                                     60
Gly Ser Gly Ser
            20

<210> SEQ ID NO 54
<211> LENGTH: 20
<212> TYPE: PRT
<213> ORGANISM: Artificial Sequence
<220> FEATURE:
<223> OTHER INFORMATION: Synthetic Construct

<400> SEQUENCE: 54

Ser Gly Thr Gly Gly Gly Gly Ser Gly Gly Gly Gly Ser Gly Gly Gly
1               5                   10                  15

Gly Ser Gly Ser
            20

<210> SEQ ID NO 55
<211> LENGTH: 48
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(48)

<400> SEQUENCE: 55 ccg cgg ggt ggt ggt tcc ggc gga ggt agt ggc ggc gga tct gcg gcc     48
Pro Arg Gly Gly Gly Ser Gly Gly Gly Ser Gly Gly Gly Ser Ala Ala
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Synthetic Construct

<400> SEQUENCE: 56

Pro Arg Gly Gly Gly Ser Gly Gly Gly Ser Gly Gly Gly Ser Ala Ala
1               5                   10                  15

<210> SEQ ID NO 57
<211> LENGTH: 30

<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(30)

<400> SEQUENCE: 57

```
gcg tgg agc cac ccg cag ttc gag aaa tga                          30
Ala Trp Ser His Pro Gln Phe Glu Lys
1               5
```

<210> SEQ ID NO 58
<211> LENGTH: 9
<212> TYPE: PRT
<213> ORGANISM: Artificial Sequence
<220> FEATURE:
<223> OTHER INFORMATION: Synthetic Construct

<400> SEQUENCE: 58

```
Ala Trp Ser His Pro Gln Phe Glu Lys
1               5
```

<210> SEQ ID NO 59
<211> LENGTH: 90
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(90)

<400> SEQUENCE: 59

```
gct tgg agc cac ccg cag ttc gaa aaa ggt gga ggt tct ggc ggt gga   48
Ala Trp Ser His Pro Gln Phe Glu Lys Gly Gly Gly Ser Gly Gly Gly
1               5                   10                  15 tcg gga ggt tca gcg tgg agc cac ccg cag ttc gag aaa tga           90
Ser Gly Gly Ser Ala Trp Ser His Pro Gln Phe Glu Lys
            20                  25
```

<210> SEQ ID NO 60
<211> LENGTH: 29
<212> TYPE: PRT
<213> ORGANISM: Artificial Sequence
<220> FEATURE:
<223> OTHER INFORMATION: Synthetic Construct

<400> SEQUENCE: 60

```
Ala Trp Ser His Pro Gln Phe Glu Lys Gly Gly Gly Ser Gly Gly Gly
1               5                   10                  15

Ser Gly Gly Ser Ala Trp Ser His Pro Gln Phe Glu Lys
            20                  25
```

<210> SEQ ID NO 61
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(21)

<400> SEQUENCE: 61

```
cac cac cac cac cac cac tga                                      21
His His His His His His
```

```
<210> SEQ ID NO 62
<211> LENGTH: 6
<212> TYPE: PRT
<213> ORGANISM: Artificial Sequence
<220> FEATURE:
<223> OTHER INFORMATION: Synthetic Construct

<400> SEQUENCE: 62

His His His His His His
1               5

<210> SEQ ID NO 63
<211> LENGTH: 75
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(75)

<400> SEQUENCE: 63 cac cac cac cac cac cac ggt gga ggt tct ggc ggt gga tcg gga ggt      48
His His His His His His Gly Gly Gly Ser Gly Gly Gly Ser Gly Gly
1               5                   10                  15 tca cat cac cat cac cat cac ggt tga                                   75
Ser His His His His His His Gly
            20

<210> SEQ ID NO 64
<211> LENGTH: 24
<212> TYPE: PRT
<213> ORGANISM: Artificial Sequence
<220> FEATURE:
<223> OTHER INFORMATION: Synthetic Construct

<400> SEQUENCE: 64

His His His His His His Gly Gly Gly Ser Gly Gly Gly Ser Gly Gly
1               5                   10                  15

Ser His His His His His His Gly
            20

<210> SEQ ID NO 65
<211> LENGTH: 367
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(366)

<400> SEQUENCE: 65 caa gtt cag ctt caa gaa tct ggc ggc gga agc gtt cag gct ggc gga      48
Gln Val Gln Leu Gln Glu Ser Gly Gly Gly Ser Val Gln Ala Gly Gly
1               5                   10                  15 tct ctg aga ctg agc tgt gtg gcc agc ggc tac acc gat agc aca tac      96
Ser Leu Arg Leu Ser Cys Val Ala Ser Gly Tyr Thr Asp Ser Thr Tyr
            20                  25                  30 tgc gtc ggc tgg ttc aga cag gcc cct ggc aaa gag aga gag ggc gtc     144
Cys Val Gly Trp Phe Arg Gln Ala Pro Gly Lys Glu Arg Glu Gly Val
        35                  40                  45 gcc aga atc aac acc atc agc ggc aga cct tgg tac gcc gac tct gtg     192
Ala Arg Ile Asn Thr Ile Ser Gly Arg Pro Trp Tyr Ala Asp Ser Val
```

```
                    50                  55                  60
aag ggc aga ttc aca atc agc cag gac aac agc aag aac acc gtg ttc    240
Lys Gly Arg Phe Thr Ile Ser Gln Asp Asn Ser Lys Asn Thr Val Phe
 65                  70                  75                  80 ctg cag atg aac agc ctg aag cct gag gac acc gcc atc tac tac tgc    288
Leu Gln Met Asn Ser Leu Lys Pro Glu Asp Thr Ala Ile Tyr Tyr Cys
                 85                  90                  95 acc ctg acc acc gcc aac agc aga ggc ttt tgt tcc ggc ggc tac aac    336
Thr Leu Thr Thr Ala Asn Ser Arg Gly Phe Cys Ser Gly Gly Tyr Asn
            100                 105                 110 tac aaa ggc cag ggc caa gtg acc gtg tct g                          367
Tyr Lys Gly Gln Gly Gln Val Thr Val Ser
        115                 120
```

<210> SEQ ID NO 66
<211> LENGTH: 122
<212> TYPE: PRT
<213> ORGANISM: Artificial Sequence
<220> FEATURE:
<223> OTHER INFORMATION: Synthetic Construct

<400> SEQUENCE: 66

```
Gln Val Gln Leu Gln Glu Ser Gly Gly Gly Ser Val Gln Ala Gly Gly
 1               5                  10                  15

Ser Leu Arg Leu Ser Cys Val Ala Ser Gly Tyr Thr Asp Ser Thr Tyr
            20                  25                  30

Cys Val Gly Trp Phe Arg Gln Ala Pro Gly Lys Glu Arg Glu Gly Val
        35                  40                  45

Ala Arg Ile Asn Thr Ile Ser Gly Arg Pro Trp Tyr Ala Asp Ser Val
    50                  55                  60

Lys Gly Arg Phe Thr Ile Ser Gln Asp Asn Ser Lys Asn Thr Val Phe
 65                  70                  75                  80

Leu Gln Met Asn Ser Leu Lys Pro Glu Asp Thr Ala Ile Tyr Tyr Cys
                 85                  90                  95

Thr Leu Thr Thr Ala Asn Ser Arg Gly Phe Cys Ser Gly Gly Tyr Asn
            100                 105                 110

Tyr Lys Gly Gln Gly Gln Val Thr Val Ser
        115                 120
```

<210> SEQ ID NO 67
<211> LENGTH: 29811
<212> TYPE: DNA
<213> ORGANISM: SARS-CoV-2

<400> SEQUENCE: 67

```
cttcccaggt aacaaaccaa ccaactttcg atctcttgta gatctgttct ctaaacgaac    60
tttaaaatct gtgtggctgt cactcggctg catgcttagt gcactcacgc agtataatta   120
ataactaatt actgtcgttg acaggacacg agtaactcgt ctatcttctg caggctgctt   180
acggtttcgt ccgtgttgca gccgatcatc agcacatcta gtttcgtcc gggtgtgacc    240 gaaaggtaag atggagagcc ttgtccctgg tttcaacgag aaaacacacg tccaactcag   300
tttgcctgtt ttacaggttc gcgacgtgct cgtacgtggc tttggagact ccgtggagga   360
ggtcttatca gaggcacgtc aacatcttaa agatggcact tgtggcttag tagaagttga   420
aaaaggcgtt ttgcctcaac ttgaacagcc ctatgtgttc atcaaacgtt cggatgctcg   480
aactgcacct catggtcatg ttatggttga gctggtagca gaactcgaag gcattcagta   540
cggtcgtagt ggtgagacac ttggtgtcct tgtccctcat gtgggcgaaa taccagtggc   600
```

```
ttaccgcaag gttcttcttc gtaagaacgg taataaagga gctggtggcc atagttacgg      660
cgccgatcta aagtcatttg acttaggcga cgagcttggc actgatcctt atgaagattt      720
tcaagaaaac tggaacacta aacatagcag tggtgttacc cgtgaactca tgcgtgagct      780
taacggaggg gcatacactc gctatgtcga taacaacttc tgtggccctg atggctaccc      840
tcttgagtgc attaaagacc ttctagcacg tgctggtaaa gcttcatgca ctttgtccga      900
acaactggac tttattgaca ctaagagggg tgtatactgc tgccgtgaac atgagcatga      960
aattgcttgg tacacggaac gttctgaaaa gagctatgaa ttgcagacac cttttgaaat     1020
taaattggca agaaatttg acaccttcaa tggggaatgt ccaaattttg tatttccctt      1080
aaattccata atcaagacta ttcaaccaag ggttgaaaag aaaaagcttg atggctttat     1140
gggtagaatt cgatctgtct atccagttgc gtcaccaaat gaatgcaacc aaatgtgcct     1200
ttcaactctc atgaagtgtg atcattgtgg tgaaacttca tggcagacgg gcgattttgt     1260
taaagccact tgcgaatttt gtggcactga gaatttgact aaagaaggtg ccactacttg     1320
tggttactta ccccaaaatg ctgttgttaa aatttattgt ccagcatgtc acaattcaga     1380
agtaggacct gagcatagtc ttgccgaata ccataatgaa tctggcttga aaaccattct     1440
tcgtaagggt ggtcgcacta ttgcctttgg aggctgtgtg ttctcttatg ttggttgcca     1500
taacaagtgt gcctattggg ttccacgtgc tagcgctaac ataggttgta accatacagg     1560
tgttgttgga gaaggttccg aaggtcttaa tgacaacctt cttgaaatac tccaaaaaga     1620
gaaagtcaac atcaatattg ttggtgactt taaacttaat gaagagatcg ccattatttt     1680
ggcatctttt tctgcttcca caagtgcttt tgtggaaact gtgaaaggtt tggattataa     1740
agcattcaaa caaattgttg aatcctgtgg taattttaaa gttacaaaag gaaaagctaa     1800
aaaaggtgcc tggaatattg gtgaacagaa atcaatactg agtcctcttt atgcatttgc     1860
atcagaggct gctcgtgttg tacgatcaat tttctcccgc actcttgaaa ctgctcaaaa     1920
ttctgtgcgt gttttacaga aggccgctat aacaatacta gatggaattt cacagtattc     1980
actgagactc attgatgcta tgatgttcac atctgatttg gctactaaca atctagttgt     2040
aatggcctac attacaggtg gtgttgttca gttgacttcg cagtggctaa ctaacatctt     2100
tggcactgtt tatgaaaaac tcaaacccgt ccttgattgg cttgaagaga gtttaagga      2160 aggtgtagag tttcttagag acggttggga aattgttaaa tttatctcaa cctgtgcttg     2220
tgaaattgtc ggtggacaaa ttgtcacctg tgcaaggaa attaaggaga gtgttcagac      2280
attctttaag cttgtaaata aattttggc tttgtgtgct gactctatca ttattggtgg      2340
agctaaactt aaagccttga atttaggtga acatttgtc acgcactcaa agggattgta     2400
cagaaagtgt gttaaatcca gagaagaaac tggcctactc atgcctctaa agcccaaa      2460 agaaattatc ttcttagagg gagaaacact tcccacagaa gtgttaacag aggaagttgt     2520
cttgaaaact ggtgatttac aaccattaga acaacctact agtgaagctg ttgaagctcc     2580
attggttggt acaccagttt gtattaacgg gcttatgttg ctcgaaatca agacacaga      2640 aaagtactgt gcccttgcac ctaatatgat ggtaacaaac aataccttca cactcaaagg     2700
cggtgcacca acaaaggtta cttttggtga tgacactgtg atagaagtgc aaggttacaa     2760
gagtgtgaat atcacttttg aacttgatga aaggattgat aaagtactta tgagaagtg      2820 ctctgcctat acagttgaac tcggtacaga agtaaatgag ttcgcctgtg ttgtggcaga     2880
tgctgtcata aaaactttgc aaccagtatc tgaattactt acaccactgg gcattgattt     2940
```

```
agatgagtgg agtatggcta catactactt atttgatgag tctggtgagt ttaaattggc    3000
ttcacatatg tattgttctt tctaccctcc agatgaggat gaagaagaag gtgattgtga    3060
agaagaagag tttgagccat caactcaata tgagtatggt actgaagatg attaccaagg    3120
taaacctttg gaatttggtg ccacttctgc tgctcttcaa cctgaagaag agcaagaaga    3180
agattggtta gatgatgata gtcaacaaac tgttggtcaa caagacggca gtgaggacaa    3240
tcagacaact actattcaaa caattgttga ggttcaacct caattagaga tggaacttac    3300
accagttgtt cagactattg aagtgaatag ttttagtggt tatttaaaac ttactgacaa    3360
tgtatacatt aaaaatgcag acattgtgga agaagctaaa aaggtaaaac caacagtggt    3420
tgttaatgca gccaatgttt accttaaaca tggaggaggt gttgcaggag ccttaaataa    3480
ggctactaac aatgccatgc aagttgaatc tgatgattac atagctacta atggaccact    3540
taaagtgggt ggtagttgtg ttttaagcgg acacaatctt gctaaacact gtcttcatgt    3600
tgtcggccca aatgttaaca aaggtgaaga cattcaactt cttaagagtg cttatgaaaa    3660
ttttaatcag cacgaagttc tacttgcacc attattatca gctggtattt ttggtgctga    3720
ccctatacat tctttaagag tttgtgtaga tactgttcgc acaaatgtct acttagctgt    3780
ctttgataaa aatctctatg acaaacttgt ttcaagcttt ttggaaatga gagtgaaaa    3840 gcaagttgaa caaagatcg ctgagattcc taaagaggaa gttaagccat ttataactga    3900
aagtaaacct tcagttgaac agagaaaaca agatgataag aaaatcaaag cttgtgttga    3960
agaagttaca caactctgg aagaaactaa gttcctcaca gaaaacttgt tactttatat    4020
tgacattaat ggcaatcttc atccagattc tgccactctt gttagtgaca ttgacatcac    4080
tttcttaaag aaagatgctc catatatagt gggtgatgtt gttcaagagg gtgttttaac    4140
tgctgtggtt atacctacta aaaggctgg tggcactact gaaatgctag cgaaagcttt    4200
gagaaaagtg ccaacagaca attatataac cacttacccg ggtcagggtt taaatggtta    4260
cactgtagag gaggcaaaga cagtgcttaa aaagtgtaaa agtgccttt acattctacc    4320 atctattatc tctaatgaga agcaagaaat tcttggaact gtttcttgga atttgcgaga    4380
aatgcttgca catgcagaag aaacacgcaa attaatgcct gtctgtgtgg aaactaaagc    4440
catagtttca actatacagc gtaaatataa gggtattaaa atacaagagg gtgtggttga    4500
ttatggtgct agattttact tttacaccag taaaacaact gtagcgtcac ttatcaacac    4560
acttaacgat ctaaatgaaa ctcttgttac aatgccactt ggctatgtaa cacatggctt    4620
aaatttggaa gaagctgctc ggtatatgag atctctcaaa gtgccagcta cagtttctgt    4680
ttcttcacct gatgctgtta cagcgtataa tggttatctt acttcttctt ctaaaacacc    4740
tgaagaacat tttattgaaa ccatctcact tgctggttcc tataaagatt ggtcctattc    4800
tggacaatct acacaactag gtatagaatt tcttaagaga ggtgataaaa gtgtatatta    4860
cactagtaat cctaccacat tccacctaga tggtgaagtt atcacctttg acaatcttaa    4920
gacacttctt tctttgagag aagtgaggac tattaaggtg tttacaacag tagacaacat    4980
taacctccac acgcaagttg tggacatgtc aatgacatat ggacaacagt tggtccaac    5040 ttatttggat ggagctgatg ttactaaaat aaaacctcat aattcacatg aaggtaaaac    5100 atttttatgtt ttacctaatg atgacactct acgtgttgag gcttttgagt actaccacac    5160
aactgatcct agttttctgg gtaggtacat gtcagcatta aatcacacta aaagtggaa    5220 atacccacaa gttaatggtt taacttctat taaatgggca gataacaact gttatcttgc    5280
cactgcattg ttaacactcc aacaaataga gttgaagttt aatccacctg ctctacaaga    5340
```

```
tgcttattac agagcaaggg ctggtgaagc tgctaacttt tgtgcactta tcttagccta     5400
ctgtaataag acagtaggtg agttaggtga tgttagagaa acaatgagtt acttgtttca     5460
acatgccaat ttagattctt gcaaaagagt cttgaacgtg gtgtgtaaaa cttgtggaca     5520
acagcagaca accccttaagg gtgtagaagc tgttatgtac atgggcacac tttcttatga    5580
acaatttaag aaaggtgttc agataccttg tacgtgtggt aaacaagcta caaaatatct     5640
agtacaacag gagtcacctt ttgttatgat gtcagcacca cctgctcagt atgaacttaa     5700
gcatggtaca tttacttgtg ctagtgagta cactggtaat taccagtgtg gtcactataa     5760
acatataact tctaaagaaa ctttgtattg catagacggt gctttactta caaagtcctc     5820
agaatacaaa ggtcctatta cggatgtttt ctacaaagaa acagttaca caacaaccat      5880 aaaaccagtt acttataaat tggatggtgt tgtttgtaca gaaattgacc ctaagttgga    5940
caattattat aagaaagaca attcttattt cacagagcaa ccaattgatc ttgtaccaaa     6000
ccaaccatat ccaaacgcaa gcttcgataa ttttaagttt gtatgtgata atatcaaatt    6060
tgctgatgat ttaaaccagt taactggtta taagaaacct gcttcaagag agcttaaagt   6120 tacattttc cctgacttaa atggtgatgt ggtggctatt gattataaac actacacacc      6180 ctctttaag aaaggagcta aattgttaca taaacctatt gtttggcatg ttaacaatgc       6240
aactaataaa gccacgtata aaccaaatac ctggtgtata cgttgtcttt ggagcacaaa     6300
accagttgaa acatcaaatt cgtttgatgt actgaagtca gaggacgcgc agggaatgga     6360
taatcttgcc tgcgaagatc taaaaccagt ctctgaagaa gtagtggaaa atcctaccat    6420
acagaaagac gttcttgagt gtaatgtgaa aactaccgaa gttgtaggag acattatact      6480
taaaccagca ataatagtt taaaaattac agaagaggtt ggccacacag atctaatggc      6540
tgcttatgta gacaattcta gtcttactat taagaaacct aatgaattat ctagagtatt    6600
aggtttgaaa accttgcta ctcatggttt agctgctgtt aatagtgtcc cttgggatac      6660
tatagctaat tatgctaagc ttttcttaa caaagttgtt agtacaacta ctaacatagt     6720
tacacggtgt ttaaaccgtg tttgtactaa ttatatgcct tatttctta ctttattgct     6780 acaattgtgt acttttacta gaagtacaaa ttctagaatt aaagcatcta tgccgactac   6840
tatagcaaag aatactgtta agagtgtcgg taaattttgt ctagaggctt catttaatta     6900
tttgaagtca cctaatttt ctaaactgat aaatattata atttggtttt tactattaag     6960
tgtttgccta ggttctttaa tctactcaac cgctgcttta ggtgttttaa tgtctaattt    7020
aggcatgcct tcttactgta ctggttacag agaaggctat tgaactcta ctaatgtcac      7080 tattgcaacc tactgtactg gttctatacc ttgtagtgtt tgtcttagtg gtttagattc     7140
tttagacacc tatcccttctt tagaaactat acaaattacc atttcatctt ttaaatggga   7200
tttaactgct tttggcttag ttgcagagtg gttttggca tatattcttt tcactaggtt    7260
tttctatgta cttggattgg ctgcaatcat gcaattgttt tcagctatt ttgcagtaca    7320 ttttattagt aattcttggc ttatgtggtt aataattaat cttgtacaaa tggccccgat    7380
ttcagctatg gttagaatgt acatcttctt tgcatcattt tattatgtat ggaaaagtta    7440
tgtgcatgtt gtagacggtt gtaattcatc aacttgtatg atgtgttaca acgtaatag     7500 agcaacaaga gtcgaatgta caactattgt taatggtgtt agaaggtcct tttatgtcta   7560
tgctaatgga ggtaaaggct tttgcaaact acacaattgg aattgtgtta attgtgatac    7620
attctgtgct ggtagtacat ttattagtga tgaagttgcg agagacttgt cactacagtt    7680
```

-continued

```
taaaagacca ataaatccta ctgaccagtc ttcttacatc gttgatagtg ttacagtgaa   7740
gaatggttcc atccatcttt actttgataa agctggtcaa aagacttatg aaagacattc   7800
tctctctcat tttgttaact tagacaacct gagagctaat aacactaaag gttcattgcc   7860
tattaatgtt atagtttttg atggtaaatc aaaatgtgaa gaatcatctg caaaatcagc   7920
gtctgtttac tacagtcagc ttatgtgtca acctatactg ttactagatc aggcattagt   7980
gtctgatgtt ggtgatagtg cggaagttgc agttaaaatg tttgatgctt acgttaatac   8040
gttttcatca acttttaacg taccaatgga aaaactcaaa acactagttg caactgcaga   8100
agctgaactt gcaaagaatg tgtccttaga caatgtctta tctacttttta tttcagcagc   8160 tcggcaaggg tttgttgatt cagatgtaga aactaaagat gttgttgaat gtcttaaatt   8220
gtcacatcaa tctgacatag aagttactgg cgatagttgt aataactata tgctcaccta   8280
taacaaagtt gaaaacatga caccccgtga ccttggtgct tgtattgact gtagtgcgcg   8340
tcatattaat gcgcaggtag caaaaagtca caacattgct ttgatatgga acgttaaaga   8400
tttcatgtca ttgtctgaac aactacgaaa acaaatacgt agtgctgcta aaaagaataa   8460
cttacctttt aagttgacat gtgcaactac tagacaagtt gttaatgttg taacaacaaa   8520
gatagcactt aagggtggta aaattgttaa taattggttg aagcagttaa ttaaagttac   8580
acttgtgttc cttttttgttg ctgctatttt ctatttaata acacctgttc atgtcatgtc   8640
taaacatact gacttttcaa gtgaaatcat aggatacaag gctattgatg gtggtgtcac   8700
tcgtgacata gcatctacag atacttgttt tgctaacaaa catgctgatt ttgacacatg   8760
gtttagccag cgtggtggta gttatactaa tgacaaagct tgcccattga ttgctgcagt   8820
cataacaaga gaagtgggtt ttgtcgtgcc tggtttgcct ggcacgatat acgcacaac    8880 taatggtgac tttttgcatt tcttacctag agtttttagt gcagttggta acatctgtta   8940
cacaccatca aaacttatag agtacactga ctttgcaaca tcagcttgtg ttttggctgc   9000
tgaatgtaca attttttaaag atgcttctgg taagccagta ccatattgtt atgataccaa   9060
tgtactagaa ggttctgttg cttatgaaag tttacgccct gacacacgtt atgtgctcat   9120
ggatggctct attattcaat ttcctaacac ctaccttgaa ggttctgtta gagtggtaac   9180
aacttttgat tctgagtact gtaggcacgg cacttgtgaa agatcagaag ctggtgtttg   9240
tgtatctact agtggtagat gggtacttaa caatgattat tacagatctt taccaggagt   9300
tttctgtggt gtagatgctg taaatttact tactaatatg tttacaccac taattcaacc   9360
tattggtgct ttggacatat cagcatctat agtagctggt ggtattgtag ctatcgtagt   9420
aacatgcctt gcctactatt ttatgaggtt tagaagagct tttggtgaat acagtcatgt   9480
agttgccttt aatactttac tattccttat gtcattcact gtactctgtt taacaccagt   9540
ttactcattc ttacctggtg tttattctgt tatttacttg tacttgacat tttatcttac   9600
taatgatgtt tcttttttag cacatattca gtggatggtt atgttcacac ctttagtacc   9660
tttctggata acaattgctt atatcatttg tatttccaca aagcatttct attggttctt   9720
tagtaattac ctaaagagac gtgtagtctt taatggtgtt tcctttagta cttttgaaga   9780
agctgcgctg tgcaccttttt tgttaaataa agaaatgtat ctaaagttgc gtagtgatgt   9840
gctattacct cttacgcaat ataatagata cttagctctt tataataagt acaagtattt   9900
tagtggagca atggatacaa ctagctacag agaagctgct tgttgtcatc tcgcaaaggc   9960
tctcaatgac ttcagtaact caggttctga tgttctttac caaccaccac aaacctctat   10020
cacctcagct gttttgcaga gtggttttag aaaaatggca ttcccatctg gtaaagttga   10080
```

```
gggttgtatg gtacaagtaa cttgtggtac aactacactt aacggtcttt ggcttgatga    10140
cgtagtttac tgtccaagac atgtgatctg cacctctgaa gacatgctta accctaatta    10200
tgaagattta ctcattcgta agtctaatca taatttcttg gtacaggctg gtaatgttca    10260
actcagggtt attggacatt ctatgcaaaa ttgtgtactt aagcttaagg ttgatacagc    10320
caatcctaag acacctaagt ataagtttgt tcgcattcaa ccaggacaga cttttttcagt   10380 gttagcttgt tacaatggtt caccatctgg tgtttaccaa tgtgctatga ggcccaattt    10440
cactattaag ggttcattcc ttaatggttc atgtggtagt gttggttttta acatagatta   10500 tgactgtgtc tcttttttgtt acatgcacca tatggaatta ccaactggag ttcatgctgg   10560
cacagactta gaaggtaact tttatggacc ttttgttgac aggcaaacag cacaagcagc    10620
tggtacggac acaactatta cagttaatgt tttagcttgg ttgtacgctg ctgttataaa    10680
tggagacagg tggtttctca atcgatttac cacaactctt aatgacttta accttgtggc    10740
tatgaagtac aattatgaac ctctaacaca agaccatgtt gacatactag gacctctttc    10800
tgctcaaact ggaattgccg ttttagatat gtgtgcttca ttaaaagaat tactgcaaaa    10860
tggtatgaat ggacgtacca tattgggtag tgctttatta aagatgaat ttacacccttt    10920 tgatgttgtt agacaatgct caggtgttac tttccaaagt gcagtgaaaa gaacaatcaa    10980
gggtacacac cactggttgt tactcacaat tttgacttca cttttagttt tagtccagag    11040
tactcaatgg tctttgttct tttttttgta tgaaaatgcc ttttttacctt ttgctatggg    11100 tattattgct atgtctgctt ttgcaatgat gtttgtcaaa cataagcatg catttctctg    11160 tttgttttttg ttaccttctc ttgccactgt agcttatttt aatatggtct atatgcctgc    11220
tagttgggtg atgcgtatta tgacatggtt ggatatggtt gatactagtt tgtctggttt    11280
taagctaaaa gactgtgtta tgtatgcatc agctgtagtg ttactaatcc ttatgacagc    11340
aagaactgtg tatgatgatg gtgctaggag agtgtggaca cttatgaatg tcttgacact    11400
cgtttataaa gtttattatg gtaatgcttt agatcaagcc atttccatgt gggctcttat    11460
aatctctgtt acttctaact actcaggtgt agttacaact gtcatgtttt tggccagagg    11520
tattgttttt atgtgtgttg agtattgccc tatttttctc ataactggta atacacttca    11580
gtgtataatg ctagtttatt gtttcttagg ctattttttgt acttgttact ttggcctctt    11640
ttgtttactc aaccgctact ttagactgac tcttggtgtt tatgattact agttttctac    11700
acaggagttt agatatatga attcacaggg actactccca cccaagaata gcatagatgc    11760
cttcaaactc aacattaaat tgtgggtgt tggtggcaaa ccttgtatca agtagccac     11820 tgtacagtct aaaatgtcag atgtaaagtg cacatcagta gtcttactct cagttttgca    11880
acaactcaga gtagaatcat catctaaatt gtgggctcaa tgtgtccagt tacacaatga    11940
cattctctta gctaaagata ctactgaagc ctttgaaaaa atggtttcac tactttctgt    12000
tttgctttcc atgcagggtg ctgtagacat aaacaagctt tgtgaagaaa tgctggacaa    12060
cagggcaacc ttacaagcta tagcctcaga gtttagttcc cttccatcat atgcagcttt    12120
tgctactgct caagaagctt atgagcaggc tgttgctaat ggtgattctg aagttgttct    12180
taaaaagttg aagaagtctt tgaatgtggc taaatctgaa tttgaccgtg atgcagccat    12240
gcaacgtaag ttggaaaaga tggctgatca agctatgacc caaatgtata acaggctag    12300 atctgaggac aagagggcaa aagttactag tgctatgcag acaatgcttt tcactatgct    12360
tagaaagttg gataatgatg cactcaacaa cattatcaac aatgcaagag atggttgtgt    12420
```

```
tcccttgaac ataatacctc ttacaacagc agccaaacta atggttgtca taccagacta   12480
taacacatat aaaaatacgt gtgatggtac aacatttact tatgcatcag cattgtggga   12540
aatccaacag gttgtagatg cagatagtaa aattgttcaa cttagtgaaa ttagtatgga   12600
caattcacct aatttagcat ggcctcttat tgtaacagct ttaagggcca attctgctgt   12660
caaattacag aataatgagc ttagtcctgt tgcactacga cagatgtctt gtgctgccgg   12720
tactacacaa actgcttgca ctgatgacaa tgcgttagct tactacaaca caacaaaggg   12780
aggtaggttt gtacttgcac tgttatccga tttacaggat ttgaaatggg ctagattccc   12840
taagagtgat ggaactggta ctatctatac agaactggaa ccaccttgta ggtttgttac   12900
agacacacct aaaggtccta agtgaagta tttatacttt attaaaggat taaacaacct   12960
aaatagaggt atggtacttg gtagtttagc tgccacagta cgtctacaag ctggtaatgc   13020
aacagaagtg cctgccaatt caactgtatt atctttctgt gcttttgctg tagatgctgc   13080
taaagcttac aaagattatc tagctagtgg gggacaacca atcactaatt gtgttaagat   13140
gttgtgtaca cacactggta ctggtcaggc aataacagtt acaccggaag ccaatatgga   13200
tcaagaatcc tttggtggtg catcgtgttg tctgtactgc cgttgccaca tagatcatcc   13260
aaatcctaaa ggattttgtg acttaaaagg taagtatgta caaataccta aacttgtgc   13320 taatgaccct gtgggtttta cacttaaaaa cacagtctgt accgtctgcg gtatgtggaa   13380
aggttatggc tgtagttgtg atcaactccg cgaacccatg cttcagtcag ctgatgcaca   13440 atcgtttta aacgggtttg cggtgtaagt gcagcccgtc ttacaccgtg cggcacaggc   13500
actagtactg atgtcgtata cagggctttt gacatctaca atgataaagt agctggtttt   13560
gctaaattcc taaaaactaa ttgttgtcgc ttccaagaaa aggacgaaga tgacaattta   13620
attgattctt actttgtagt taagagacac actttctcta actaccaaca tgaagaaaca   13680
atttataatt tacttaagga ttgtccagct gttgctaaac atgacttctt aagtttaga   13740 atagacggtg acatggtacc acatatatca cgtcaacgtc ttactaaata cacaatggca   13800
gacctcgtct atgctttaag gcatttgat gaaggtaatt gtgacacatt aaaagaaata   13860
cttgtcacat acaattgttg tgatgatgat tatttcaata aaaaggactg gtatgatttt   13920
gtagaaaacc cagatatatt acgcgtatac gccaacttag gtgaacgtgt acgccaagct   13980
ttgttaaaaa cagtacaatt ctgtgatgcc atgcgaaatg ctggtattgt tggtgtactg   14040
acattagata atcaagatct caatggtaac tggtatgatt tcggtgattt catacaaacc   14100
acgccaggta gtggagttcc tgttgtagat tcttattatt cattgttaat gcctatatta   14160
accttgacca gggctttaac tgcagagtca catgttgaca ctgacttaac aaagccttac   14220
attaagtggg atttgttaaa atatgacttc acggaagaga ggttaaaact ctttgaccgt   14280
tattttaaat attgggatca gacataccac ccaaattgtg ttaactgttt ggatgacaga   14340
tgcattctgc attgtgcaaa ctttaatgtt ttattctcta cagtgttccc acctacaagt   14400
tttggaccac tagtgagaaa aatatttgtt gatggtgttc catttgtagt ttcaactgga   14460
taccacttca gagagctagg tgttgtacat aatcaggatg taaacttaca tagctctaga   14520
cttagtttta aggaattact tgtgtatgct gctgacccatg ctatgcacgc tgcttctggt   14580
aatctattac tagataaacg cactacgtgc ttttcagtag ctgcacttac taacaatgtt   14640
gcttttcaaa ctgtcaaacc cggtaatttt aacaaagact tctatgactt tgctgtgtct   14700
aagggtttct ttaaggaagg aagttctgtt gaattaaaac acttcttctt tgctcaggat   14760
ggtaatgctg ctatcagcga ttatgactac tatcgttata atctaccaac aatgtgtgat   14820
```

```
atcagacaac tactatttgt agttgaagtt gttgataagt actttgattg ttacgatggt    14880
ggctgtatta atgctaacca agtcatcgtc aacaacctag acaaatcagc tggttttcca    14940
tttaataaat ggggtaaggc tagactttat tatgattcaa tgagttatga ggatcaagat    15000
gcacttttcg catatacaaa acgtaatgtc atccctacta taactcaaat gaatcttaag    15060
tatgccatta gtgcaaagaa tagagctcgc accgtagctg gtgtctctat ctgtagtact    15120
atgaccaata gacagtttca tcaaaaatta ttgaaatcaa tagccgccac tagaggagct    15180
actgtagtaa ttggaacaag caaattctat ggtggttggc acaacatgtt aaaaactgtt    15240
tatagtgatg tagaaaaccc tcaccttatg ggttgggatt atcctaaatg tgatagagcc    15300
atgcctaaca tgcttagaat tatggcctca cttgttcttg ctcgcaaaca tacaacgtgt    15360
tgtagcttgt cacaccgttt ctatagatta gctaatgagt gtgctcaagt attgagtgaa    15420
atggtcatgt gtggcggttc actatatgtt aaaccaggtg gaacctcatc aggagatgcc    15480
acaactgctt atgctaatag tgttttttaac atttgtcaag ctgtcacggc caatgttaat    15540
gcactttat ctactgatgg taacaaaatt gccgataagt atgtccgcaa tttacaacac    15600
agactttatg agtgtctcta tagaaataga gatgttgaca cagactttgt gaatgagttt    15660
tacgcatatt tgcgtaaaca tttctcaatg atgatactct ctgacgatgc tgttgtgtgt    15720
ttcaatagca cttatgcatc tcaaggtcta gtggctagca taagaacttt aagtcagtt    15780
ctttattatc aaaacaatgt ttttatgtct gaagcaaaat gttggactga gactgacctt    15840
actaaaggac ctcatgaatt ttgctctcaa catacaatgc tagttaaaca gggtgatgat    15900
tatgtgtacc ttccttaccc agatccatca agaatcctag gggccggctg ttttgtagat    15960
gatatcgtaa aaacagatgg tacacttatg attgaacggt tcgtgtcttt agctatagat    16020
gcttacccac ttactaaaca tcctaatcag gagtatgctg atgtctttca tttgtactta    16080
caatacataa gaaagctaca tgatgagtta acaggacaca tgttagacat gtattctgtt    16140
atgcttacta atgataacac ttcaaggtat tgggaacctg agttttatga ggctatgtac    16200
acaccgcata cagtcttaca ggctgttggg cttgtgttc tttgcaattc acagacttca    16260
ttaagatgtg gtgcttgcat acgtagacca ttccttatgt gtaaatgctg ttacgaccat    16320
gtcatatcaa catcacataa attagtcttg tctgttaatc cgtatgtttg caatgctcca    16380
ggttgtgatg tcacagatgt gactcaactt tacttaggag gtatgagcta ttattgtaaa    16440
tcacataaac cacccattag ttttccattg tgtgctaatg acaagttt tggtttatat    16500
aaaaatacat gtgttggtag cgataatgtt actgacttta atgcaattgc aacatgtgac    16560
tggacaaatg ctggtgatta cattttagct aacacctgta ctgaaagact caagcttttt    16620
gcagcagaaa cgctcaaagc tactgaggag acatttaaac tgtcttatgg tattgctact    16680
gtacgtgaag tgctgtctga cagagaatta catctttcat gggaagttgg taaacctaga    16740
ccaccactta accgaaatta tgtctttact ggttatcgtg taactaaaaa cagtaaagta    16800
caaataggag agtacacctt tgaaaaaggt gactatggtg atgctgttgt ttaccgaggt    16860
acaacaactt acaaattaaa tgttggtgat tatttgtgc tgacatcaca tacagtaatg    16920
ccattaagtg cacctacact agtgccacaa gagcactatg ttagaattac tggcttatac    16980
ccaacactca atatctcaga tgagtttttct agcaatgttg caaattatca aaaggttggt    17040
atgcaaaagt attctacact ccagggacca cctggtactg gtaagagtca ttttgctatt    17100
ggcctagctc tctactaccc ttctgctcgc atagtgtata cagcttgctc tcatgccgct    17160
```

```
gttgatgcac tatgtgagaa ggcattaaaa tatttgccta tagataaatg tagtagaatt   17220
atacctgcac gtgctcgtgt agagtgtttt gataaattca aagtgaattc aacattagaa   17280
cagtatgtct tttgtactgt aaatgcattg cctgagacga cagcagatat agttgtcttt   17340
gatgaaattt caatggccac aaattatgat ttgagtgttg tcaatgccag attacgtgct   17400
aagcactatg tgtacattgg cgaccctgct caattacctg caccacgcac attgctaact   17460
aagggcacac tagaaccaga atatttcaat tcagtgtgta gacttatgaa aactataggt   17520
ccagacatgt tcctcggaac ttgtcggcgt tgtcctgctg aaattgttga cactgtgagt   17580
gctttggttt atgataataa gcttaaagca cataaagaca aatcagctca atgctttaaa   17640
atgttttata agggtgttat cacgcatgat gtttcatctg caattaacag gccacaaata   17700
ggcgtggtaa gagaattcct tacacgtaac cctgcttgga gaaaagctgt ctttatttca   17760
ccttataatt cacagaatgc tgtagcctca aagattttgg gactaccaac tcaaactgtt   17820
gattcatcac agggctcaga atatgactat gtcatattca ctcaaaccac tgaaacagct   17880
cactcttgta atgtaaacag atttaatgtt gctattacca gagcaaaagt aggcatactt   17940
tgcataatgt ctgatagaga cctttatgac aagttgcaat ttacaagtct tgaaattcca   18000
cgtaggaatg tggcaacttt acaagctgaa atgtaacag gactctttaa agattgtagt   18060
aaggtaatca ctgggttaca tcctacacag gcacctacac acctcagtgt tgacactaaa   18120
ttcaaaactg aaggtttatg tgttgacata cctggcatac taaggacat gacctataga   18180 agactcatct ctatgatggg ttttaaaatg aattatcaag ttaatggtta ccctaacatg   18240
tttatcaccc gcgaagaagc tataagacat gtacgtgcat ggattggctt cgatgtcgag   18300
gggtgtcatg ctactagaga agctgttggt accaatttac ctttacagct aggttttttct   18360 acaggtgtta acctagttgc tgtacctaca ggttatgttg atacacctaa taatacagat   18420 tttttccagag ttagtgctaa accaccgcct ggagatcaat ttaaacacct cataccactt   18480
atgtacaaag gacttccttg gaatgtagtg cgtataaaga ttgtacaaat gttaagtgac   18540
acacttaaaa atctctctga cagagtcgta tttgtcttat gggcacatgg ctttgagttg   18600
acatctatga agtattttgt gaaaatagga cctgagcgca cctgttgtct atgtgataga   18660
cgtgccacat gcttttccac tgcttcagac acttatgcct gttggggccatca ttctattgga   18720 tttgattacg tctataatcc gtttatgatt gatgttcaac aatggggttt tacaggtaac   18780
ctacaaagca accatgatct gtattgtcaa gtccatggta atgcacatgt agctagttgt   18840
gatgcaatca tgactaggtg tctagctgtc cacgagtgct tgttaagcg tgttgactgg   18900 actattgaat atcctataat tggtgatgaa ctgaagatta atgcggcttg tagaaaggtt   18960
caacacatgg ttgttaaagc tgcattatta gcagacaaat tcccagttct tcacgacatt   19020
ggtaacccta aagctattaa gtgtgtacct caagctgatg tagaatggaa gttctatgat   19080
gcacagcctt gtagtgacaa agcttataaa atagaagaat tattctatte ttatgccaca   19140 cattctgaca aattcacaga tggtgtatgc ctattttgga attgcaatgt cgatagatat   19200
cctgctaatt ccattgtttg tagatttgac actagagtgc tatctaaccct taacttgcct   19260 ggttgtgatg gtggcagttt gtatgtaaat aaacatgcat tccacacacc agcttttgat   19320
aaaagtgctt ttgttaattt aaaacaatta ccatttttct attactctga cagtccatgt   19380
gagtctcatg gaaaacaagt agtgtcagat atagattatg taccactaaa gtctgctacg   19440
tgtataacac gttgcaattt aggtggtgct gtctgtagac atcatgctaa tgagtacaga   19500
ttgtatctcg atgcttataa catgatgatc tcagctggct ttagcttgtg ggtttacaaa   19560
```

```
caatttgata cttataacct ctggaacact tttacaagac ttcagagttt agaaaatgtg   19620
gcttttaatg ttgtaaataa gggacacttt gatggacaac agggtgaagt accagtttct   19680
atcattaata acactgttta cacaaaagtt gatggtgttg atgtagaatt gtttgaaaat   19740
aaaacaacat tacctgttaa tgtagcattt gagctttggg ctaagcgcaa cattaaacca   19800
gtaccagagg tgaaaatact caataatttg ggtgtggaca ttgctgctaa tactgtgatc   19860
tgggactaca aaagagatgc tccagcacat atatctacta ttggtgtttg ttctatgact   19920
gacatagcca agaaaccaac tgaaacgatt tgtgcaccac tcactgtctt ttttgatggt   19980
agagttgatg tcaagtagac ttatttagaa atgcccgta atggtgttct tattacagaa    20040
ggtagtgtta aaggtttaca accatctgta ggtcccaaac aagctagtct aatggagtc     20100 acattaattg gagaagccgt aaaaacacag ttcaattatt ataagaaagt tgatggtgtt    20160
gtccaacaat tacctgaaac ttactttact cagagtagaa atttacaaga atttaaaccc    20220
aggagtcaaa tggaaattga tttcttagaa ttagctatgg atgaattcat tgaacggtat    20280
aaattagaag gctatgcctt cgaacatatc gtttatggag attttagtca tagtcagtta    20340
ggtggtttac atctactgat tggactagct aaacgtttta aggaatcacc ttttgaatta    20400
gaagatttta ttcctatgga cagtacagtt aaaaactatt tcataacaga tgcgcaaaca    20460
ggttcatcta agtgtgtgtg ttctgttatt gatttattac ttgatgattt tgttgaaata    20520
ataaaatccc aagatttatc tgtagtttct aaggttgtca aagtgactat tgactataca    20580
gaaatttcat ttatgctttg gtgtaaagat ggccatgtag aaacatttta cccaaaatta    20640
caatctagtc aagcgtggca accgggtgtt gctatgccta atctttacaa aatgcaaaga    20700
atgctattag aaaagtgtga ccttcaaaat tatggtgata gtgcaacatt acctaaaggc    20760
ataatgatga atgtcgcaaa atatactcaa ctgtgtcaat atttaaacac attaacatta    20820 gctgtacccct ataatatgag agttatacat tttggtgctg gttctgataa aggagttgca   20880
ccaggtacag ctgtttttaag acagtggttg cctacgggta cgctgcttgt cgattcagat   20940
cttaatgact ttgtctctga tgcagattca actttgattg gtgattgtgc aactgtacat    21000
acagctaata aatgggatct cattattagt gatatgtacg accctaagac taaaaatgtt    21060
acaaaagaaa atgactctaa agagggtttt tcacttaca tttgtgggtt tatacaacaa    21120
aagctagctc ttgagggttc cgtggctata aagataacag aacattcttg gaatgctgat    21180
ctttataagc tcatgggaca cttcgcatgg tggacagcct tgttactaa tgtgaatgcg    21240 tcatcatctg aagcattttt aattggatgt aattatcttg gcaaaccacg cgaacaaata    21300
gatggttatg tcatgcatgc aaattacata ttttggagga atacaaatcc aattcagttg    21360
tcttcctatt ctttatttga catgagtaaa tttccccctta aattaagggg tactgctgtt    21420
atgtctttaa aagaaggtca aatcaatgat atgatttat ctcttcttag taaaggtaga     21480
cttataatta gagaaaacaa cagagttgtt atttctagtg atgttcttgt taacaactaa    21540
acgaacaatg tttgtttttc ttgttttatt gccactagtc tctagtcagt gtgttaatct    21600
tacaaccaga actcaattac cccctgcata cactaattct ttcacacgtg gtgtttatta    21660
ccctgacaaa gttttcagat cctcagtttt acattcaact caggacttgt tcttaccttt    21720
cttttccaat gttacttggt tccatgctat acatgtctct gggaccaatg gtactaagag    21780
gtttgataac cctgtcctac catttaatga tggtgtttat tttgcttcca ctgagaagtc    21840
taacataata agaggctgga tttttggtac tactttagat tcgaagaccc agtccctact    21900
```

```
tattgttaat aacgctacta atgttgttat taaagtctgt gaatttcaat tttgtaatga   21960 tccattttg ggtgtttatt accacaaaaa caacaaaagt tggatggaaa gtgagttcag    22020
agtttattct agtgcgaata attgcactt tgaatatgtc tctcagcctt ttcttatgga   22080
ccttgaagga aaacagggta atttcaaaaa tcttagggaa tttgtgttta agaatattga   22140
tggttatttt aaaatatatt ctaagcacac gcctattaat ttagtgcgtg atctccctca   22200 gggttttcg gctttagaac cattggtaga tttgccaata ggtattaaca tcactaggtt    22260 tcaaactta cttgctttac atagaagtta tttgactcct ggtgattctt cttcaggttg    22320
gacagctggt gctgcagctt attatgtggg ttatcttcaa cctaggactt ttctattaaa   22380
atataatgaa aatggaacca ttacagatgc tgtagactgt gcacttgacc ctctctcaga   22440
aacaaagtgt acgttgaaat ccttcactgt agaaaaagga atctatcaaa cttctaactt   22500
tagagtccaa ccaacagaat ctattgttag atttcctaat attacaaact tgtgcccttt   22560
tggtgaagtt tttaacgcca ccagatttgc atctgtttat gcttggaaca ggaagagaat   22620
cagcaactgt gttgctgatt attctgtcct atataattcc gcatcatttt ccacttttaa   22680
gtgttatgga gtgtctccta ctaaattaaa tgatctctgc tttactaatg tctatgcaga   22740
ttcatttgta attagaggtg atgaagtcag acaaatcgct ccagggcaaa ctggaaagat   22800
tgctgattat aattataaat taccagatga ttttacaggc tgcgttatag cttggaattc   22860
taacaatctt gattctaagg ttggtggtaa ttataattac ctgtatagat tgtttaggaa   22920
gtctaatctc aaaccttttg agagagatat ttcaactgaa atctatcagg ccggtagcac   22980
accttgtaat ggtgttgaag ttttaattg ttactttcct ttacaatcat atggtttcca   23040
acccactaat ggtgttggtt accaaccata cagagtagta gtactttctt ttgaacttct   23100
acatgcacca gcaactgttt gtggacctaa aaagtctact aatttggtta aaacaaatg   23160 tgtcaatttc aacttcaatg gtttaacagg cacaggtgtt cttactgagt ctaacaaaaa   23220
gtttctgcct ttccaacaat tggcagaga cattgctgac actactgatg ctgtccgtga   23280
tccacagaca cttgagattc ttgacattac accatgttct tttggtggtg tcagtgttat   23340
aacaccagga acaaatactt ctaaccaggt tgctgttctt tatcaggatg ttaactgcac   23400
agaagtccct gttgctattc atgcagatca acttactcct acttggcgtg tttattctac   23460
aggttctaat gtttttcaaa cacgtgcagg ctgtttaata ggggctgaac atgtcaacaa   23520
ctcatatgag tgtgacatac ccattggtgc aggtatatgc gctagttatc agactcagac   23580
taattctcct cggcgggcac gtagtgtagc tagtcaatcc atcattgcct acactatgtc   23640
acttggtgca gaaaattcag ttgcttactc taataactct attgccatac ccacaaattt   23700
tactattagt gttaccacag aaattctacc agtgtctatg accaagacat cagtagattg   23760
tacaatgtac atttgtggtg attcaactga atgcagcaat ctttttgttgc aatatggcag   23820 tttttgtaca caattaaacc gtgctttaac tggaatagct gttgaacaag acaaaaacac   23880
ccaagaagtt tttgcacaag tcaaacaaat ttacaaaaca ccaccaatta aagattttgg   23940
tggttttaat ttttcacaaa tattaccaga tccatcaaaa ccaagcaaga ggtcatttat   24000
tgaagatcta ctttttcaata aagtgacact tgcagatgct ggcttcatca acaatatgg   24060 tgattgcctt ggtgatattg ctgctagaga cctcatttgt gcacaaaagt taacggcct   24120 tactgttttg ccacctttgc tcacagatga aatgattgct caatacactt ctgcactgtt   24180
agcgggtaca atcacttctg gttggaccctt tggtgcaggt gctgcattac aaataccatt   24240
tgctatgcaa atggcttata ggtttaatgg tattggagtt acacagaatg ttctctatga   24300
```

```
gaaccaaaaa ttgattgcca accaatttaa tagtgctatt ggcaaaattc aagactcact   24360
ttcttccaca gcaagtgcac ttggaaaact tcaagatgtg gtcaaccaaa atgcacaagc   24420
tttaaacacg cttgttaaac aacttagctc caattttggt gcaatttcaa gtgttttaaa   24480
tgatatcctt tcacgtcttg acaaagttga ggctgaagtg caaattgata ggttgatcac   24540
aggcagactt caaagtttgc agacatatgt gactcaacaa ttaattagag ctgcagaaat   24600
cagagcttct gctaatcttg ctgctactaa aatgtcagag tgtgtacttg gacaatcaaa   24660
aagagttgat ttttgtggaa agggctatca tcttatgtcc ttccctcagt cagcacctca   24720
tggtgtagtc ttcttgcatg tgacttatgt ccctgcacaa gaaaagaact tcacaactgc   24780
tcctgccatt tgtcatgatg gaaaagcaca ctttcctcgt gaaggtgtct ttgtttcaaa   24840
tggcacacac tggtttgtaa cacaaaggaa ttttatgaa ccacaaatca ttactacaga   24900
caacacattt gtgtctggta actgtgatgt tgtaatagga attgtcaaca acacagttta   24960
tgatcctttg caacctgaat tagactcatt caaggaggag ttagataaat attttaagaa   25020
tcatacatca ccagatgttg atttaggtga catctctggc attaatgctt cagttgtaaa   25080
cattcaaaaa gaaattgacc gcctcaatga ggttgccaag aatttaaatg aatctctcat   25140
cgatctccaa gaacttggaa agtatgagca gtatataaaa tggccatggt acatttggct   25200
aggttttata gctggcttga ttgccatagt aatggtgaca attatgcttt gctgtatgac   25260
cagttgctgt agttgtctca agggctgttg ttcttgtgga tcctgctgca aatttgatga   25320
agacgactct gagccagtgc tcaaaggagt caaattacat tacacataaa cgaacttatg   25380
gatttgttta tgagaatctt cacaattgga actgtaactt tgaagcaagg tgaaatcaag   25440
gatgctactc cttcagattt tgttcgcgct actgcaacga taccgataca agcctcactc   25500
cctttcggat ggcttattgt tggcgttgca cttcttgctg tttttcagag cgcttccaaa   25560
atcataaccc tcaaaagag atggcaacta gcactctcca agggtgttca ctttgtttgc   25620
aacttgctgt tgttgtttgt aacagtttac tcacaccttt gctcgttgc tgctggcctt   25680 gaagcccctt ttctctatct ttatgcttta gtctacttct tgcagagtat aaactttgta   25740
agaataataa tgaggctttg gctttgctgg aaatgccgtt ccaaaaaccc attactttat   25800
gatgccaact attttctttg ctggcatact aattgttacg actattgtat accttacaat   25860
agtgtaactt cttcaattgt cattacttca ggtgatggca caacaagtcc tatttctgaa   25920
catgactacc agattggtgg ttatactgaa aaatgggaat ctggagtaaa agactgtgtt   25980
gtattacaca gttacttcac ttcagactat taccagctgt actcaactca attgagtaca   26040
gacactggtg ttgaacatgt taccttcttc atctacaata aaattgttga tgagcctgaa   26100
gaacatgtcc aaattcacac aatcgacggt tcatccggag ttgttaatcc agtaatggaa   26160
ccaatttatg atgaaccgac gacgactact agcgtgcctt tgtaagcaca agctgatgag   26220
tacgaactta tgtactcatt cgtttcggaa gagacaggta cgttaatagt taatagcgta   26280 cttcttttc ttgctttcgt ggtattcttg ctagttacac tagccatcct tactgcgctt   26340
cgattgtgtg cgtactgctg caatattgtt aacgtgagtc ttgtaaaacc ttcttttttac   26400 gtttactctc gtgttaaaaa tctgaattct tctagagttc ctgatcttct ggtctaaacg   26460
aactaaatat tatattagtt tttctgtttg gaactttaat tttagccatg gcagattcca   26520
acggtactat taccgttgaa gagcttaaaa agctccttga acaatggaac ctagtaatag   26580
gtttcctatt ccttacatgg atttgtcttc tacaatttgc ctatgccaac aggaataggt   26640
```

-continued

| | |
|---|---|
| ttttgtatat aattaagtta attttcctct ggctgttatg gccagtaact ttagcttgtt | 26700 |
| ttgtgcttgc tgctgtttac agaataaatt ggatcaccgg tggaattgct atcgcaatgg | 26760 |
| cttgtcttgt aggcttgatg tggctcagct acttcattgc ttctttcaga ctgtttgcgc | 26820 |
| gtacgcgttc catgtggtca ttcaatccag aaactaacat tcttctcaac gtgccactcc | 26880 |
| atggcactat tctgaccaga ccgcttctag aaagtgaact cgtaatcgga gctgtgatcc | 26940 |
| ttcgtggaca tcttcgtatt gctggacacc atctaggacg ctgtgacatc aaggacctgc | 27000 |
| ctaaagaaat cactgttgct acatcacgaa cgctttctta ttacaaattg ggagcttcgc | 27060 |
| agcgtgtagc aggtgactca ggttttgctg catacagtcg ctacaggatt ggcaactata | 27120 |
| aattaaacac agaccattcc agtagcagtg acaatattgc tttgcttgta cagtaagtga | 27180 |
| caacagatgt ttcatctcgt tgactttcag gttactatag cagagatatt actaattatt | 27240 |
| atgaggactt ttaaagtttc catttggaat cttgattaca tcataaacct cataattaaa | 27300 |
| aatttatcta agtcactaac tgagaataaa tattctcaat tagatgaaga gcaaccaatg | 27360 |
| gagattgatt aaacgaacat gaaaattatt cttttcttgg cactgataac actcgctact | 27420 |
| tgtgagcttt atcactacca agagtgtgtt agaggtacaa cagtactttt aaaagaacct | 27480 |
| tgctcttctg gaacatacga gggcaattca ccatttcatc ctctagctga taacaaattt | 27540 |
| gcactgactt gctttagcac tcaatttgct tttgcttgtc ctgacggcgt aaaacacgtc | 27600 |
| tatcagttac gtgccagatc agtttcacct aaactgttca tcagacaaga ggaagttcaa | 27660 |
| gaactttact ctccaatttt tcttattgtt gcggcaatag tgtttataac actttgcttc | 27720 |
| acactcaaaa gaaagacaga atgattgaac tttcattaat tgacttctat ttgtgctttt | 27780 |
| tagcctttct gctattcctt gttttaatta tgcttattat cttttggttc tcacttgaac | 27840 |
| tgcaagatca taatgaaact tgtcacgcct aaacgaacat gaaatttctt gttttcttag | 27900 |
| gaatcatcac aactgtagct gcatttcacc aagaatgtag tttacagtca tgtactcaac | 27960 |
| atcaaccata tgtagttgat gacccgtgtc ctattcactt ctattctaaa tggtatatta | 28020 |
| gagtaggagc tagaaaatca gcacctttaa ttgaattgtg cgtggatgag gctggttcta | 28080 |
| aatcacccat tcagtacatc gatatcggta attatacagt ttcctgttta ccttttacaa | 28140 |
| ttaattgcca ggaacctaaa ttgggtagtc ttgtagtgcg ttgttcgttc tatgaagact | 28200 |
| ttttagagta tcatgacgtt cgtgttgttt tagatttcat ctaaacgaac aaactaaaat | 28260 |
| gtctgataat ggaccccaaa atcagcgaaa tgcaccccgc attacgtttg gtggaccctc | 28320 |
| agattcaact ggcagtaacc agaatggaga acgcagtggg gcgcgatcaa acaacgtcg | 28380 |
| gccccaaggt ttacccaata atactgcgtc ttggttcacc gctctcactc aacatggcaa | 28440 |
| ggaagacctt aaattccctc gaggacaagg cgttccaatt aacaccaata gcagtccaga | 28500 |
| tgaccaaatt ggctactacc gaagagctac cagacgaatt cgtggtggtg acggtaaaat | 28560 |
| gaaagatctc agtccaagat ggtatttcta ctacctagga actgggccag aagctggact | 28620 |
| tccctatggt gctaacaaag acggcatcat atgggttgca actgagggag ccttgaatac | 28680 |
| accaaaagat cacattggca cccgcaatcc tgctaacaat gctgcaatcg tgctacaact | 28740 |
| tcctcaagga acaacattgc caaaaggctt ctacgcagaa gggagcagag gcggcagtca | 28800 |
| agcctcttct cgttcctcat cacgtagtcg caacagttca agaaattcaa ctccaggcag | 28860 |
| cagtaggggga acttctcctg ctagaatggc tggcaatggc ggtgatgctg ctcttgcttt | 28920 |
| gctgctgctt gacagattga accagcttga gagcaaaatg tctggtaaag gccaacaaca | 28980 |
| acaaggccaa actgtcacta agaaatctgc tgctgaggct tctaagaagc ctcggcaaaa | 29040 |

```
acgtactgcc actaaagcat acaatgtaac acaagctttc ggcagacgtg gtccagaaca    29100
aacccaagga aattttgggg accaggaact aatcagacaa ggaactgatt acaaacattg    29160
gccgcaaatt gcacaatttg cccccagcgc ttcagcgttc ttcggaatgt cgcgcattgg    29220
catggaagtc acaccttcgg gaacgtggtt gacctacaca ggtgccatca aattggatga    29280
caaagatcca aatttcaaag atcaagtcat tttgctgaat aagcatattg acgcatacaa    29340
aacattccca ccaacagagc ctaaaaagga caaaagaag aaggctgatg aaactcaagc    29400
cttaccgcag agacagaaga aacagcaaac tgtgactctt cttcctgctg cagatttgga    29460
tgatttctcc aaacaattgc aacaatccat gagcagtgct gactcaactc aggcctaaac    29520
tcatgcagac cacacaaggc agatgggcta tataaacgtt ttcgcttttc cgtttacgat    29580
atatagtcta ctcttgtgca gaatgaattc tcgtaactac atagcacaag tagatgtagt    29640
taactttaat ctcacatagc aatctttaat cagtgtgtaa cattagggag gacttgaaag    29700
agccaccaca ttttcaccga ggccacgcgg agtacgatcg agtgtacagt gaacaatgct    29760
agggagagct gcctatatgg aagagcccta atgtgtaaaa ttaattttag t             29811
```